US011869666B2

(12) United States Patent
Heimerl

(10) Patent No.: US 11,869,666 B2
(45) Date of Patent: Jan. 9, 2024

(54) COMPUTER SYSTEM FOR CRISIS STATE DETECTION AND INTERVENTION

(71) Applicant: Kristen M. Heimerl, Minnetonka, MN (US)

(72) Inventor: Kristen M. Heimerl, Minnetonka, MN (US)

(73) Assignee: Kristen M. Heimerl, Minnetonka, MN (US)

( * ) Notice: Subject to any disclaimer, the term of this patent is extended or adjusted under 35 U.S.C. 154(b) by 397 days.

(21) Appl. No.: 17/141,019

(22) Filed: Jan. 4, 2021

(65) Prior Publication Data

US 2021/0217533 A1 Jul. 15, 2021

Related U.S. Application Data

(60) Provisional application No. 63/054,230, filed on Jul. 20, 2020, provisional application No. 62/959,858, filed on Jan. 10, 2020.

(51) Int. Cl.
*G16H 50/30* (2018.01)
*H04M 1/72421* (2021.01)
(Continued)

(52) U.S. Cl.
CPC ........... *G16H 50/30* (2018.01); *A61B 5/0004* (2013.01); *A61B 5/0022* (2013.01); *A61B 5/01* (2013.01); *A61B 5/024* (2013.01); *A61B 5/026* (2013.01); *A61B 5/08* (2013.01); *A61B 5/11* (2013.01); *A61B 5/117* (2013.01); *A61B 5/14517* (2013.01); *A61B 5/165* (2013.01); *A61B 5/7264* (2013.01); *A61B 5/742* (2013.01); *A61B 5/7405* (2013.01); *G06Q 50/265* (2013.01); *G16H 20/70* (2018.01); *G16H 40/67* (2018.01); *G16H 50/20* (2018.01); *G16Y 10/60* (2020.01); *H04M 1/72421* (2021.01); *H04M 1/27453* (2020.01)

(58) Field of Classification Search
CPC .............................. G16H 50/30; A61B 5/0022
See application file for complete search history.

(56) References Cited

U.S. PATENT DOCUMENTS 6,934,954 B1 8/2005 Crites et al.
9,313,634 B2 4/2016 Suzuki et al.
(Continued)

OTHER PUBLICATIONS

Robert S. H. Istepanian; Bryan Woodward, "Smart m-Health Sensing," in m-Health: Fundamentals and Applications, IEEE, 2017, pp. 23-66 (Year: 2017).*

(Continued)

*Primary Examiner* — Sheetal R Paulson
(74) *Attorney, Agent, or Firm* — Barnes & Thornburg LLP

(57) ABSTRACT

The disclosed technology provides a system and a computer implemented method for crisis state detection and intervention of a person or group of persons, the method comprising: providing a computer system designed to detect and intervene non-normal, elevated crisis operating states; using one or more biometric sensors that ascertains a crisis state via physical, behavioral, or mental indicators; deducing, with computational hardware, the operational state of a user or users from one or more biometric sensors; and administering an immediate, dual intervention of a sensory form to de-escalate the crisis operating state of a person or group of persons.

20 Claims, 25 Drawing Sheets

3 Things Affect Our Stress Levels:

1. Personal Factors

2. Physical Environment Factors

3. Social Environment Factors

(51) Int. Cl.
| | | |
|---|---|---|
| A61B 5/00 | (2006.01) | |
| G16H 40/67 | (2018.01) | |
| A61B 5/01 | (2006.01) | |
| A61B 5/024 | (2006.01) | |
| A61B 5/026 | (2006.01) | |
| A61B 5/08 | (2006.01) | |
| A61B 5/11 | (2006.01) | |
| A61B 5/117 | (2016.01) | |
| A61B 5/145 | (2006.01) | |
| G06Q 50/26 | (2012.01) | |
| A61B 5/16 | (2006.01) | |
| G16H 20/70 | (2018.01) | |
| G16H 50/20 | (2018.01) | |
| G16Y 10/60 | (2020.01) | |
| H04M 1/27453 | (2020.01) | |

(56) References Cited

U.S. PATENT DOCUMENTS

| | | | |
|---|---|---|---|
| 9,566,411 | B1 | 2/2017 | Sherpa et al. |
| 10,191,537 | B2 | 1/2019 | Tanaka et al. |
| 10,339,781 | B2 | 7/2019 | Kaplan et al. |
| 10,561,321 | B2 * | 2/2020 | Valys ............... A61B 5/7267 |
| 10,692,606 | B2 | 6/2020 | Bender et al. |
| 11,598,544 | B1 * | 3/2023 | Schubert ............... F24F 11/46 |
| 11,607,182 | B2 * | 3/2023 | Fountaine ............ G08B 25/016 |
| 2015/0288797 | A1 * | 10/2015 | Vincent ............... G16H 10/60 455/404.2 |
| 2017/0011210 | A1 * | 1/2017 | Cheong ............... A61B 5/681 |
| 2017/0039045 | A1 | 2/2017 | Abraham et al. |
| 2017/0347907 | A1 | 12/2017 | Le et al. |
| 2019/0074089 | A1 * | 3/2019 | Kochura ............... G16H 50/20 |
| 2019/0189025 | A1 * | 6/2019 | Angelopoulos ........ G16H 20/10 |
| 2019/0209022 | A1 * | 7/2019 | Sobol ............... A61B 5/0022 |
| 2020/0037904 | A1 * | 2/2020 | Tegen ............... A61B 5/746 |
| 2021/0145338 | A1 * | 5/2021 | Borthakur ............... G16H 10/20 |
| 2021/0217532 | A1 | 7/2021 | Heimerl |
| 2021/0225507 | A1 * | 7/2021 | Van Kollenburg .... G16H 50/70 |
| 2022/0384027 | A1 * | 12/2022 | Kaleal, III ............. G16H 20/40 |

OTHER PUBLICATIONS

[No author listed], "Workplace violence: a growing threat, or growing in awareness?" SHRM Better Workplaces Better World, Mar. 2019, 5 pages.

[No author listed], "Workplace violence: a growing threat, or growing in awareness?" SHRM Better Workplaces Better World, retrieved on Aug. 4, 2020, 1 page.

AdAge.com [online], "5 consumer trends that will endure after covid-19, and what they mean for marketers," Apr. 2020, retrieved on Aug. 4, 2020, retrieved from URL <https://adage.com/article/cmo-strategy/5-consumer-trends-will-endure-after-covid-19-and-what-they-mean-marketers/2247986>, 14 pages.

AGreenStore.com [online], "FeverWatch body temperature SMART monitor bracelet bluetooth heartrate—a green store," available on Oct. 23, 2020, via Internet Archive: Wayback Machine URL <https://web.archive.org/web/20201023061400/https://agreenstore.com/products/feverwatch%E2%84%A2-2-0-body-temperature-smart-monitor-watch-ecg-sleep-waterproof-bluetooth-heartrate-fitness-tracker>, retrieved on Apr. 1, 2022, URL <https://agreenstore.com/products/feverwatch™-2-0-body-temperature-smart-monitor-watch-ecg-sleep-waterproof-bluetooth-heartrate-fitness-tracker>, 6 pages.

Amazon.com [online] "Room temperature monitor," retrieved on Jul. 31, 2020, retrieved from URL <https://www.amazon.com/Room-Temperature-monitor/s?k=Room+Temperature+Monitor>, 4 pages.

AnxietyCentre.com [online], "Change in body temperature caused by anxiety," Feb. 2020, retrieved on Jul. 30, 2020, retrieved from URL<https://www.anxietycentre.com/anxiety-disorders/symptoms/change-in-body-temperature/>, 4 pages.

Bailey, "Looking back to the future: the re-emergence of green care," BJPsych International, Nov. 2017,14(4):79.

BehavioralEconomics.com [online], "Herd Behavior," available on Jan. 11, 2020, via Internet Archive: Wayback Machine URL <https://web.archive.org/web/20200111220819/https://www.behavioraleconomics.com/resources/mini-encyclopedia-of-be/herd-behavior/>, retrieved on Apr. 1, 2022 URL <https://www.behavioraleconomics.com/resources/mini-encyclopedia-of-be/herd-behavior/>, 3 pages.

BeyondIntractability.org [online] "The necessity of social structural change," Jul. 2003, retrieved on Jul. 31, 2020, retrieved from URL <https://www.beyondintractability.org/ssay/social_structural_changes>, 12 pages.

Blog.Bonus.ly [online], "21 expert antidotes for a toxic work environment," Jan. 27, 2016, retrieved on Aug. 4, 2020, retrieved from URL, <https://blog.bonus.ly/20-expert-antidotes-for-a-toxic-work-environment/>, 29 pages.

BusinessInsider.com [online] "Employees at the world's largest hedge fund use iPads to rate each other's performance in real-time—see how it works," Sep. 2017, retrieved on Aug. 4, 2020, retrieved from URL <https://www.businessinsider.com/bridgewater-ray-dalio-radical-transparency-app-dots-2017-9>, 26 pages.

Businesswire.com [online] "New Survey Reveals Toxic Cultures and Negative Behaviors are Prevalent in the Workplace," Nov. 2019, retrieved on Jul. 31, 2020, retrieved from <https://www.businesswire.com/news/home/20191120005080/en/New-Survey-Reveals-Toxic-Cultures-%20Negative-Behaviors> 3 pages.

CBC.ca [online], "Green space improves mental health, well-being: Researchers found exposure to green space improved well-being both immediately and over time," Jun. 2014, retrieved on Jul. 31, 2020, retrieved from URL <https://www.cbc.ca/news/health/green-space-improves-mental-health-well-being-1.2672323>, 6 pages.

CDC.gov [online], "Violence in the workplace," Jul. 1996, retrieved on Jul. 30, 2020, retrieved from URL <https://www.cdc.gov/niosh/docs/96-100/introduction.html>, 3 pages.

Chatelaine.com [online], "The toxic effects of workplace stress," Sep. 2018, retrieved on Jul. 31, 2020, retrieved from URL <https://www.chatelaine.com/health/wellness/the-toxic-effects-of-workplace-stress/>, 6 pages.

Colenberg et al., "The relationship between interior office space and employee health and well-being—a literature review," Building Research & Information, Jan. 2020, 16 pages.

Conoley et al., "Integrating positive psychology into family therapy: Positive family therapy," The Counseling Psychologist, Jul. 2015, 43(5):703-733.

ControlServices.com [online], "What is Building Automation," available on Jan. 10, 2015, via Internet Archive: Wayback Machine URL <https://web.archive.org/web/20150110045940/http://www.controlservices.com/learning_automation.htm>, retrieved on Apr. 1, 2022, URL <http://www.controlservices.com/learning_automation.htm>, 7 pages.

Damousis et al., "Four machine learning algorithms for biometrics fusion: A comparative study," Applied Computational Intelligence and Soft Computing, Jan. 2012, 2012:8 pages.

Developers.facebook.com [online] "Best Practices on Instant Games," available on Mar. 18, 2022 via Internet Archive: Wayback Machine URL <https://developers.facebook.com/docs/games/monetization/best-practices>, retrieved on Apr. 1, 2022, URL <https://developers.facebook.com/docs/games/monetization/best-practices>.

En.wikipedia.org [online], "Toxic workplace," Mar. 2020, retrieved on Jul. 30, 2020, retrieved from URL <https://en.wikipedia.org/wiki/Toxic_workplace>, 4 pages.

Especialneeds.com [online] "Sensory Rooms, explained," Feb. 2019, retrieved on Jul. 31, 2020, retrieved from URL <https://www.especialneeds.com/blog/landing-pages/sensory-rooms/>, 15 pages.

Evans, "The built environment and mental health," Journal of Urban Health: Bulletin of the New York Academy of Medicine, Dec. 2003, 80(4):536-555.

Fitnessprofessionalonline.com [online], "Using group heart rate monitoring to improve results and sales of group HIIT Training," Jan. 2015, retrieved Jul. 30, 2020, retrieved from URL <https://www.fitnessprofessionalonline.com/articles/expert-advice/using-group-heart-rate-monitoring-to-improve-results-and-sales-of-group-hiit-training/>, 9 pages.

(56) References Cited

OTHER PUBLICATIONS

Forbes.com [online], "How does lighting affect mental health in the workplace," Dec. 2018, retrieved on Jul. 31, 2020, retrieved from URL <https://www.forbes.com/sites/pragyaagarwaleurope/2018/12/31/how-does-lighting-affect-mental-health-in-the-workplace/?sh=340ff4cc4ccd>, 5 pages.
Forbes.com [online], "Why breaking down hierarchies will get the most out of talent," Jan. 14, 2019, retrieved on Jul. 31, 2020, retrieved from URL <https://www.forbes.com/sites/jasondownes1/2019/01/14/why-breaking-down-hierarchies-will-get-the-most-out-of-talent/?sh=75f83c0clbc3>, 5 pages.
Georgiou et al., "Can wearable devices accurately measure heart rate variability? A systematic review," Folia Medica, Feb. 2018, 60(1):15 pages.
Gonzalez et al., "Hair cortisol measurement by an automated method," Scientific Reports, Jun. 2019, 9(1):1-6.
Han et al., "Bergamot (Citrus bergamia) essential oil inhalation improves positive feelings in the waiting room of a mental health treatment center: A pilot study," Phytotherapy Research, May 2017, 31(5):812-816.
Hashoul et al., "Sensors for detecting pulmonary diseases from exhaled breath," European Respiratory Review, Jun. 2019, 28(152):13 pages.
Hcamag.com [online], "Five biggest drivers of workplace stress—and how to fight them," Apr. 2019, retrieved on Aug. 4, 2020, retrieved from URL <https://www.hcamag.com/au/news/general/five-biggest-drivers-of-workplace-stress-and-how-to-fight-them/165110>, 6 pages.
Healey et al., "Detecting stress during real-world driving tasks using physiological sensors," IEEE Journals & Magazine, Jun. 2005, 6(2):28 pages.
Heart.org [online] Spend time in nature to reduce stress and anxiety, Aug. 2018, retrieved on Jul. 30, 2020, retrieved from URL <https://www.heart.org/en/healthy-living/healthy-lifestyle/stress-management/spend-time-in-nature-to-reduce-stress-and-anxiety>, 6 pages.
Herborn et al., "Skin temperature reveals the intensity of acute stress," Physiology & Behavior, Dec. 2015, 152:225-230.
Howard et al., "Expectancies, not aroma, explain impact of lavender aromatherapy on psychophysiological indices of relaxation in young healthy women," British Journal of Health Psychology, Nov. 2008, 13:603-617.
Hr.com [online] "Preventing toxic workplaces: The role of values, training, and leadership in promoting a positive workplace culture," Nov. 2019, retrieved on Jul. 31, 2020, retrieved from URL <https://www.hr.com/en/resources/free_research_white_papers/hrcom-preventing-toxic-workplaces-2019-research_k2nrdqt2.html>, 21 pages.
Inc.com [online], "4 devastating consequences of a toxic workplace culture when fear permeates an organization, its leaders are living on borrowed time," available on Nov. 5, 2019, via Internet Archive: Wayback Machine URL <https://www.inc.com/tanya-prive/4-devastating-consequences-of-a-toxic-workplace-culture.html>, retrieved on Apr. 1, 2022, URL <https://www.inc.com/tanya-prive/4-devastating-consequences-of-a-toxic-workplace-culture.html>.
Inc.com [online], "8 best industries for starting a business in 2020," Feb. 4, 2020, retrieved on Aug. 4, 2020, retrieved from URL <https://www.inc.com/best-industries-2020.html>, 11 pages.
Itoh et al., "Development of an exhaled breath monitoring system with semiconductive gas sensors, a gas condenser unit, and gas chromatograph columns," Sensors, Nov. 2016, 16(11):16 pages.
Kim et al., "Emotion recognition system using short-term monitoring of physiological signals," Medical and Biological Engineering and Computing, May 2004, 42(3):419-27.
Kutlu et al., "Effects of aroma inhalation on examination anxiety," Teaching and Learning in Nursing, Oct. 2008, 3(4):125-130.
Lansisalmi et al., "Collective stress and coping in the context of organizational culture," European Journal of Work and Organizational Psychology, Dec. 2000, 9(4):527-559.
Liang et al., "Real-time detection of driver cognitive distraction using support vector machines," IEEE Transactions on Intelligent Transportation Systems, Jun. 2007, 8(2):340-350.
Loriol et al., "Collective forms of coping and the social construction of work stress among industrial workers and police officers in France," Theory & Psychology, Feb. 2016, 26(1):112-129.
Macworld.com [online], "Apple Watch Series 3 vs Fitbit Versa 2: Even a two-year-old Apple Watch is hard to beat," Nov. 22, 2019, retrieved on Jul. 30, 2022, retrieved from URL <https://www.macworld.com/article/233301/fitbit-versa-2-vs-apple-watch-series-3-specs-features-price.html>, 13 pages.
Mayoclinic.org [online], "Thermometers: understand the options," Nov. 2020, retrieved on Jul. 31, 2020, retrieved from URL <https://www.mayoclinic.org/diseases-conditions/fever/in-depth/thermometers/art-20046737?p=1>, 4 pages.
McKinsey & Company, "AI, automation, and the future of work: ten things to solve for," Prepared for the Tech4good Summit, Organized by The French Presidency, Jun. 2018, 7 pages.
McLaughlin et al., "Developing an organisation culture to facilitate radical innovation," International Journal of Technology Management, Oct. 2008, 44:27 pages.
Mental illness in the workplace: Psychological disability management, Harder et al., Jul. 2014, 406 pages (abstract only).
MindTools.com [online], "Why Good Employees Go Bad—#MTtalk Roundup," Aug. 2016, retrieved on Jul. 31, 2020, retrieved from URL <https://www.mindtools.com/blog/mttalk-good-employees-bad/>, 5 pages.
Motivations for promotion and prevention, Molden et al., in Handbook of motivation science, Jan. 2008, chapter 11:169-87.
Musicant et al., "Supervised learning by training on aggregate outputs," Seventh IEEE International Conference on Data Mining, Oct. 2007, 10 pages.
Nam et al., "Monitoring of heart and breathing rates using dual cameras on a smartphone," PloS one, Mar. 2016, 11(3):15 pages.
Nytimes.com [online], "The Unbearable heaviness of Clutter," Jan. 2019, retrieved on Aug. 4, 2020, retrieved from URL <https://www.nytimes.com/2019/01/03/well/mind/clutter-stress-procrastination-psychology.html>, 2 pages.
Padilla et al., "The toxic triangle: Destructive leaders, susceptible followers, and conducive environments," The Leadership Quarterly, Jun. 2007, 18(3):176-194.
PaintedBrain.org [online], "Aromatherapy and mental wellbeing," Jun. 2019, retrieved on Jul. 31, 2020, retrieved from <https://paintedbrain.org/news/aromatherapy-and-mental-wellbeing/>, 6 pages.
Picard et al., "Toward machine emotional intelligence: Analysis of affective physiological state," IEEE Transactions on Pattern Analysis and Machine Intelligence, Oct. 2001, 23(10):1175-1191.
ProgressFocusedApproach.com [online], "Approach/avoidance and promotion/prevention," available on or before Feb. 5, 2015, via Internet Archive: Wayback Machine URL <http://web.archive.org/web/20150205034025/http://www.progressfocusedapproach.com/approachavoidance-and-promotionprevention/>, retrieved on Jul. 31, 2020, URL <http://www.progressfocusedapproach.com/approachavoidance-and-promotionprevention/>, 2 pages.
Psychologicalscience.org [online], "The slippery-slope effect: minor misdeeds lead to major ones," Mar. 2015, retrieved on Jul. 31, 2020, retrieved from URL <https://www.psychologicalscience.org/news/minds-business/the-slippery-slope-effect-minor-misdeeds-%20lead-to-major-ones.html>, 8 pages.
Sciencedaily.com [online], "Stressed? Take a 20-minute 'nature pill'," Apr. 2019, retrieved on Jul. 30, 2020, retrieved from URL <https://www.sciencedaily.com/releases/2019/04/190404074915.htm>, 3 pages.
Stress.org [online], "42 worrying workplace stress statistics," Sep. 25, 2019, retrieved on Jul. 31, 2020, retrieved from URL <https://www.stress.org/42-worrying-workplace-stress-statistics>, 29 pages.
Supportz.com [online], "5 free android apps that function as thermometers," Dec. 2014, retrieved on Jul. 31, 2020, retrieved from URL <https://supportz.com/5-free-android-apps-that-function-as-thermometers/> 9 pages.
torbenrick.eu [online], "Top 30+ key obstacles to innovation," Sep. 2014, retrieved on Aug. 4, 2020, retrieved from URL <https://www.torbenrick.eu/blog/strategy/30-key-obstacles-to-innovation/>, 5 pages.
TowardsDatascience.com [online] "K-means Clustering: Algorithm, Applications, Evaluation Methods, and Drawbacks," Sep.

(56) References Cited

OTHER PUBLICATIONS 2018, retrieved from <https://towardsdatascience.com/k-means-clustering-algorithm-applications-evaluation-methods-and-drawbacks-aa03e644b48a>, 15 pages.

Unbc.ca [online], "Harder, Dr. Henry," retrieved on Jul. 31, 2020, retrieved from <https://www2.unbc.ca/people/harder-dr-henry>, 2 pages.

Van den Bosch M et al., "Environmental exposures and depression: biological mechanisms and epidemiological evidence," Annual Review of Public Health, Jan. 2019, 40:239-259.

Vice.com [online], "Watching fish swim is an odd but effective way to relax," Feb. 2018, retrieved on Jul. 31, 2020, retrieved from <https://www.vice.com/en/article/qvep4q/aquarium-therapy-good-for-health>, 15 pages.

Weeks, Aesthetics and interior design: effects on overall mental health, Rocky Mountain Products, retrieved on Jul. 31, 2020, 8 pages.

Wells et al., "Associations of hair cortisol concentration with self-reported measures of stress and mental health-related factors in a pooled database of diverse community samples," Stress, Jul. 2014, 17(4):334-342.

Welsh, III et al., "ILJS International journal of leadership studies," Winter 2011, 7(1):142 pages.

What is "Positive Family Therapy?" Peseschkian, Dec. 2012, 340 pages (abstract only).

Whywelikethis-ca.com [online], "Top 8 best body temperature fitness trackers," retrieved on Jul. 2020, retrieved from URL <https://www.whywelikethis-ca.com/top-8-best-body-temperature-fitness-trackers/>, 16 pages.

Wikipedia.org [online], "Interface (computing)," May 2020, retrieved on Jul. 31, 2020, retrieved from URL <https://en.wikipedia.org/wiki/Interface_(computing)>, 5 pages.

Wojtusiak, "Model Learning from Published Aggregated Data," Learning Structure and Schemas from Documents, Sep. 2011, 3:375:369.

Wright et al., "Hair cortisol analysis: A promising biomarker of HPA activation in older adults," The Gerontologist, Jun. 2015, 55(S1):140-145.

Yu et al., "Driving distraction analysis by ECG signals: an entropy analysis," In International Conference on Internationalization, Design and Global Development, Jul. 2011, 258-264.

Zimbardo, "A situationist perspective on the psychology of evil: Understanding how good people are transformed into perpetrators," in The Social Psychology of Good and Evil, 1st ed., Miller (ed)., Apr. 6, 2005, chapter 2, 16 pages.

* cited by examiner

3 Things Affect Our Stress Levels:

1. Personal Factors
2. Physical Environment Factors
3. Social Environment Factors

FIG. 1

FIG. 5 — User Device(s) and Intervention System/Server

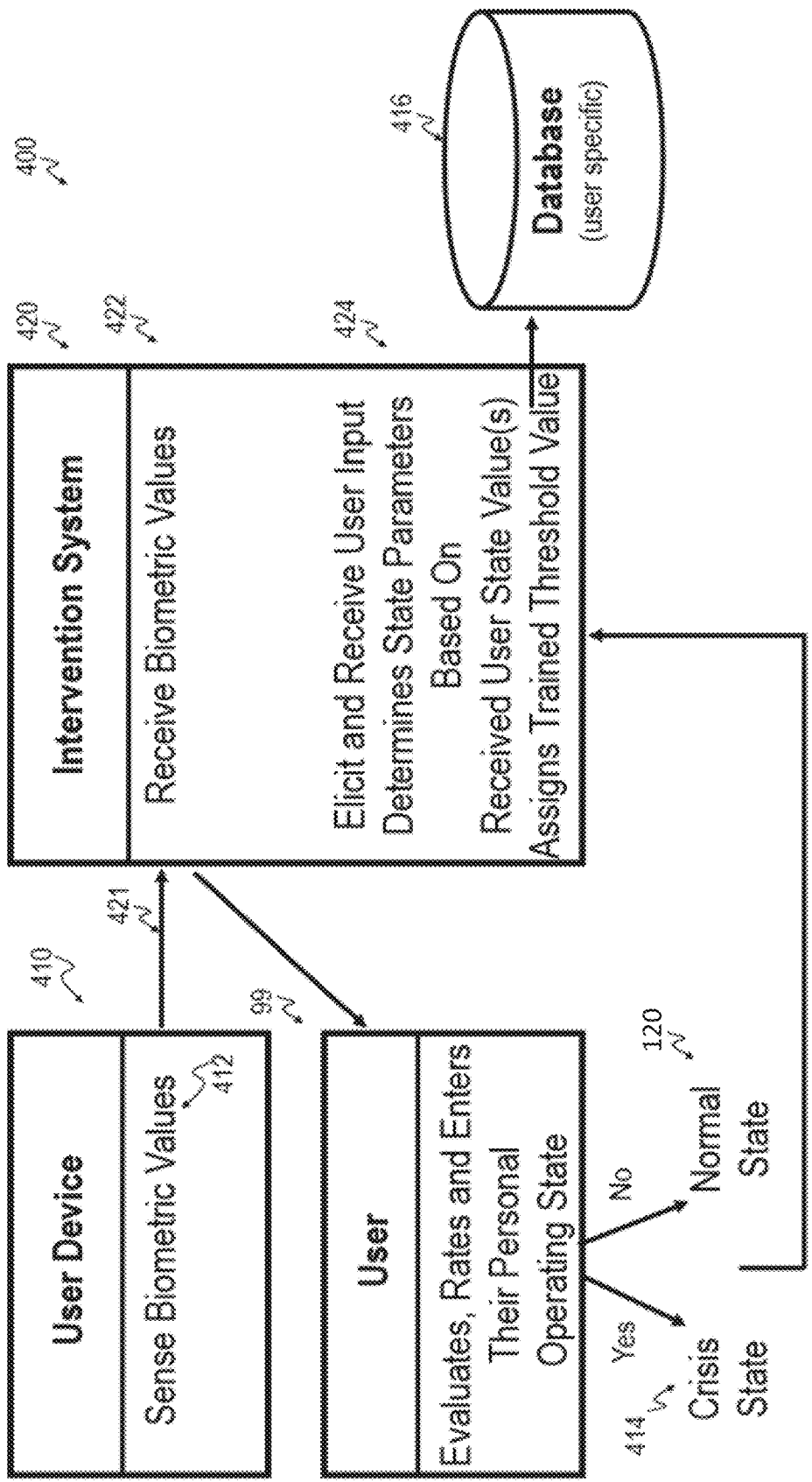
FIG. 7A —Determination (Training) of Baseline Operating State

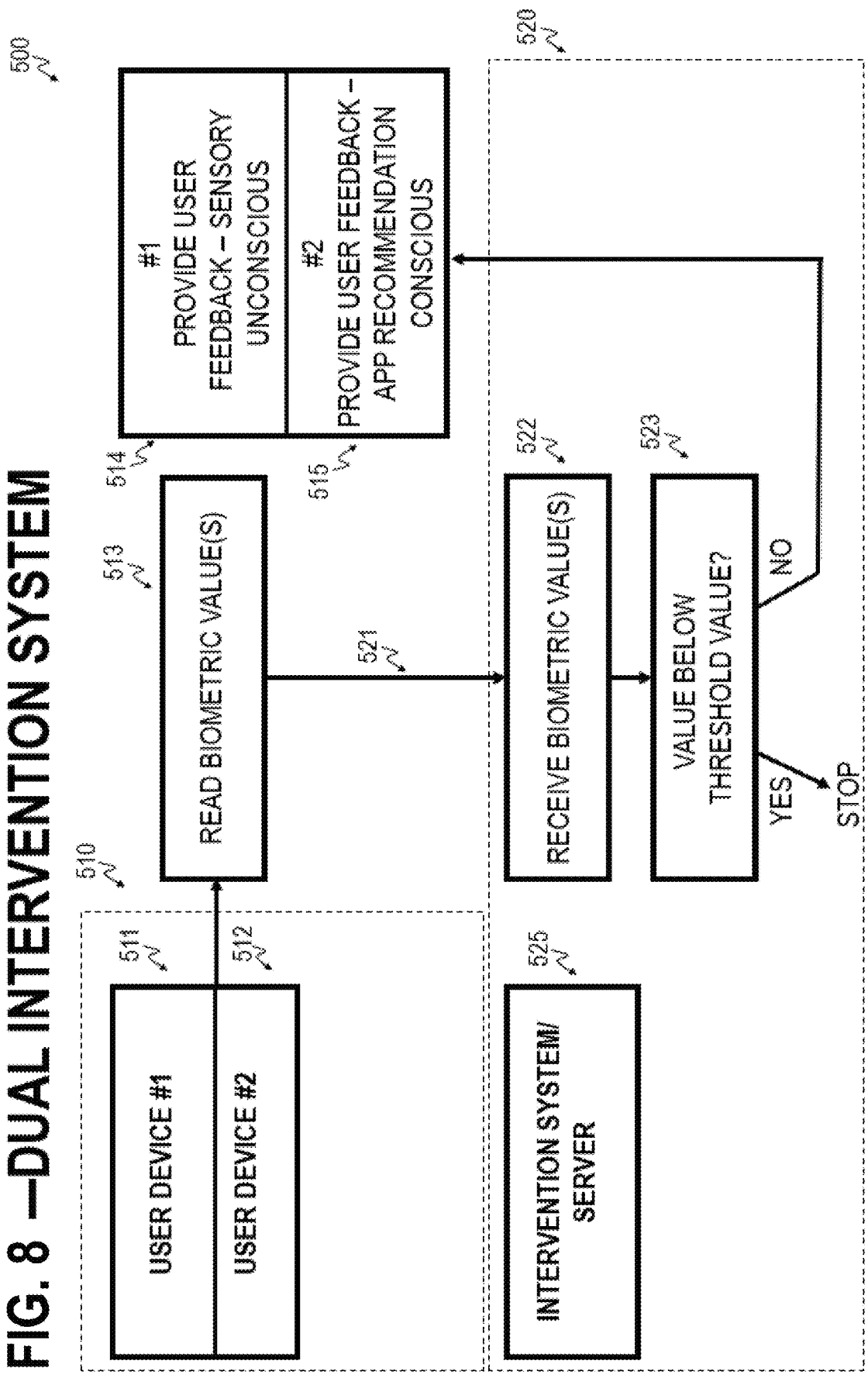

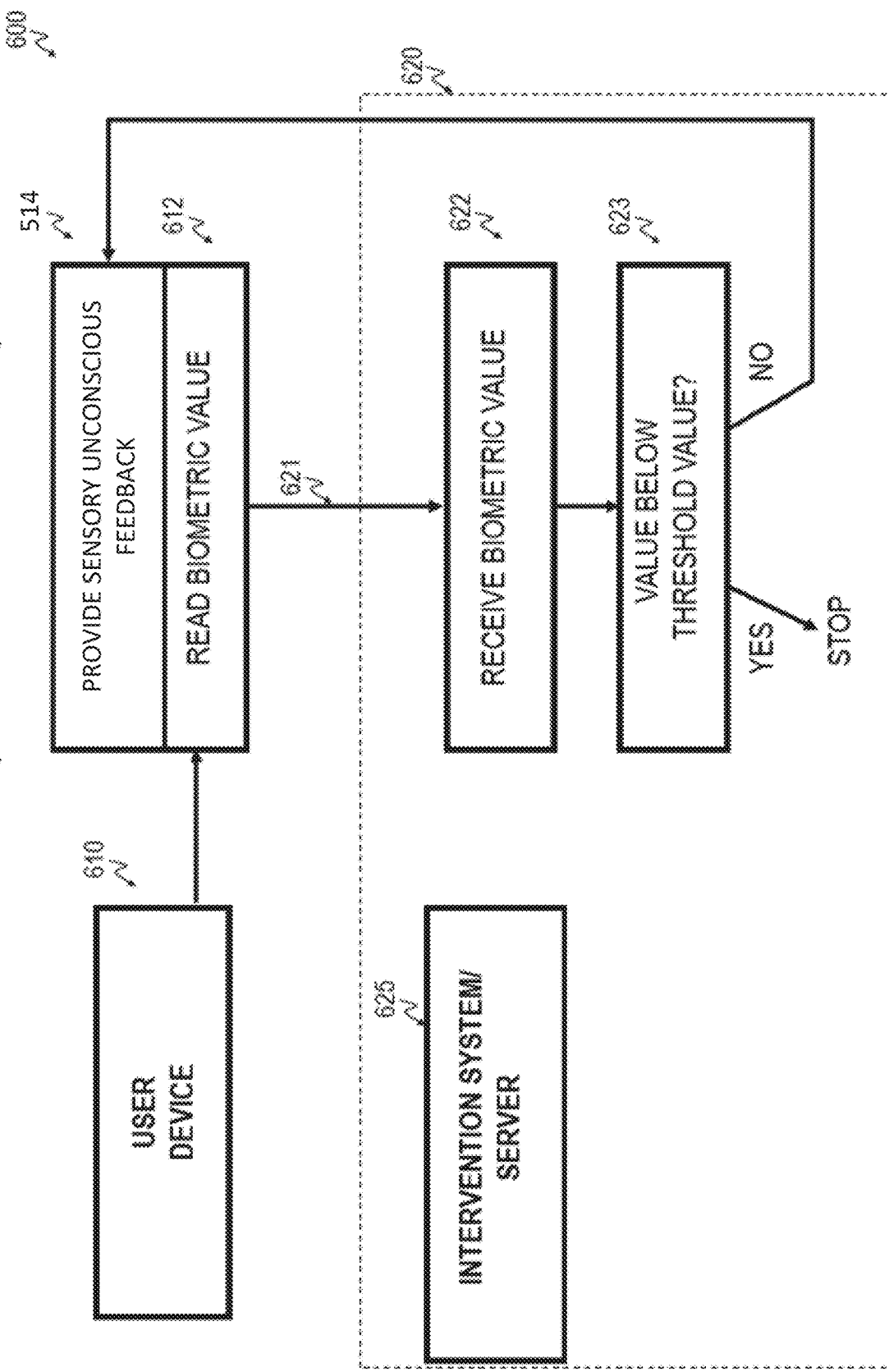

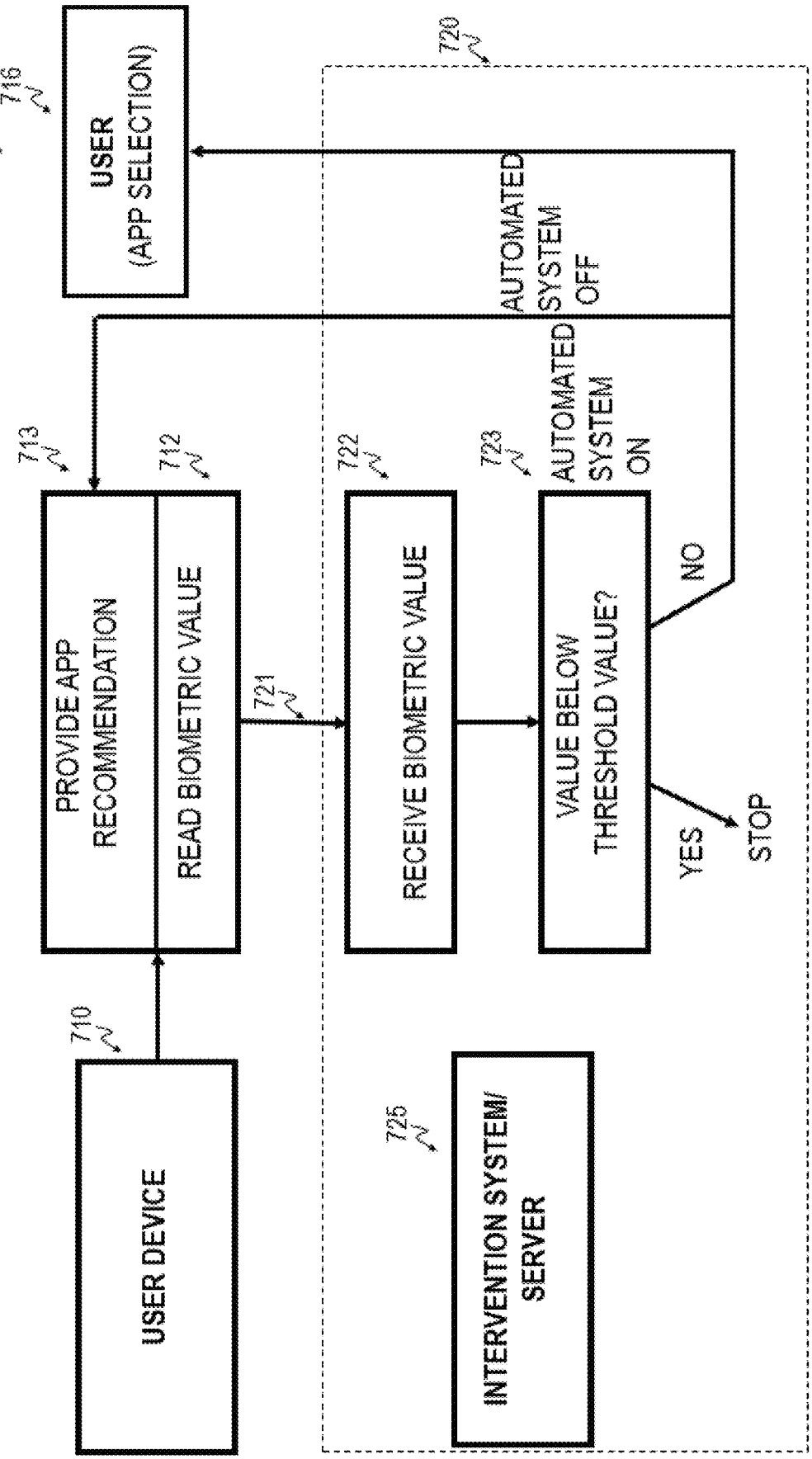
FIG. 10 —CONSCIOUS (PERCEPTIBLE) INTERVENTION

User Interface 783

Post-Intervention Rating Application 784

Post-Intervention Review 791

| Contact | No. Calls | Self-reported outcome | System-reported outcome |
|---|---|---|---|
| #1 | 2 | + | + |
| #2 | 1 | - | + |
| #3 | 4 | + | - |
| #4 | 3 | + | + |
| Anonymous Ally | | | |
| #5 | 4 | + | - |
| #6 | 2 | + | + |

Intervention Type Efficacy 792

| Intervention Type | No. | % Intervention Efficacy |
|---|---|---|
| Listening | 18 | 98% |
| Words of Support | 21 | 93% |
| Action Ideas | 12 | 88% |
| Plan to Meet | 2 | 91% |
| Plan to Talk More | 3 | 85% |

Intervention Type Reporting 793

| Ally ID | No. Calls | Self-reported outcome | System-reported outcome | Action |
|---|---|---|---|---|
| 739 | 2 | 5 | 5 | Request User |
| 991 | 1 | 3 | 1 | Blocked |
| 042 | 3 | 4 | 4 | |
| 671 | 3 | 5 | 5 | Preferred |

FIG. 21

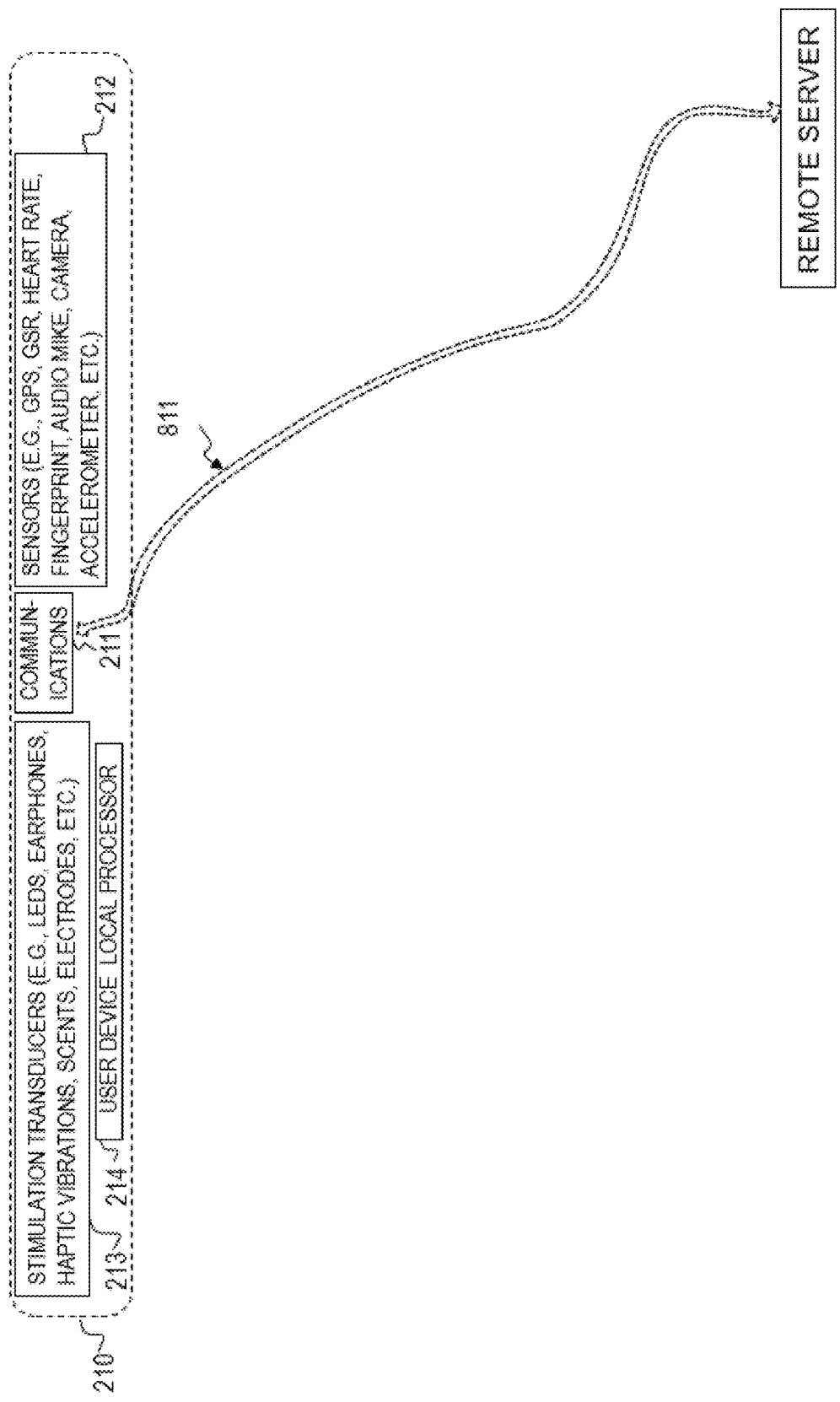

FIG. 24A *(PRIOR ART)*
*CAN MAKE THIS YOUR SYSTEM AS MODIFIED*
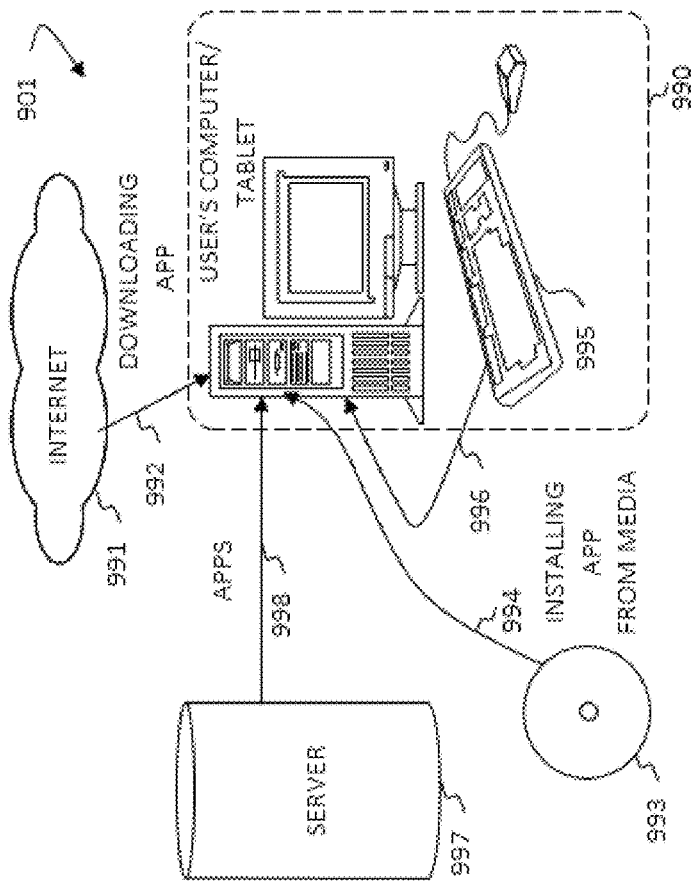
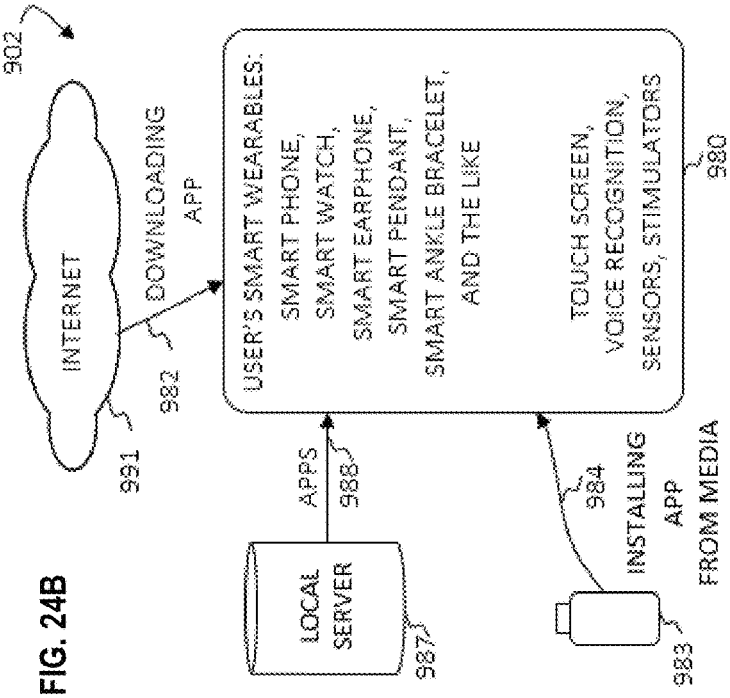
FIG. 24B

COMPUTER SYSTEM FOR CRISIS STATE DETECTION AND INTERVENTION

CROSS-REFERENCE TO RELATED APPLICATIONS

This application claims priority to U.S. Provisional Patent Application No. 62/959,858, filed Jan. 10, 2020 by Kristen M. Heimerl titled "Computer system for crisis state detection and intervention," and U.S. Provisional Patent Application No. 63/054,230, filed Jul. 20, 2020, by Kristen M. Heimerl titled "Computer system for group crisis-state detection and intervention," which are incorporated herein by reference in their entirety.

TECHNICAL FIELD

The disclosed technology relates to providing active feedback to a human individual or group of human individuals, and more particularly to helping achieve an optimal operating state of the human individual or the group of human individuals and, more specifically, to a system and method for detecting and intervening when the human individual or group physiological operating states become elevated or aroused, thereby reaching a crisis state. The system and methods are designed to diffuse crisis operating states, returning the human individual or the group of individuals to the optimal or normal operating state. Three factors can affect human stress levels that, when elevated, result in crisis operating states: 1) Personal Factors, 2) Physical Environment Factors, and 3) Social Environment Factors. The disclosed technology herein can address Personal Factors that drive human stress levels. The technology disclosed in related application entitled "COMPUTER SYSTEM FOR GROUP CRISIS-STATE DETECTION AND INTERVENTION," filed on Jan. 4, 2021 having a Ser. No. 17/140,884, can address Physical Environment Factors and Social Environment Factors that drive human stress levels. The disclosed technologies can be combined to holistically address the totality of factors that drive human stress.

BACKGROUND

A crisis state may be defined as "a time of intense difficulty or danger." A crisis is an event or state that threatens the very stability of a person or group of persons convening for employment, education, community, social, recreational or other communal or living purposes. A crisis implies a situation where time is short, and an effective decision must be taken immediately. The crisis, if not intervened, perpetuates a sense of lack of control worsening the situation and thereby risking escalation and/or flawed human decision making. Crisis state intervention needs to be swift and effective with flexibility of interventions to meet individual and group differences and to meet further or prolonged shocks.

Three elements are generally attributed to a crisis state: (i) threat to the system, (ii) an element of surprise or unpreparedness, (iii) a short decision time to mitigate vs. exacerbate the situation which can lead to crisis escalation and the potential for irreversible damage via substandard decision making.

There remains a need for providing an individual, or group of individuals, with feedback to reduce individual or collective stress levels that contribute to negative behaviors that cause injury to individuals or the group. At an individual level, the previously unmet need is for smart wearable technology to enable crisis detection and intervention; at the household level, the previously unmet need is for smart home technology including hubs and controllers to enable crisis detection and intervention; and at the organizational or community level, the previously unmet need is for intelligent building technology to enable crisis detection and intervention.

SUMMARY

Crisis states—individual and group—can be effectively detected and intervened via an amalgam of hardware, software, sensors, and measurement of physical and behavioral indicators. At an individual level, smart wearable technology enables crisis detection and intervention; at the household level, smart home technology including hubs and controllers enables crisis detection and intervention; and at the organizational and/or community level, intelligent building technology enables crisis detection and intervention. The disclosed technology herein addresses human crisis states at the individual level with reference to the related technology in COMPUTER SYSTEM FOR GROUP CRISIS-STATE DETECTION AND INTERVENTION (Related Group Crisis State Detection/Intervention Application) that addresses human crisis states at the group (i.e., household, organizational and/or community) level.

In some embodiments, the disclosed technology provides a computer implemented method and system for detecting and intervening individual human crisis states. The system can use one or more user devices/input sensors to monitor, measure, and detect the operating state of a person or, in reference to the related technology in Related Group Crisis State Detection/Intervention Application, the collective operating state of a group of persons via obtaining measurements/values of physical (e.g., heartrate, blood flow, breathing, bodily secretions, muscle tension, body metabolism) and/or behavioral (e.g., movement, voice) indicators, or any combination thereof. These biometric values can be communicated from the user device(s) via the communication interface to the intervention system/server over a network (wired or wireless.) The intervention system/server can receive the values and send them to the information determiner that assesses if the user (or group in reference to the related technology in Related Group Crisis State Detection/Intervention Application) has achieved a crisis state by comparing the values it receives against a predetermined baseline or threshold value established using historical data. If the intervention determiner detects a crisis state (e.g., above the threshold), it can apply DUAL INTERVENTION methods—conscious and unconscious—to diffuse the crisis state and return the operating state to normal. (In this disclosed technology and the related disclosed technology in Related Group Crisis State Detection/Intervention Application, the term "unconscious" is utilized as shorthand to refer to complex, but familiar, psychological phenomenon whereby a good deal and perhaps most of mental life—as well as subtle changes in our surroundings—happen without our knowing much about it (UNCONCIOUS) or, if of our consciousness, it flies below our 'radar screen' (SUBCONSCIOUS). In other words, some of the interventions can be perceptible to the individual or group—e.g., CONSCIOUS INTERVENTIONS but other interventions—UNCONSICOUS INTERVENTIONS—can be either imperceptible or largely imperceptible to the individual or group.) If the intervention determiner does not detect a crisis state (i.e., below the threshold), no intervention occurs. Once the intervention determiner makes a crisis/no crisis determination, the data/values can be transmitted to the database for storage and subsequent processing and retrieval; and the intervention determiner can send data back to the user device(s) (and/or the building devices, in reference to the related disclosed technology in Related Group Crisis State Detection/Intervention Application) via the communication interface. The intervention determiner can use artificial intelligence and/or machine learning and/or other computational methods and algorithms to compare input data/values to historical values stored in the database to make determinations about the crisis state. Based on the assessment, the determiner may/may not implement an intervention.

In some embodiments, that are detailed in the related disclosed technology Related Group Crisis State Detection/Intervention Application, the system can obtain a measurement of parameters for the group. In some such embodiments, a crisis threshold can be obtained for the group based on one or two individuals in the group, not the entire group, while in other embodiments, a crisis threshold can be obtained for the group based on a sensory measurement of the group—taking a "group temperature" of the whole via the whole. For example, the average speed of walking (obtained, for example, by GPS sensors or accelerometers of a smart watch), rate and frequency components of speech and loudness of speech (obtained, for example, by smart cellphone microphones or smart speaker/microphones in a room), as well as facial expressions and excessive, exaggerated hand and/or other bodily movements (obtained, for example, by smart cellphone cameras or cameras in smart televisions in a room) can be measured. When all or most of these obtained parameters are materially elevated across the board (across all people) due to a threat (such as a culture shock due to a merger or acquisition, or the risk of unemployment) that triggered a group stress response, the related disclosed technology Related Group Crisis State Detection/Intervention Application can be used to detect the elevated operating state and provide interventions designed to modulate the physical environment and/or the social environment in which the group operates to de-escalate the group crisis state. In some embodiments, microphones and cameras can assess the group operating state, for example. In other embodiments, light detection and ranging lasers (e.g., LIDAR) or radar can be used by measuring human traffic speed. Personal Factors that affect human stress levels addressed herein can be addressed effectively with application of a direct intervention(s) aimed at the individual experiencing heightened stress. Addressing Social Environment Factors and Physical Environment Factors that affect human stress levels is not as clear-cut. As such, the related disclosed technology in Related Group Crisis State Detection/Intervention Application is focused entirely on that. Together the related technologies address the totality of human stress drivers. Specifically, the technology herein provides individuals with tools and technology to positively address the Personal Factors that affect human stress; and the technology in Related Group Crisis State Detection/Intervention Application provides organizations and communities with tools and technology to positively address Social Environment and Physical Environment Factors that drive human stress.

Accordingly, both disclosed technologies (herein and in the related technology Related Group Crisis State Detection/Intervention Application) apply a DUAL INTERVENTION that couples both imperceptible (or barely perceptible) interventions (called "unconscious" feedback herein) as well as perceptible interventions (called "conscious" feedback herein) to mitigate the individual or group stress response, respectively, restore the person's or persons' state to within their normal state range and corresponding healthy productivity and engagement levels associated with normal, non-elevated, operating states.

In some embodiments, the disclosed technology can provide a machine-learning computerized process that repeatedly, and substantially continuously, obtains data (symptoms) relevant to individual stress (e.g., an individual-crisis state), determines an appropriate intervention, activates that intervention, obtains data relevant to the effectiveness of the intervention, and "learns" which symptoms are most relevant to individual-stress determinations and which interventions are most effective in order to modify the system's future determinations and interventions based on the learning.

One or more of the preferred embodiments can include a system for crisis state detection and intervention of a user, the system including a computing device having one or more biometric sensors configured to detect biometric conditions of the user, and a transceiver configured to automatically transmit the biometric conditions in real-time. The system can also include a computing system having one or more processors, the computing system configured to receive, from the transceiver, the biometric conditions of the user, identify, using one or more models, a state of the user based on the biometric conditions of the user, wherein the one or more models are specific to the user having threshold indicators of different states of the user, the different states including a crisis state and a normal state of the user, generate, based on identifying that the user is in the crisis state, intervention instructions that are configured to be automatically executed by the computing device, the intervention instructions being configured to produce an action on the computing device to lower the user from the crisis state to the normal state, and transmit, to the computing device, the intervention instructions. The computing device can receive the intervention instructions from the computing system, and, in response to receiving the intervention instructions and without user permission or input at the time of receiving the intervention instructions, to automatically perform the intervention instructions on the computing device.

The preferred embodiments can include one or more of the following features. For example, the intervention instructions include automatically calling an emergency contact of the user without permission or user input from the user, the computing device being further configured to prompt, during an initial setup of the system, the user for (i) a phone number for each user-designated emergency contact and (ii) a call priority for each of the user-designated emergency contacts, in response to receiving the intervention instructions from the computing system, select a selected emergency contact from the user-designated emergency contacts based on the call priority for the selected emergency contact being greater than call priorities for each of the user-designated emergency contacts, and call, without user consent, the selected emergency contact using the phone number for the selected emergency contact. The computing system can also determine the normal state of the user based on one or more historic and present biometric conditions of the user being below a threshold value, wherein the historic and present biometric conditions include at least one of a heartrate, a blood flow, sweat, bodily movement, volume of voice, or speaking pace of the user. The computing system can identify the crisis state of the user based on determining that the biometric conditions of the user exceed a threshold value for biometric conditions of the user in the normal state. The intervention instructions can include providing audio, sensory, or physical feedback by the computing device to the user, wherein in response to receiving the intervention instructions from the computing system. The computing device can detect a presence of the user, select the audio, sensory, or physical feedback to provide to the user based on user preference and how much the biometric conditions of the user exceed a threshold value, wherein the audio, sensory, or physical feedback includes (i) a pulse that mimics a target heartrate of the user that is below the threshold value, (ii) a pulse that mimics a target breathing rate of the user that is below the threshold value, (iii) a sound that calms the user, or (iv) audio from an external environment that calms the user, and provide the selected audio, sensory or physical feedback to the user while the presence of the user is detected and until the biometric conditions of the user are less than the threshold value.

The computing device can provide audio from the external environment to the user based on determining a location of the user in the external environment, automatically activating an audio recorder of the computing device for a predetermined amount of time, and outputting, in a loop and until the detected biometric conditions of the user are less than the threshold value, the audio recorded by the audio recorded. The intervention instructions can include displaying, at a user interface display of the computing device, one or more interactive applications targeted at lowering the user from the crisis state to the normal state. The one or more interactive applications can include instructions prompting the user to perform actions that are intended to lower the user from the crisis state to the normal state, the actions including (i) playing a game with one or more other users, (ii) creating artwork with one or more other users, wherein the users contribute to a shared canvas that is displayed and updated in real-time at each computing device of the users, (iii) creating music using sounds from an external environment, (iv) performing an automated breathing exercise, or (v) taking a guided walk in a physical environment, wherein the guided walk is determined by the computing device and based on a current location of the user. The computing system can select an interactive application from the one or more interactive applications based on determining, using the one or more models, that the crisis state of the user is above a threshold indicator of a crisis state, and the computing device can, in response to receiving the intervention instructions from the computing system, display, at the user interface display of the computing device, the selected interactive application.

The computing device can also (i) execute the intervention instructions while the detected biometric conditions exceed a threshold value indicative that the user is operating in the crisis state and (ii) terminate the intervention instructions when the detected biometric conditions are lower than the threshold value. The computing system can also determine an efficacy score for executed intervention instructions in lowering the user from the crisis state to the normal state. The efficacy score can be based on an amount of time taken to lower the user from the crisis state to the normal state being less than a threshold value. The computing device can prompt, after execution of the intervention instructions, the user to provide input about an effectiveness of the executed intervention instructions, and transmit, to the computing system, the user feedback. The computing system can also receive, from the computing device, the user feedback, increase the efficacy score of the intervention instructions when the user feedback corresponds to the amount of time taken to lower the user from the crisis state to the normal state being less than the threshold value, and modify the generated intervention instructions based on the increased efficacy score, wherein the computing device can be configured to receive, from the computing system, intervention instructions having a higher efficacy score than intervention instructions having a lower efficacy score.

The computing system can also provide intervention instructions having an artificial intelligence (AI) coach, wherein the AI coach is displayed, at the computing device, and programmed to provide feedback to the user, the feedback being updated in real-time based on (i) the detected biometric conditions of the user or (ii) actions taken by the user on the user interface display and in response to prompts from one or more interactive applications. The feedback provided by the AI coach can include words of encouragement or guidance through one or more of the interactive applications. The computing system can transmit, to the computing device and based on determining that the crisis state of the user is below the threshold level, instructions causing the computing device to present, on the user interface display, one or more user-selectable interactive applications.

The intervention instructions can include one or more of (i) automatically calling an emergency contact of the user without consent from the user, (ii) displaying, at a user interface display of the computing device, one or more interactive applications targeted at lowering the user from the crisis state to the normal state, and (iii) providing audio, sensory, or physical feedback by the computing device to the user. The intervention instructions can include two or more of (i) automatically calling an emergency contact of the user without consent from the user, (ii) displaying, at a user interface display of the computing device, one or more interactive applications targeted at lowering the user from the crisis state to the normal state, and (iii) providing audio, sensory, or physical feedback by the computing device to the user. The intervention instructions can also include (i) automatically calling an emergency contact of the user without consent from the user, (ii) displaying, at a user interface display of the computing device, one or more interactive applications targeted at lowering the user from the crisis state to the normal state, and (iii) providing audio, sensory, or physical feedback by the computing device to the user. The intervention instructions can cause the computing device to perform at least one of unconscious intervention or conscious intervention on the user, the unconscious intervention causing a sensory change for the user and the conscious intervention causing a mental change for the user. Moreover, in response to receiving the intervention instructions from the computing system, the computing device can lock, for a predetermined amount of time and without user permission or input, the user interface display when the one or more interactive applications are displayed, wherein locking the user interface display prevents the user from exiting the one or more interactive applications that are displayed, prompt the user to perform one or more actions in the one or more interactive applications that are displayed on the user interface display, and unlock the user interface display based on (i) the user completing the one or more actions, (ii) the predetermined amount of time exceeding a threshold amount of time, or (iii) the detected biometric conditions of the user being lower than a threshold level. The computing system can also train on the one or more models that are specific to the user based on the detected conditions of the user, executed intervention instructions, an amount of time taken to lower the user from the crisis state to the normal state, and an efficacy score of the executed intervention instructions.

One or more advantages can be recognized from the disclosure herein. Human crises states—the human stress response—is an insidious invader to human health that sneaks in and takes over hundreds of different mind and body pathways if we aren't vigilant. Bringing an individual (or group) down from an elevated state of physiological distress can require a full-on attack that involves constant control over human HEADS (COGNITION) and human BODIES (SENSES—PHYSIOLOGY). The disclosed technology can ambush individual human crisis states via a multiplicity of UNCONSCIOUS and CONSCIOUS (e.g., DUAL) interventions delivered IMMEDIATELY through myriad user devices (e.g., wearables and non-wearables) at an ongoing basis to stop rising physiological stress levels and return the user to their normal operating state. Multiple devices can be used in the system because, depending on where the devices are placed on the human body and/or the role the devices play in our lives, each device can allow for sensing different physiological attributes that drive the human stress response. In addition, these user devices—wearable and not—allow for many different types of interventions—and combinations of interventions—both CONSCIOUS and UNCONSCIOUS. The DUAL INTERVENTION SYSTEM can provide for enhanced system efficacy. UNCONSCIOUS interventions can be largely imperceptible and include SENSORY-TYPE interventions—sight, sound, taste, touch, smell (and potentially other senses such as neuron sensors that sense movement to control balance and the tilt of the head. Specific kinesthetic receptors exist for detecting stretching in muscles and tendons. Other receptors detect levels of oxygen in certain arteries of the bloodstream). The sensing organs associated with each sense send information to the brain to help us understand and perceive the world around us. The UNCONSCIOUS INTERVENTIONS can directly impact human physiology—grabbing hold of a runaway human stress response—by physically diffusing a threat to the system perceived by the sense organs of the human body. For example, the sensory intervention can be a haptic pulse that is paced slower than the human heart rate or an aroma that has a proven calming effect on the human body. These UNCONSCIOUS INTERVENTIONS can be advantageous because the intervention can be implemented without distracting the user (e.g., preventing the user from carrying on with a current task) or inducing a sense of overwhelm by forcing the user to cognitively focus on their body in the midst of an out-of-control human stress response. CONSICOUS INTERVENTIONS have a different job—they can grab hold of the individual's brain/cognition while in the midst of a stress response by offering an IMMEDIATE DISTRACTING ACTIVITY. Human lives are controlled by three things: Thoughts, Emotions, and Actions. Humans cannot change their emotions directly. Changing our thoughts can be difficult. We can change our actions to consciously disrupt a runaway crisis state. CONSCOUS INTERVENTION activities described herein can be software applications that consume and engage the user offering another, different form of IMMEDIATE intervention. The app collection can be comprised of five app sub-collections each aligned with a different proven crisis-mitigating area or theme (e.g., Creative Release, Physical Release, Verbal Release, Change Mindset, Change Environment). Just like there are multiple user devices and device combinations enabled by the system to sense rising stress levels and intervene, there can also be many different immediate intervention types made possible by the five broad types of sense-influencing UNCONCIOUS interventions and five broad families of cognitive-influencing CONSCOUS interventions. All of the CONSCIOUS interventions can activate the mesolimbic pathway (e.g., "the pleasure center") of the brain. Positive emotional states arise from using our software by influencing a core neurophysiological system (related to valence—a pleasure-displeasure continuum) that shifts user's affective state from displeasure to pleasure. The interventions delivered and described herein can be IMMEDIATE by design. Individuals in a crisis state need IMMEDIATE interventions to help them manage the critical MOMENT of heightened physiological arousal. The interventions can be centered on swift, effective, IMMEDIATE de-escalation techniques, which contrast conventional approaches that offer delayed support (e.g., not in the moment of crisis such as a therapy session or cognitive behavioral working session), inappropriate support (e.g., meditation or yoga that require a brain under control), or no support (e.g., failure to attract certain audiences due to embedded sub-cultural beliefs and norms that preclude engagement.)

Another advantage of the system is that it can be flexible and scalable. Although the technical design and intention is to bombard a crisis state from every angle in real-time to bring about swift reduction and return to the user's normal—non crisis—operating state, not every user may require the same level of crisis support. For example, a teen with social phobia may need just two devices to control the frequency and severity of physiological crises states; but a highly traumatized individual with severe PTSD may need several devices to manage and de-escalate from frequent and/or ongoing crisis operating states.

One or more other advantages can be realized from the disclosed technology. For example, one feature of a software application included in the Verbal Release sub-collection of the disclosed technology can assist an individual in responding to a crisis state without the individual's engagement. Where the individual's stress response is activated, the individual may not be able to make appropriate decisions to reduce him/herself from the crisis state, potentially leading to further harm or, worse, a catastrophic situation with an irreversible outcome. The disclosed technology can automatically intervene and provide the individual with immediate sensory feedback (unconscious) intervention and instructions and/or guidance (conscious intervention) designed to swiftly lower the individual from the crisis state. For example, the disclosed technology can call a family member, or a trusted friend or coach to alert them that the individual is in a severe physiological crisis state. The disclosed technology can call the supporter without permission from the individual and can override any attempt by the individual to prevent the intervention. And a sensory-type intervention to the individual while in the crisis state can provide an unconscious intervention that unobtrusively yet swiftly lowers the individual from the crisis state.

Moreover, the disclosed technology can predict/determine when the individual is escalating toward a full-on crisis state to intervene with a swift, effective intervention designed to return them to their normal state. Such preventative measures can assist the individual in developing better habits, best practices and body awareness that are the cornerstone to crisis state self-management. The disclosed technology can also be advantageous because it provides for immediate intervention when the individual enters the crisis state. Because there is no delay between intervention and entering the crisis state, the individual can more quickly and effectively de-escalate from an elevated state of physiological arousal. Even more so, the inclusion of automatic unconscious sense-based interventions provided by one or more sensors in the user device(s), coupled with a conscious intervention at the user device(s), such as prompting the individual to interact with one of the crisis-state mitigating apps in the app collection, can assist the individual in lowering from the crisis state faster. Providing the individual with interactive applications can provide for teaching the individual how to cope with crisis states and/or high levels of stress by developing body awareness, best practices, and daily habits so that in the future, the individual can circumvent crisis states that are avoidable and/or, when not avoidable, manage them more effectively through improved insight and skills. Additional and/or other advantages of the disclosed technology are apparent based on the disclosure herein.

BRIEF DESCRIPTION OF THE DRAWINGS

FIG. 1 is a list of three factors that affect human stress levels.

FIG. 7A is a block diagram of a process 400 for determining the user(s) baseline operating state, according to some embodiments of the disclosed technology.

FIG. 8 is a block diagram of a dual-intervention system 500, according to some embodiments of the disclosed technology.

FIG. 9 is a block diagram of an unconscious intervention system and method 600, according to some embodiments of the disclosed technology.

FIG. 10 is a block diagram of a conscious intervention system and method 700, according to some embodiments of the disclosed technology.

FIGS. 16-21 are exemplary user interfaces of the intervention system described herein.

FIG. 23 is a block diagram of a simplified exemplary system 802 for implementing the present invention that, in contrast to system 801 of FIG. 8A, includes much or all of the functionality of conventional general-purpose computing system 800 instead implemented in a smart-phone system of wearable devices in one or more user device system(s) 210, according to some embodiments of the disclosed technology.

FIG. 24A is a block diagram of a process 901 for dispensing programs into a personal computer 990 or similar information-processing device, for example, a new user device being purchased by its initial user.

FIG. 24B is a block diagram of a process 902 for dispensing programs into a personal computer 990 or similar information-processing device.

DESCRIPTION OF PREFERRED EMBODIMENTS

Figure 2:
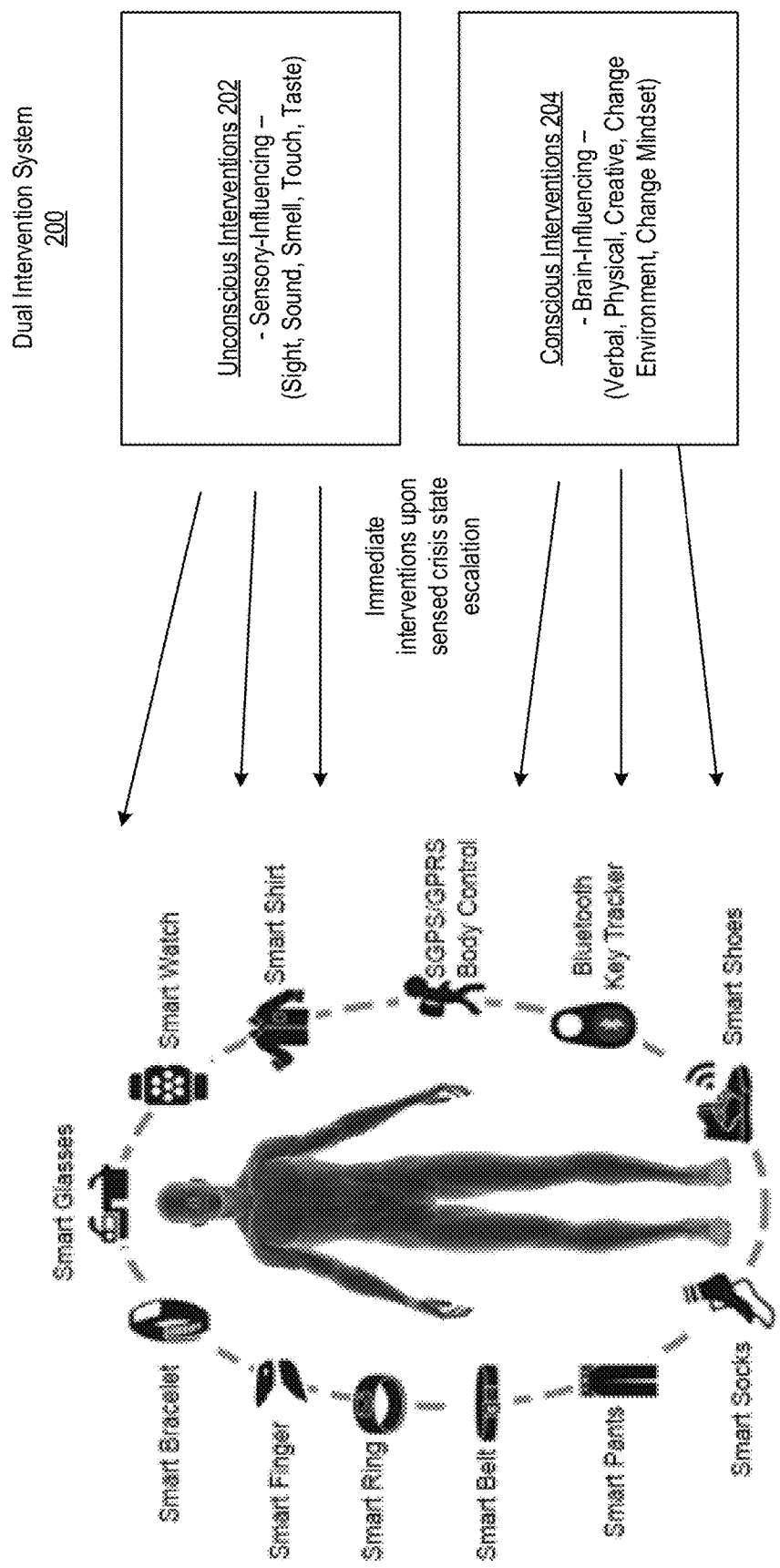
FIG. 2 is an overview of a dual intervention system described herein.

Although the following detailed description contains many specifics for the purpose of illustration, a person of ordinary skill in the art can appreciate that many variations and alterations to the following details are within the scope of the disclosed technology. Specific examples are used to illustrate particular embodiments; however, the disclosed technology described in the claims is not intended to be limited to only these examples, but rather includes the full scope of the attached claims. Accordingly, the following preferred embodiments of the disclosed technology are set forth without any loss of generality to, and without imposing limitations upon the claimed disclosed technology. Further, in the following detailed description of the preferred embodiments, reference is made to the accompanying drawings that form a part hereof, and in which are shown by way of illustration specific embodiments in which the disclosed technology may be practiced. It is understood that other embodiments may be utilized, and structural changes may be made without departing from the scope of the disclosed technology. The embodiments shown in the Figures and described here may include features that are not included in all specific embodiments. A particular embodiment may include only a subset of all of the features described, or a particular embodiment may include all of the features described.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Crisis states are precipitated by the human stress response. Stress is a biological and physiological response experienced on encountering a threat that one may not have the resources to deal with. A stressor is the stimulus (or threat) that causes stress. Sudden and severe stress generally produces: Increase in heart rate and strength in heartbeat; Shifts in blood flow; Changes in speed and depth of breathing (lungs dilate); Increase in sweating; Increase in bodily movement; Vocal distress; Decrease in digestive activity; and/or Liver releases glucose for energy.

The human body determines whether a situation is stressful. The decision can be made based on sensory input and processing, and on stored memories. If the situation is judged as being stressful, the hypothalamus is activated. The hypothalamus in the brain oversees the stress response. When a stress response is triggered, it sends signals to two other structures: the pituitary gland and the adrenal medulla.

When the pituitary gland is stimulated, it secrets adrenocorticotropic hormone (ACTH) which stimulates the adrenal glands to produce the hormone corticosteroid. Cortisol enables the body to maintain steady supplies of blood sugar to help a person cope with the stressor and return to normal.

The hypothalamus also activates the adrenal medulla, which is part of the autonomic nervous system (ANS.) The ANS is part of the peripheral nervous system that acts as a control system, maintaining homeostasis in the body. The activities are performed without conscious control.

The adrenal medulla secretes the hormone adrenaline. This hormone gets the body ready for a fight or flight response, which is ascertained by measuring one or more of the biological and/or physiological reactions detailed above.

Adrenaline leads to the arousal of the sympathetic nervous system that creates changes to the body thereby leading to a "crisis state." There is considerable variation in the level and type of hormones released by different people in response to different stressors, thereby warranting a computer-driven, multisensory, immediate, conscious and unconscious approach to crisis state detection and intervention.

There are several types of situations that can be considered human crisis situations and/or lead to crisis operating states in humans. People in these situations or suffering from these conditions can feel accelerated and/or elevated states of arousal that includes agitation, restlessness, fatigue, muscle tension, sleep disturbances, panic attacks and more. A crisis state can cloud human judgement, feel highly uncomfortable and stressful, and induce erratic, unanticipated and/or unexpected behaviors. These behaviors can have detrimental or deadly consequences for oneself and others; one's life and livelihood and that of others. Human crisis-state drivers can include: Family Disruption or Disturbance—e.g., divorce, death, accident; Natural Disasters—e.g., flooding, tornadoes, any situation created by a weather disorder; Assaults on Humanity—e.g., acts of terrorism, mass shootings, robbery, prolonged bullying; Suicide; Economic Changes—e.g., loss of job, medical bills, theft of identity or wallet; Life Events—e.g., death of a loved one, birth of a child, any disturbance to daily activities; Mental Disease or Disorder—e.g., anxiety disorders, bipolar disorder; and/or Organizational Changes—e.g., culture shock due to merger, risk of unemployment, friction inside the community.

Although humans tend to think of stress and anxiety as an individual phenomenon. group stress is also a very real—but underrecognized—phenomenon. Specifically, human adaptation strategies to difficult and harmful stressors can be individual in nature (i.e., each individual thinks and acts independently) or they can be "collective" in nature meaning that individuals think and behave as a group instead of as independently thinking and behaving individuals that comprise the group—in other words, making decisions based in part on the behavior/choices of others. In high stress environments, these collective coping behaviors can be particularly damaging, and, in some instances, can include diffusion of personal responsibility, blind obedience to authority, uncritical conformity to group norms, and passive tolerance of damaging or cruel behaviors through inaction or indifference.

Collective stress and/or the collective stress response emerges as a response to two types of "threats": (1) an attempt to adapt to an environment that is imperfect or experiencing tremendous change and transformation (2) friction inside the community, Recall that three factors affect human stress levels: personal factors, physical environment factors, and social environment factors. The interplay among them is powerful. That is why we created two related systems: the system herein designed to positively influence the PERSONAL FACTORS that affect human stress levels, and the related disclosed technology designed to positively influence the SOCIAL ENVIRONMENT FACTORS and PHYSICAL ENVIRONMENT FACTORS that affect human stress levels.

Both systems incorporate the same fundamental advantages (e.g., IMMEDITATE DUAL INTERVENTIONS—CONSCIOUS and UNCONSCIOUS; multiple user devices; multiple, diverse, and ongoing interventions for a real-time optimally effective crisis state onslaught.) The disclosed technology herein is centered on addressing the PERSONAL drivers to human stress.

In the description that follows, the disclosed invention can be described with reference to acts and symbolic representations of operations that are performed by software executing in one or more computers or information processors (a computer system), or as simply systems or processes/methods. As such, it will be understood that such acts and operations, which are at times referred to as being computer-executed, include the manipulation by a processing unit of the computer system of electrical signals representing data in a structured form. This manipulation transforms the data or maintains it at locations in the memory system(s) of the computer system, which reconfigures or otherwise alters the operation of the computer system in a manner well understood by those skilled in the art. The data structures where data is maintained are physical locations of the memory that have particular properties defined by the format of the data. However, while the disclosed technology is being described in the foregoing context, it is not meant to be limiting as those of skill in the art will appreciate that various of the acts and operation described hereinafter may also be implemented in hardware (electronic circuitry).

FIG. 1 lists the three drivers of human stress. The PERSONAL Factor is addressed by the disclosed technology herein, while the SOCIAL ENVIORNMENT and PHYSICAL ENVIRONMENT Factors are addressed in related disclosed technology Related Group Crisis State Detection/Intervention Application.

FIG. 2 is a visual depiction of the overarching system structure and approach to individual crisis state intervention (e.g., dual intervention system 200). Human crises states—the human stress response—is an insidious invader to human health that sneaks in and takes over hundreds of different mind and body pathways if we aren't vigilant. Bringing an individual (or group) down from an elevated state of physiological distress requires a full-on attack that involves constant control over human HEADS (COGNITION) and human BODIES (SENSES—PHYSIOLOGY). The disclosed technology is designed to ambush individual human crisis states via a multiplicity of UNCONSCIOUS and CONSCIOUS (e.g., DUAL) interventions delivered IMMEDIATELY through myriad user devices (e.g., wearables and non-wearables) at an ongoing basis to stop rising physiological stress levels and return the user to their normal operating state. Multiple devices are central to the system because, depending on where the devices are placed on the human body and/or the role the devices play in our lives, each device can allow for sensing different physiological attributes that drive the human stress response. In addition, these user devices—wearable and not—allow for many different types of interventions—and combinations of interventions—both CONSCIOUS and UNCONSCIOUS. The DUAL INTERVENTION SYSTEM 200 is key to the system efficacy. UNCONSCIOUS interventions 202 are largely imperceptible and include SENSORY-TYPE interventions—sight, sound, taste, touch, smell (and potentially other senses such as neuron sensors that sense movement to control balance and the tilt of the head. Specific kinesthetic receptors exist for detecting stretching in muscles and tendons. Other receptors detect levels of oxygen in certain arteries of the bloodstream.) The sensing organs associated with each sense send information to the brain to help us understand and perceive the world around us. The UNCONSCIOUS INTERVENTIONS directly impact human physiology—grabbing hold of a runaway human stress response—by physically diffusing a threat to the system perceived by the sense organs of the human body. For example, the sensory intervention could be a haptic pulse that is paced slower than the human heart rate or an aroma that has a proven calming effect on the human body. These UNCONSCIOUS INTERVENTIONS can be implemented without distracting the user (i.e., preventing them from carrying on with a current task) or inducing a sense of overwhelm by forcing the user to cognitively focus on their body in the midst of an out-of-control human stress response. CONSICOUS INTERVENTIONS 204 are designed to grab hold of the individual's brain/cognition while in the midst of a stress response by offering an IMMEDIATE DISTRACTING ACTIVITY. Human lives are controlled by three things: Thoughts, Emotions, and Actions. Humans cannot change their emotions directly. Changing our thoughts is incredibly difficult. We CAN change our actions to consciously disrupt a runaway crisis state. The CONSCOUS INTERVENTION activities can be software applications that consume and engage the user offering another, different form of IMMEDIATE intervention. The app collection, as described herein, is comprised of five app sub-collections each aligned with a different proven crisis-mitigating area or theme (e.g., Creative Release, Physical Release, Verbal Release, Change Mindset, Change Environment.) Just like there are multiple user devices and device combinations enabled by the system to sense rising stress levels and intervene, there are also potentially hundreds and thousands of immediate intervention types made possible by the five broad types of sense-influencing UNCONCIOUS interventions and five broad families of cognitive-influencing CONSCOUS interventions. The CONSCOUS interventions 204 activate the mesolimbic pathway (aka "the pleasure center") of the brain. Positive emotional states arise from using our software by influencing a core neurophysiological system (related to valence—a pleasure-displeasure continuum) that shifts user's affective state from displeasure to pleasure. All of the interventions delivered are IMMEDIATE by design. Individuals in a crisis state need IMMEDIATE interventions to help them manage the critical MOMENT of heightened physiological arousal. The interventions are centered on swift, effective, IMMEDIATE de-escalation techniques, which contrast the typical technologies of the day that offer delayed support (e.g., not in the moment of crisis such as a therapy session or cognitive behavioral working session), inappropriate support (e.g., meditation or yoga that require a brain under control), or no support (e.g., failure to attract certain audiences due to embedded sub-cultural beliefs and norms that preclude engagement.) The system can also be flexible and scalable. Although the technical design and intention is to bombard a crisis state from every angle at every needed moment in time to bring about swift reduction and return to the user's normal—non crisis—operating state, not every user may require the same level of crisis support. For example, a teen with social phobia may need just two devices to control the frequency and severity of physiological crises states; but a highly traumatized individual with severe PTSD may need several devices to manage and de-escalate from frequent and/or ongoing crisis operating states.

In other words, FIG. 2 represents an exemplified and non-limiting overview of the dual intervention system—conscious and unconscious. These dual interventions address the problem of operating state crisis from different angles and apply distinctive solutions and approaches thereby compounding the impact of the system and the efficacy for the user or, in the case of the related disclosed technology, group of users. The dual intervention system is actuated only when the user (or group) is deemed by the intervention system/server to have exceeded their threshold level. Without exception, the system automatically actuates the unconscious intervention, if the user's biometric values exceed the threshold. To actuate the unconscious intervention, the intervention system/server sends data via the communication interface over the network to the user device(s)/output device(s) instructing it to emit sensory feedback (taste, touch, sight, sound, smell) calibrated to the physical or biological indicator under measure. The process is entirely unconscious to the user and is designed to not distract or disrupt their current activity. Instead, it is designed to unconsciously and unobtrusively modulate and mitigate the crisis state, returning the user to a normal state.

Unlike the unconscious intervention system, the conscious intervention system has an element of user or administrator control. Specifically, the user or administrator, acting on behalf of the user (such as a parent or guardian), determines, at initial system set-up, if they prefer the conscious intervention to be user-directed or system-directed. If the user or administrator chooses to control the conscious intervention when the threshold level is reached, the user or administrator will be notified by the user device(s)/output device(s) and asked to select one of many conscious interventions/apps from the app collection. If the user chooses the system to control the conscious intervention automatically when the threshold level is reached, the system will make an app intervention recommendation from the collection based on prior learning of efficacy under similar circumstances.

Even if the person (or group of persons) relies on system-generated recommendations for software application intervention, the user (or administrator) can always override the system to self-select intervention applications.

Figure 3:
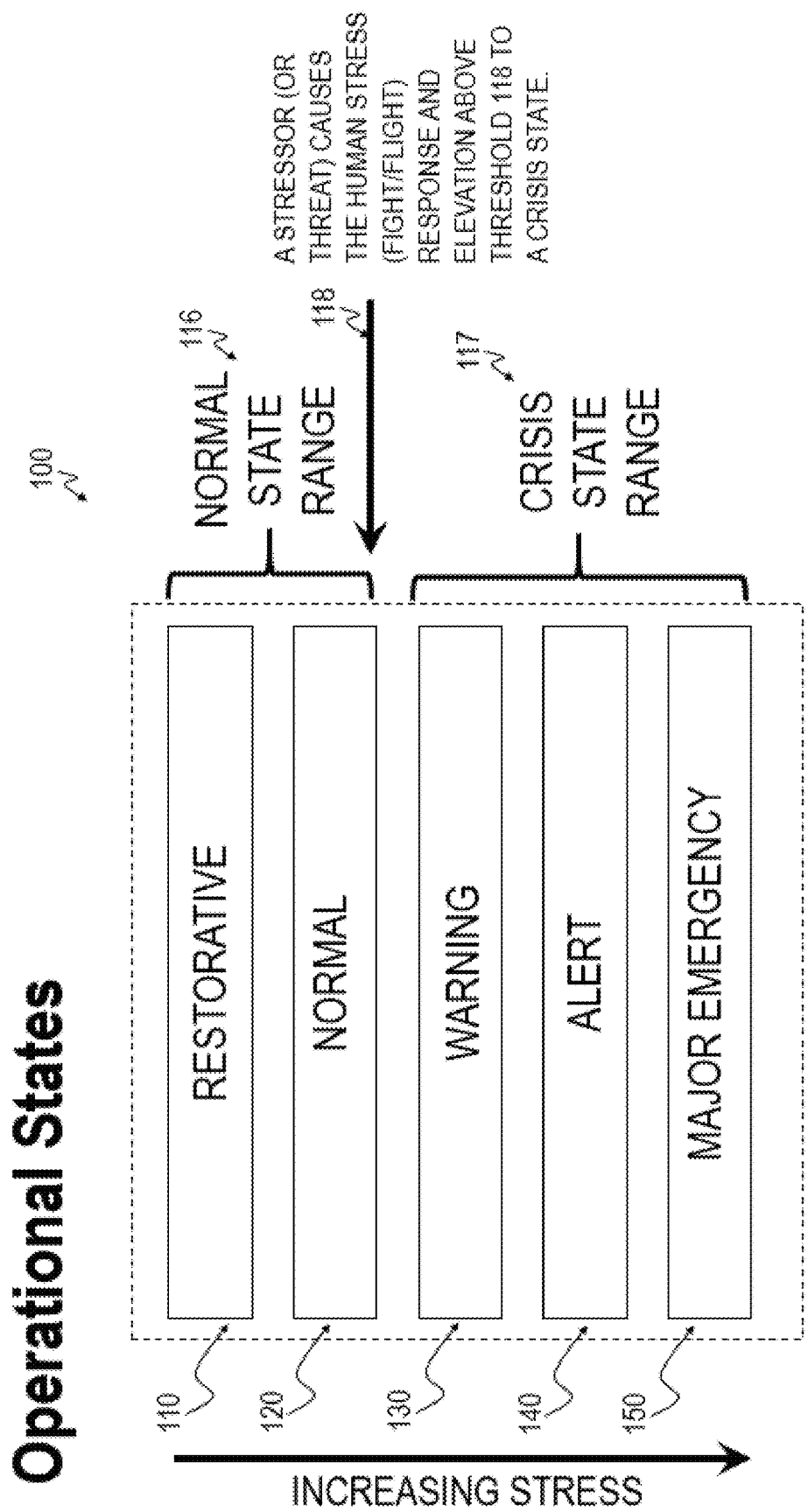
FIG. 3 is a process for determining operational states.

FIG. 3 is a block diagram that represents a categorization 100 of operating states, according to some embodiments of the disclosed technology. In some embodiments, categorization 100 includes restorative state 110 (representing the state whereby an individual or group is capable of restoring and/or attaining restorative benefits; a relaxed, calm state of being), and normal state 120 (representing the regular, natural state that conforms with the median or average standard of the individual or group; the baseline), wherein, at a high level, restorative state 110, and normal state 120 are considered to be the "normal state range" 116, in that the person or group of persons are coping well in their environment; their thinking and behavior is reasonable, logical, and abstract. In some embodiments, categorization 100 also includes warning state 130 (representing the state immediately following a threat that triggers the human stress response; agitation results, indicating a possible or impending danger, problem, or other unpleasant situation), alert state 140 (representing a state of escalation and acceleration; agitation is progressing to aggression), and major-emergency state 150 (representing the peak crisis state where thinking and behavior are concrete, illogical and unfocused; the risk of outburst is high), wherein warning state 130, alert state 140, and major-emergency state 150 form a range of crisis states 117 that would benefit from the detection and intervention systems and methods of the disclosed technology. These states can be determined by the computing system 158 based on one or more conditions of the user 152 that are sensed by the wearable device 156 and/or the mobile device 154.

As depicted in FIG. 3, the five operating states include: RESTORATIVE, NORMAL, WARNING, ALERT, and MAJOR EMERGENCY. These states further combine into two higher order operating states. Restorative and Normal combine to form the NORMAL STATE RANGE, and Warning, Alert, and Major Emergency combine to form the CRISIS STATE. The crisis state is characterized as such because, in this state, the person (or group of persons) are experiencing accelerated and/or elevated states of arousal brought on by a stressor or stimulus (or threat) that caused the human stress response or flight/flight response. Since a crisis state can induce erratic, unanticipated and/or unexpected behaviors, the current technology is designed to intervene as soon as a person or group of persons transitions from their baseline NORMAL STATE to their CRISIS STATE. By design, the computer-implemented system does not intervene with a crisis intervention when the person (or persons) are in their NORMAL STATE RANGE as there is no risk of damage or danger to self or others. The system may, however, intervene with a positive—conscious or unconscious—reinforcement or reward if the person (or persons) are able to sustain a normal state range for an extended period of time.

Figure 4:
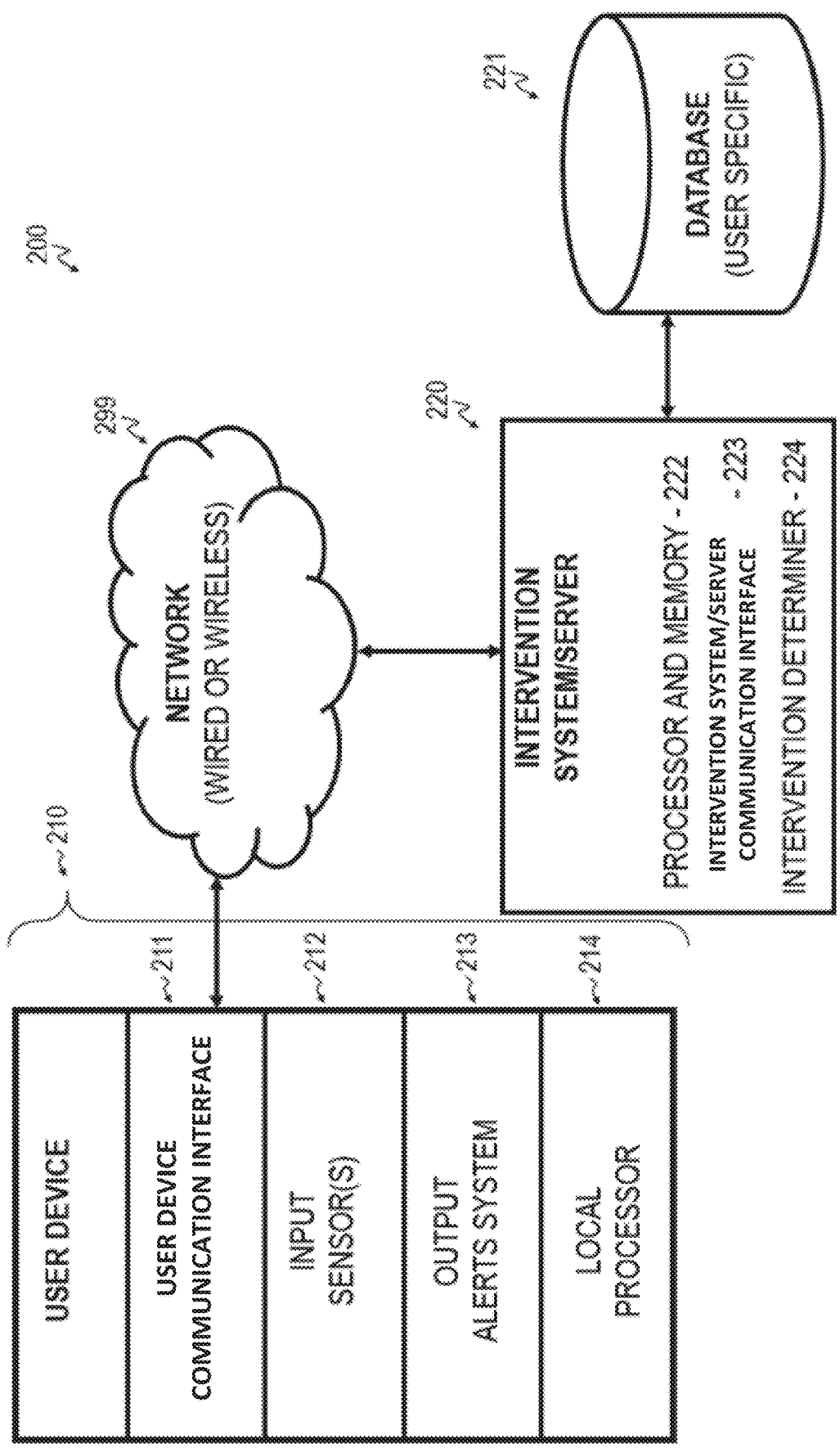
FIG. 4 is a block diagram of a structure 200 involving the detection and intervention of a human crisis state, when this technology is utilized at the individual level, according to some embodiments of the disclosed technology.

FIG. 4 is a block diagram of a system 200 involving the detection and intervention of a human crisis state, when this technology is utilized at the individual level, according to some embodiments of the disclosed technology. In some embodiments, system 200 includes a user device 210 and a server system 220 that communicate with each other via network 299 (which includes wired and/or wireless communications). In some embodiments, user device 210 includes a user device communications interface 211 (such as a cellular phone interface that sends data to and receives data from server system 220), and one or more input sensors 212. In some embodiments, input sensors 212 include sensors for heart rate, perspiration, skin resistance, physical movement and/or orientation, speed and depth of breathing, blood flow, vocal changes, muscle tension, metabolic responses, and the like. In some embodiments, server system 220 includes one or more databases 221 that store past symptoms and responses and thresholds and proposed or predetermined responses for sets of symptoms. In some embodiments, user device 210 also includes an output and/or alert system 213, while in other embodiments, output and/or alert system 213 is one or more separate device (for example, such as a wireless earphone that provides audio feedback to the user, a haptic vibrating wristband or necklace pendant that provides touch feedback to the user, LEDs mounted on eyeglasses or a wristband that provide visual feedback to the user, scent, perfume, and/or odor emitters (e.g., in some embodiments, one or more small heating elements coupled to a set of solid perfume or scented wax bars (or the like) located on a smart wristband worn by a user as conditionally activated scent-emitters in wirelessly-connected room air "freshener(s)" coupled to an "internet of things" (IoTs), wherein they are activated by heat to emit a predetermined perfume (odor) that provide smell feedback to the group of users within a specific physical environment, electrodes (that touch the users skin such as via ear clips, earphones (e.g., AIRPOD®-like devices optionally enhanced to includes electrodes for electrical stimulation), wristbands, leg bands, arm or chest patches, etc.) and electrical signal generators that provide subtle (imperceptible) electrical signals or explicit palpable gentle electrical shocks to the user (such as transcutaneous electrical nerve stimulation ("TENS")-like signals), neuro muscular electrical stimulation ("NMES"), repetitive transcranial magnetic stimulation ("rTMS"), transcranial direct current stimulation ("tDCS") and/or the like) that receives alert signals from the user's cell phone that serves as the user device communications interface 211. In some embodiments, the one or more input sensors 212 are also in a separate device, such as a smart watch, that uses the user's cell phone that serves as the user device communications interface 211. Thus, in some embodiments, user device 210 is implemented as a multi-part system of wearable device portions that include one or more wearable sensors 212, one or more wearable alert/output devices 213, and one or more user device communications interfaces 211, wherein these communicate data among themselves and to and from server 220. In some embodiments, one or more portions of, or the entirety of, the intervention server 220 is implemented as software that executes within a user's personal computing device (such as a smart cell phone), and the communications interface to a wired or wireless network is eliminated for such functions. In reference to the related technology in Related Group Crisis State Detection/Intervention, a smart home hub (or smart speaker that operates as such) can serve as the user device communication interface 211 between one or more input sensors 212, such as a camera or microphone and output alert/output devices 213 that comprise smart home, building and IoT-enabled devices and systems, including entertainment systems, smart sensors on thermostats, light-bulbs, outlets and switches, door locks and sensors, security system, fans, window treatments/coverings, and the intervention system/server 220. In some embodiments, one or more portions of, or the entirety of, the intervention server 220 is implemented as software the executes within the smart hub which also serves as the user device communications interface 211.

The disclosed technology provides a computer-implemented method and system 200 for detecting and intervening human crisis states—individual, as outlined and described herein. The system 200 is comprised of multiple components, connected by a computer network which may be wired or wireless. The core of the system is the intervention system/server 220 which can be a cloud-based server, the same server as the user device (e.g., a program running and using a database within the user's device), or another server. Intervention system/server 220 has a processor, memory and a communication interface that allows intervention system/server 220 to transmit data and values to/from other components in the system 200. Importantly, the intervention system/server 220 also includes the intervention determiner, which receives data from the user device (s) via the network and processes it, using one or more computational methods, to determine whether an intervention is warranted, and to initiate the intervention if that is warranted.

The intervention system/server also transmits data to and from the database(s) that capture and store user-specific data and values. The database(s) are part of the overarching system and function primarily for data storage and retrieval of individual and group information and values.

Another component of the system are the user device(s) 210, such as shown in FIG. 4. In some embodiments, these devices 210 are multifunctional. They have a user device communication interface 211 that allows them to communicate with the intervention system/server 220 and database(s) 221 via the network. The user devices also operate as input sensor(s) obtaining user biometric values to assist with determining the operating state of the user. In addition, the user device(s) function as output device(s), alerting the user that the crisis threshold 118 has been surpassed which triggers the delivery of a crisis state intervention—conscious, unconscious or both—depending on the settings established by the user or administrator. This alert system and the conscious and unconscious interventions are the mechanisms that diffuse crisis states and stop crisis escalation to circumvent catastrophic crisis-driven outcomes.

In some embodiments, the system 200 utilizes one or more user devices/input sensors 212 to monitor, measure, and detect the operating state of a person, via obtaining measurements/values of physical (e.g., heartrate, blood flow, breathing, bodily secretions, muscle tension, body metabolism) and/or behavioral (e.g., movement, voice) indicators, or any combination thereof. These biometric values obtained by sensors 212 are communicated from the user device(s) via the communication interface to the intervention system/server 220 over a network 299 (wired and/or wireless). The intervention system/server 220 receives the values and sends them to the internal intervention determiner 224 (in some embodiments, a program running in processor-memory 222) that assesses whether the user has achieved a crisis state by comparing the values it receives against a predetermined baseline or threshold value established using historical data and stored in database 221. If the intervention determiner 224 detects a crisis state 117 (e.g., above the threshold 118), intervention determiner 224 will apply DUAL INTERVENTION methods—both methods referred to herein as "conscious" (methods providing user feedback that is readily perceptible by the user, and unconscious (providing feedback that is barely perceptible or not perceptible by the user—to diffuse the crisis state 117 and return the operating state to a normal state range 116. If the intervention determiner 224 does not detect a crisis state 117 (e.g., a state below the threshold 118), no intervention occurs.

Once the intervention determiner 224 makes a crisis/no crisis determination, the data are transmitted to the database 221 for storage and subsequent processing and retrieval; and 220 sends data back to the user device(s) via the intervention system/server communication interface 223. In some embodiments, the intervention determiner 224 utilizes artificial intelligence and/or machine learning and/or other computational methods and algorithms to compare input data/values from the user device(s) 210 to historical values stored in the database 221 to make its determination. Based on the assessment, the intervention determiner 224 may/may not implement an intervention.

In some embodiments, the present technology imparts no crisis intervention, alert or action when a person's operational state is determined to be within their non-crisis, normal state range 116 (which includes both normal state 120 and restorative state 110)—a range 116 that is determined by the intervention determiner 224 at an individual level by an initial computational training phase 400 that is calibrated and updated on an ongoing basis—in some embodiments, by method 1000 via systematic processes utilizing artificial intelligence, machine learning, and/or other computational methods and algorithms, as well as user-driven or administrator-driven readings and refinements. The present technology may impart positive feedback in the form of an unconscious sensory affirmation (including sight, sound, smell, taste, touch) to signal a "job well done" to the user if operating in a sustained normal state range 116.

When the intervention system/server detects a transition from the normal state range 116 (which includes normal state 120 and restorative state 110) across threshold 118 to a state in the crisis state range 117 (which includes alert state 130, warning state 140 and major emergency state 150), the intervention system/server 220 communicates via the network 299 to the user device(s) 210, transmitting data that triggers, in some embodiments, the alert system 213 to activate the DUAL INTERVENTION method:

(i) The first intervention emitted by the user device(s) is UNCONSCIOUS (barely or not perceptible) to the user and involves one or more sensory interventions (sight, smell, hearing, taste, touch and/or electrical stimulation) that can be calibrated to the person or the person's physical and/or behavioral indicators and current individual operating state and is designed to unconsciously modulate the crisis state and the related physical and/or behavioral responses via direct sensory feedback delivered through the user device(s), which, in some embodiments, may or may not be wearable. Humans pay rare attention to inherent bodily processes—breathing rate, heart rate, perspiration. Providing feedback that mimics existing bodily processes through external devices—albeit at a slower rate or lower intensity than the actual rate or intensity occurring in the midst of a crisis state—is a largely unconscious intervention that modulates human's physiology by providing steady, sure feedback. The primary benefit and characteristic of unconscious interventions is that they work in mitigating crisis states without distracting or overwhelming the user—i.e., the user doesn't have to DO anything or STOP anything.

(ii) The second, concurrent intervention, delivered through the same or different user device (which may or may not be wearable), is CONSCIOUS to the person and involves an alert and/or prompt inviting the individual to engage with and/or deploy a recommended app from one of several themed app sub-collections aligned with proven stress mitigating areas and based on prior system application and efficacy.

Figure 5:
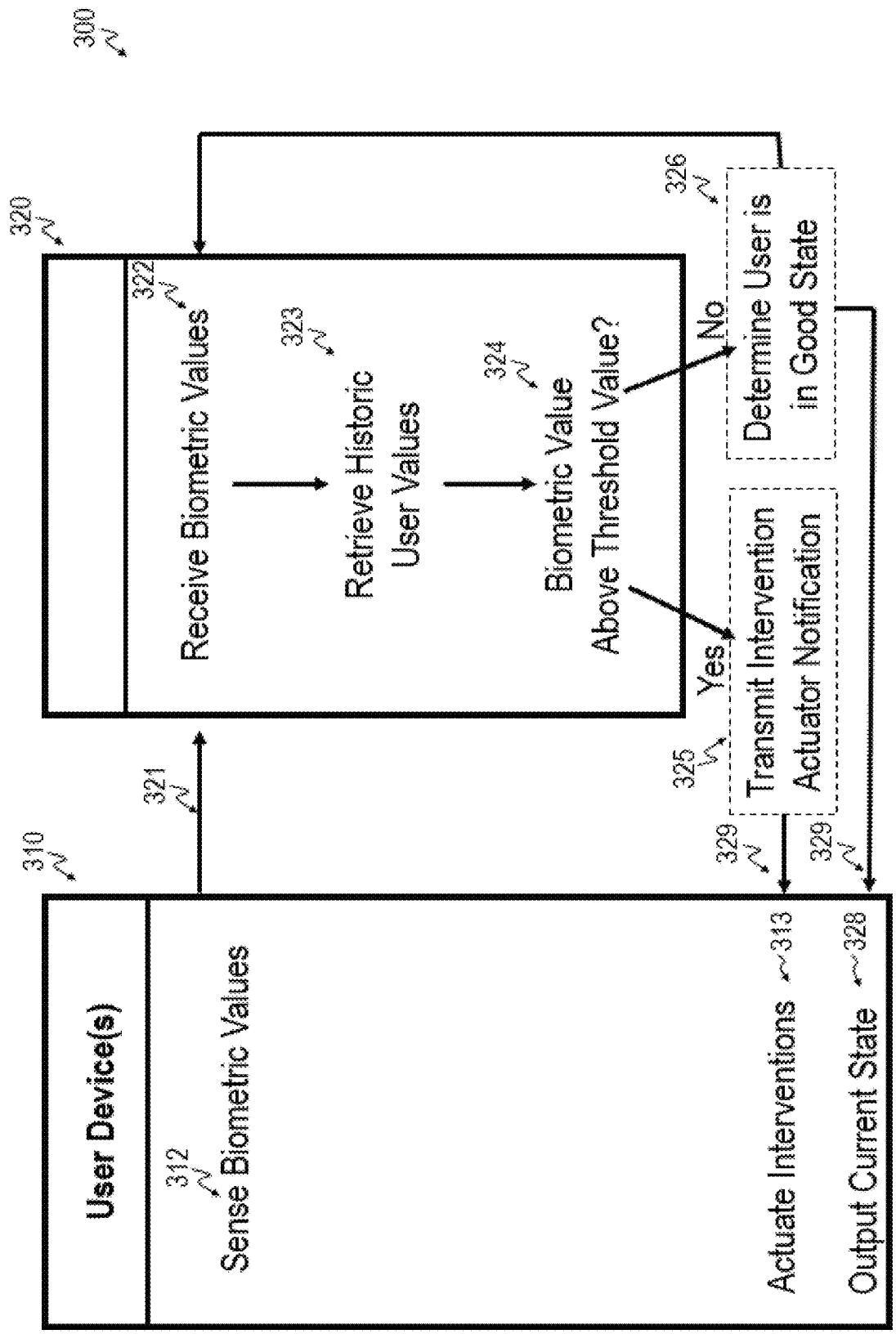
FIG. 5 is a block diagram of a process 300 involving the communications process and transmission of data between the user device(s) and the intervention system/server, according to some embodiments of the disclosed technology.
Figure 6:
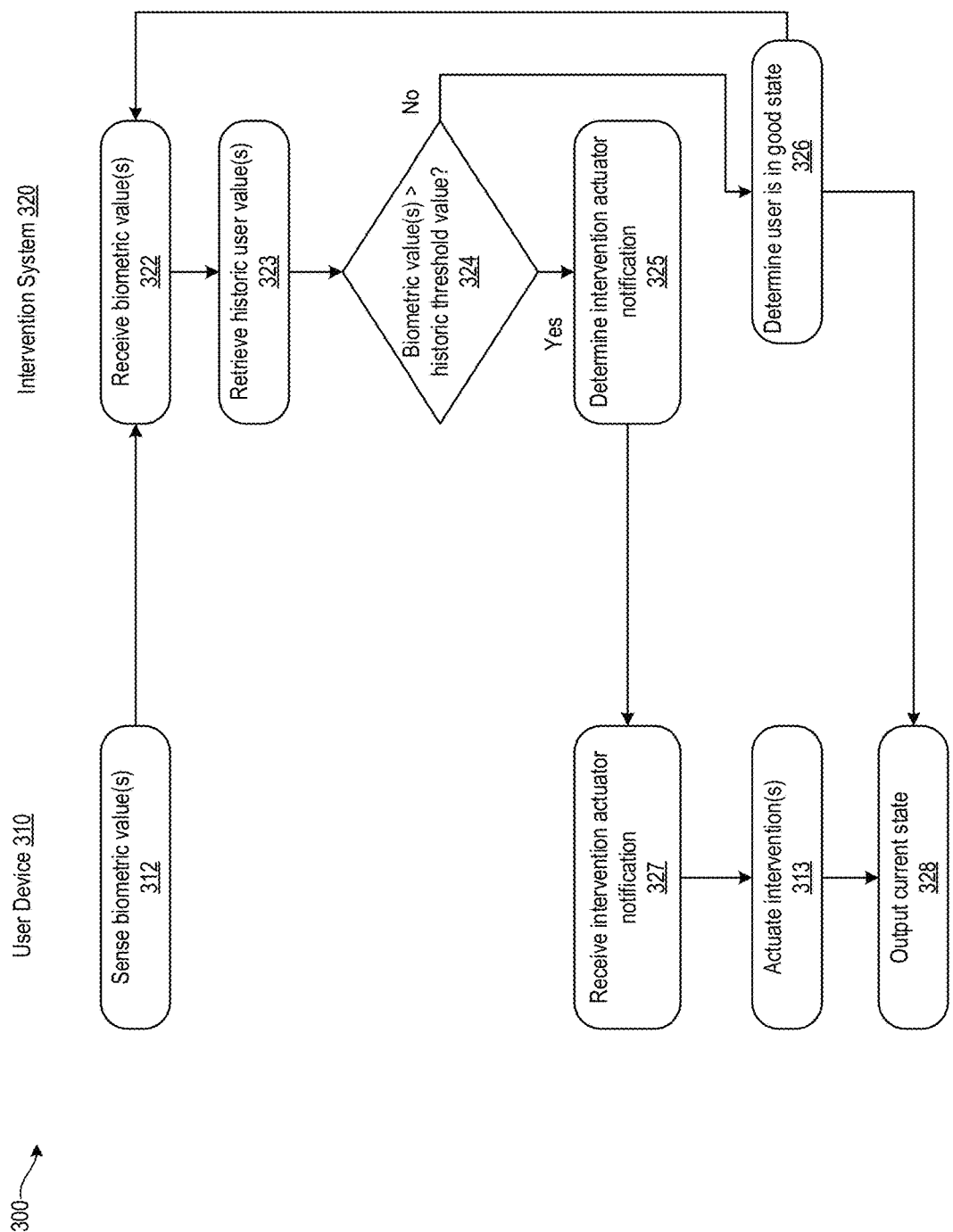
FIG. 6 is a flowchart of the process 300.

FIG. 5 is a block diagram of a communications process 300 including transmission of data 321, 329 between the user device(s) 310 and the intervention system/server 320, according to some embodiments of the disclosed technology. FIG. 6 is a flowchart of the process 300 depicted in FIG. 5. Referring to both FIGS. 5-6, in some embodiments, process 300 includes user devices 310, which may be wearable (such as a smart watch, smart clothing, earphone, belt, necklace or headset) or non-wearable (such as tablet, smart phone, laptop, computer, etc.) and may serve the function as an input device (sensing 312 to obtain biometric values), output device (actuators for interventional stimulations 327) or, in some cases, such as the case of smart clothing or a smart speaker/microphone, both. The intervention system/server 320 can be a physical device, such as a smart speaker or may connect over the network to a server on a different, remote device or in the cloud. In some embodiments, intervention system/server 320 receives 322 the biometric data 321, retrieves 323 historic biometric values and thresholds for this/these user, and compares 324 the current biometric data 321 to the historic biometric values and previously determined thresholds 118, and if the current biometric data 321 exceeds thresholds 118 (indicating that the user is in a crisis state range 120), then transmits 325 commands 329 to actuate interventions 313; else the system has determined 326 that the user is in a "good" state (within normal state range 110) and control passes back to receiving 322, and optionally transmits 329 an indication to the user's device 310 to output the current state to the user 328 as positive feedback to help the user remain in the normal state range 110. Moreover, as depicted in FIG. 3B, once the intervention actuator notification is determined in 325, the user device 310 can receive the intervention actuator notification in 327, actuate intervention(s) 313, and/or output a current state of the user in 328.

As described herein, the present technology is comprised of broad components including an intervention system/server which includes a processor, memory, communication interface and an intervention determiner; user specific database(s); and one or more user device(s) which transmit data via the communication interface over a network (wired or wireless) to the intervention system/server and include one or more input sensors and/or output mechanisms that operate as an alert system.

The present technology uses at least one sensor to read and monitor one or more physical or behavioral indicators. These user devices may be combined or packaged independently or collectively; they may be wearable such as a watch, smart clothing, earphone or other product, or they may be stationary devices, physically independent from the human body, such as a camera, hub, or alarm system in a smart home, or an element of an intelligent building such as a security or HVAC system, device or sensor, as referenced in the related technology in Related Group Crisis State Detection/Intervention Application. While the number of user devices may vary by user (and user group), the devices and sensors, in concert with the intervention system/server and database(s) perform the present technology together.

One or more user device(s)/input sensors are designed to read and measure one or more physical or behavioral indicators. In some embodiments, measurements are taken of a user's heart rate and strength (via heart rate monitor, electrocardiogram "ECG" or "EKG", electromyograph "EMB"), blood flow (via heat sensors, skin sensors), breathing (via thoracic and abdominal sensors), secretions (via GSR, electrodermal activity "EDA"), movement (via accelerometer), and voice (via microphone), among other variables and determinants of crisis states. For example, a heart rate monitor may be used to ascertain heart rate variability (HRV); galvanic skin response (GSR) technology may be utilized to ascertain bodily secretions, or a camera may be utilized to determine concentration levels. The computer-implemented system utilizes one or more biometric and other measures and sensors for readily measuring physical and/or behavioral indicators.

Once these measures are taken by the user device(s), the data are transmitted via the communication interface over a network (wired or wireless) to the intervention system/ server. The intervention system/server can be a cloud-based server, can be the same as the user device(s) (i.e., the intervention server being implemented as software that executes within the user's device(s)), or another server. The information determiner is designed to ascertain the individual's operating level; specifically, if they have transitioned into a crisis state. The information determiner does this by comparing input data from the user devices(s) to historical data and a threshold value in the database pre-determined using computational measures and methods, which may include one or more means such as statistical methods, artificial intelligence, knowledge base, vector space model and any combination of these and/or other methods.

When the intervention system/server determines, via the processor and intervention determiner, that the person has shifted into a crisis state, the intervention system/server promptly transmits data via the communication interface over the network to the user device/output/alarm system to deploy the dual interventions through one or more user/ output devices. By transmitting data to/from the user device(s), intervention system/server, and the database(s), the core system may enable data tracking, data capture, reporting, data analysis and synthesis to optimize user performance and performance of the system and methods.

The entire systems process—from user device(s)/input sensor(s) that measure physiological and biological indicators, to the intervention system/server that receives and processes the data from the input devices and applies computational methods and algorithms to determine crisis levels, to the user device(s)/output mechanism that receive data, alert the user and deploy the dual interventions—is iterative and ongoing.

In other words, the input/sensor elements of the user device(s) are designed to sense/read biometric values. For example, a breathing rate may be taken from a thoracic or abdominal sensor; or sweating may be ascertained from a GSR sensor. These biometric values are transmitted via the communication interface over the network (wired or wireless) to the intervention system/server which receives the biometric values and compares them to historical user values and the threshold value in the database. Via a computational assessment process that occurs in the intervention determiner, the intervention system/server ascertains if the new value is above or below the user's crisis state threshold value.

If the value is below the threshold value—i.e., the value at which the user shifts from a normal state range 116 to a crisis state range 117, the intervention system/server concludes that the user is operating within their normal state range 116 and signals to the user device/output device—by sending data via the communication interface over the network—that no intervention is needed. It also sends the values to the database(s) to be stored. If, however, the biometric value is above the user's threshold value, the intervention system/server concludes that the user has shifted into a crisis state. In this case, the system responds by transmitting data to the user device/output device which then actuates one or both dual interventions—conscious or unconscious—depending on the user or administrator settings/instruction for doing so. All data transmitted to the user device(s) are also sent to the database(s).

FIG. 6 is a process flow of FIG. 5 above. Once the intervention actuator notification is determined in 325, the user device 310 can receive the intervention actuator notification in 327, actuate intervention(s) 313, and/or output a current state of the user in 328, as described herein.

Figure 7B:
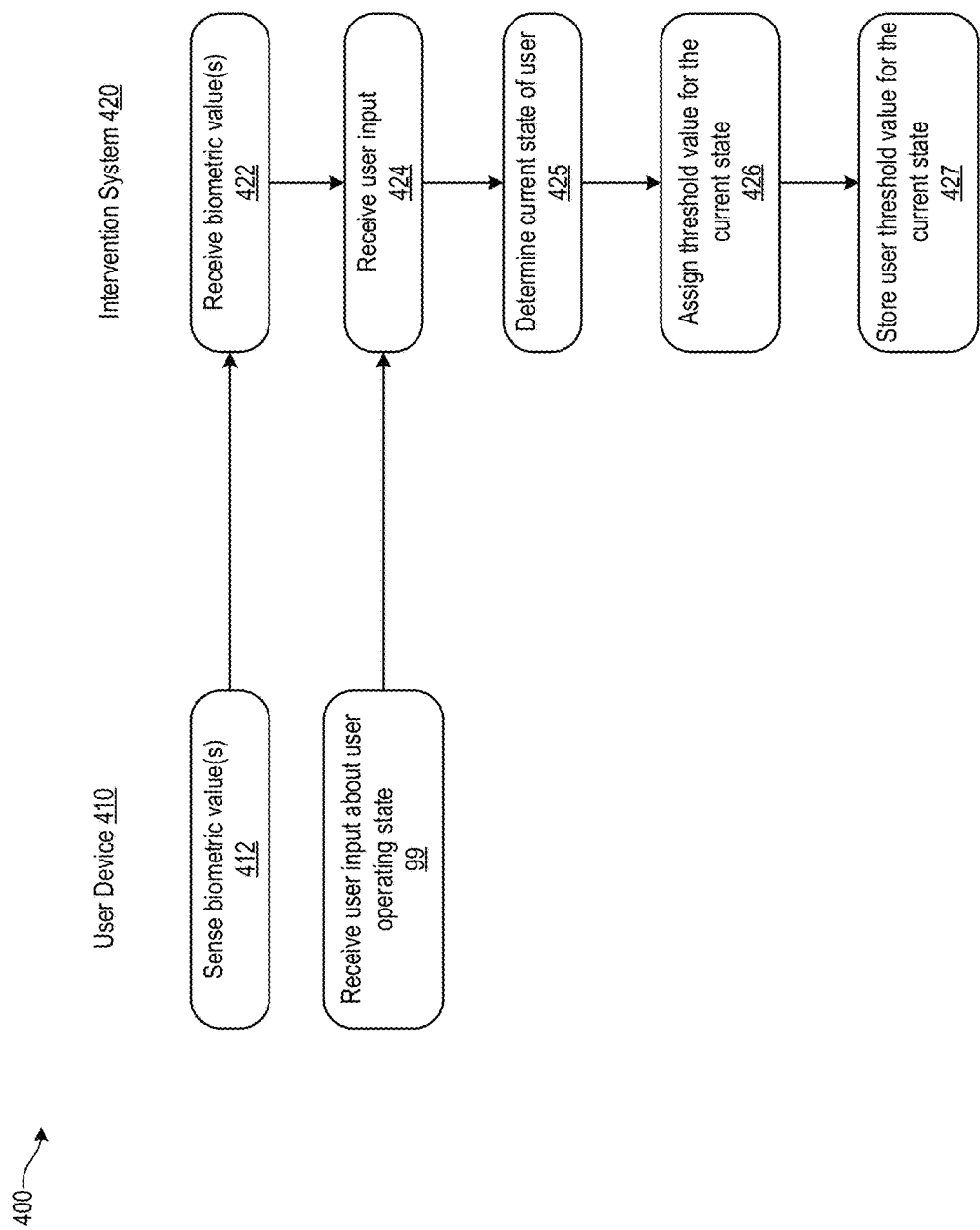
FIG. 7B is a flowchart of the process 400.

FIG. 7A is a block diagram of a process 400 for determining (training) the user's baseline operating state, according to some embodiments of the disclosed technology. FIG. 7B is a flowchart of the process 400. Referring to both FIGS. 7A-B, in some embodiments, process 400 includes a user device 410 that functions as an input device, sensing 412 biometric values 421 such as heart rate strength or variability via a smart watch or vocal speed, pace or volume via a microphone in an earphone. In some embodiments, intervention system 420 receives 422 the sensed biometric values 421, elicits and receives 424 user input (e.g., user state values of, for example, crisis state 414 or normal state 120) from user 99, determines state parameters 425 based on the received user state values, and assigns trained threshold values 426. In some embodiments, the assigned threshold values are stored in database 416 in 427. In some embodiments, after intervention system 420 elicits and receives 422 user input, a user or administrator, acting on the user's behalf (e.g., child, ward of the state) 99 evaluates, rates, and enters their personal operating state (e.g., the user's own perception of their state value), and in some such embodiments, user 99 enters the user state value via a smart phone, tablet or desktop computer using voice commands and/or data, touchscreen or keyboard commands and/or data, hand gestures or the like, and the values are then transmitted to intervention system 420 via the network 299.

In other words, depicted is the training process 400 for determining the user(s) Normal State Range 116. This process can be performed because every person (or collection of persons, in reference to related disclosed technology Related Group Crisis State Detection/Intervention Application) has a distinctive set of "normal" physiological parameters or parameter ranges (analogous to a "normal temperature" in a human of 37 C) at which they operate optimally. This Normal State Range can be slow and peaceful for some people and fast and dynamic for others. This present technology uses methods (e.g., computational algorithms, statistical analysis, database, knowledge base, machine learning) to ascertain the normal state range 110 of a person and takes this baseline into account to set the crisis-level threshold 118. The process begins with the user device(s)/input sensor(s) which sense the biometric values and transmits the data via the communication interface over the network to the intervention system/server. The intervention system/server sends a signal to the user device(s) prompting the user or user's administrator to evaluate the current operating state—i.e., would they characterize the current state as a crisis state or a normal state? During this training period, the user (or administrator) enters their response into the appropriate user device, which then communicates the response to the intervention system/server, where the set of all such responses is used to set-up and periodically thereafter to calibrate and adjust the threshold level that is used to evaluate symptoms (one or more sets of physiological parameters) that are to be evaluated—either one at a time (moment-by-moment evaluations, each of a single set of parameters) or across a period of time (determining changes in the sets of parameters over one minute, five minutes or an hour, for examples). The user's evaluations initially set the threshold level for the set of physiological parameters or for changes in the physiological parameters, thus training or guiding the intervention system/server, which then uses the training data to determine the user's crisis state parameters and threshold level. The system is configured to conduct periodic operating-state measurement, calibration and reclassification efforts to ensure the crisis state parameters and threshold values are and remain current. Via an on/off switch or other such mechanism, the human user, or administrator on their behalf, controls whether these periodic, ongoing threshold training efforts are conducted manually via user or administrator input or are systematically driven utilizing the intervention determiner and its computational functionality.

FIG. 8 is a block diagram of a dual-intervention system 500, according to some embodiments of the disclosed technology. In some embodiments, system 500 includes a plurality of user devices 510 (e.g., user device 511 and user device 512 and optionally additional user devices not shown) and an intervention system 520 that can cause the generation of sensory unconscious (e.g., imperceptible or barely perceptible) feedback 514 such as imperceptible audio feedback via an ear piece, or consistent, mild haptic feedback via a device such as a smart wrist band or watch, and that can cause the generation of conscious (e.g., perceptible) feedback 515 in the form of an intervention app from one of several stress-mitigating themed sub-collections or its results presented to the user with which to engage with data captured by the system through a device such as a smart phone, tablet, smart watch, headset, desktop or other user device. In some embodiments, the plurality of user devices 510 read 513 biometric values 521 of the user and sends the biometric values 521 to the intervention system 520. In some embodiments, intervention system 520 includes the intervention system/server 525 that receives 522 the biometric values 521, and determines 523 whether the received biometric values 521 are below the threshold value (in some such embodiments, when the intervention system/server 525 determines that the value is NOT below the threshold value, intervention system 520 causes the generation of sensory unconscious feedback 514 and/or conscious feedback 515 at, for example, the plurality of user devices 510. In some embodiments the unconscious and conscious interventions are delivered through the plurality of user devices 510 (e.g., a smart phone or watch); in some other embodiments the unconscious and conscious interventions are delivered through entirely different devices, which may be wearable or not wearable, or, in reference to related disclosed technology Related Group Crisis State Detection/Intervention Application, part of an intelligent home or building system (e.g., delivering the subtle aroma via a building ventilation system or air freshener that is configured to wirelessly receive commands to emit a selected one or more of a plurality of possible scents).

FIG. 9 is a block diagram of an unconscious (imperceptible) intervention system 600, according to some embodiments of the disclosed technology. In some embodiments, system 600 includes a user device 610 that senses/reads 612 biometric values 621 and transmits the values 621 to the intervention system 620. In some embodiments, intervention system 620 includes intervention system/server 625 that receives 622 the biometric values 621 and determines 623 whether the values are below the threshold value. In some embodiments, when the received biometric values 621 are NOT below the threshold value, intervention system 620 causes the user device 610 to provide the sensory unconscious feedback 514 that is imperceptible, or optionally perceptible but unobtrusively so, such as haptic vibration through a smart watch, belt or clothing. In other words, FIG. 9 represents an exemplified and non-limiting overview of the unconscious intervention. This intervention process is automatically actuated if the intervention system/server receives a biometric value or values from the user device(s)/input sensor that is above the crisis state threshold level. To mitigate the crisis state, the intervention system/server transmits data to the user device(s)/output mechanism which then provides sensory feedback to the user which is designed to modulate the stress response and return the user to their normal state. The sensory feedback can be in the form of touch, sight, sound, smell or taste, depending on the device and its purpose.

FIG. 10 is a block diagram of a conscious (perceptible) intervention system 700, according to some embodiments of the disclosed technology. In some embodiments, system 700 includes a user device 710 that senses/reads 712 biometric values 721 and transmits the values 721 to the intervention system 720. In some embodiments, intervention system 720 includes intervention system/server 725 that receives 722 the biometric values 721 and determines 723 whether the values are below the threshold value. In some embodiments, when the received biometric values 721 are NOT below the threshold value, intervention system 720 causes the user device 710 to provide an application ("app") recommendation 713 from one of five proven-effective stress-reducing themed app sub-collections (Creative Release, Physical Release, Verbal Release, Change Environment, Change Mindset.) In some embodiments, the difference between the imperceptible intervention and perceptible intervention is a matter of degree, intensity, number of senses stimulated, the number of times stimulation is repeated, and the like. In some embodiments, the app provided in app recommendation 713 prompts a verbal release (such as speaking aloud to oneself or via the device to others). In other embodiments, the intervention could be an app that prompts a physical release (such as instructions to engage in physical activity or exercise), a creative release (such as the entry or manipulation of words or writings or visuals in a device that is an element of the system), a wholesale change in environment, a change in mindset or other category of action/intervention demonstrating efficacy swiftly mitigating the human stress response. In some embodiments, the applications are designed to offer an IMMEDIATE intervention which may be the only intervention or coupled with other interventions (i.e., activities) designed to build positive habits, improve skills, and/or increase body awareness. In some embodiments, when intervention system 720 is "OFF", the user can proactively make an app selection 716 via the user device 710. In other words, FIG. 10 represents an exemplified and non-limiting overview of the conscious intervention system. The conscious intervention system is designed to deliver software application interventions aligned with several long-standing and proven-effective crisis intervention sub-collections including but not limited to verbal, creative, environmental, physical, and mental. The system is scalable in that there is no limit to the number of the software applications that can be developed, included and offered in each themed crisis intervention app sub-collection. This flexible and scalable feature enhances the overall efficacy and applicability of the system for diverse populations, individuals, and groups.

The conscious intervention system has two-modes, user-directed and system-directed. In the system-directed scenario, the user device(s)/input sensor reads a biometric value and transmits the value via the communication interface over the network to the intervention system/server which, via its intervention determiner, senses the value, compares it to historical values and the threshold value stored in the database(s), and makes a crisis state determination. If a crisis state is ascertained, the intervention system/server will transmit data via the communication interface over the network to the user device(s)/output mechanism recommending a specific software application that has demonstrated efficacy in mitigating previous crisis states with similar characteristics. The user may choose to deploy the software application or select another from the software collection.

If the user or administrator on the user's behalf, prefers to maintain control of the conscious intervention/software application selection, the only difference is that when the intervention system transmits data to the user device(s)/output device(s), an intervention solution/software app will not be offered. Instead, the user or administrator will receive a notification and will be prompted to make a software app selection on their own.

Figure 11:
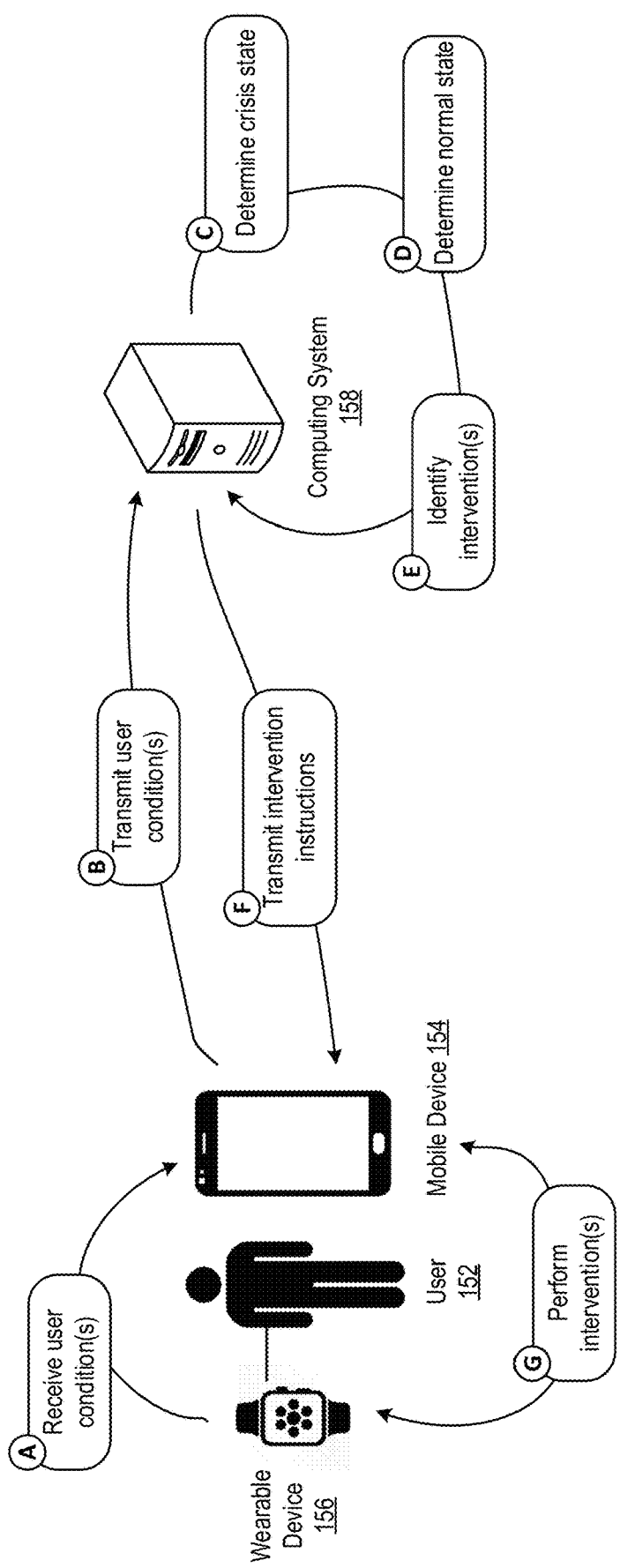
FIG. 11 is a conceptual diagram of the disclosed system.

FIG. 11 depicts a user 152 having a mobile device 154 and a wearable device 156. The mobile device 154 can be in communication with a computing system 158, as described throughout this disclosure. The wearable device 156 can include one or more biometric sensors configured to sense conditions of the user 152. The mobile device 154 can receive the sensed user conditions in step A. the mobile device 154 transmits the user conditions to the computing system 158 in step B. Using those user conditions, the system 158 can determine a crisis state of the user 152 in step C. In step D, the system 158 can also determine a normal state of the user 152 based on one or more conditions sensed while the user 152 is not in the crisis state. Based on the determinations made in steps C and D, the computing system 158 can identify one or more conscious and unconscious interventions, as described throughout this disclosure (step E). The system 158 can transmit intervention instructions to the mobile device 154 in step F. In some implementations, as described herein, the intervention instructions can prompt the mobile device 154 to automatically perform an intervention without user input. In other implementations, the intervention instructions can prompt the mobile device 154 to display to the user 152 one or more intervention techniques that the user 152 can select and perform. In step G, the mobile device 154 and/or the wearable device 156 can perform the intervention(s) to assist the user 152 in lowering from the crisis state to the normal state. Steps A-G can be repeated for a predetermined amount of time. In some implementations, steps A-G can be repeated for as long as the computing system 158 determines that the user 152 is in the crisis state. In yet other implementations, steps A-G can be continuously repeating, even when the user 152 causes one or more of the mobile device 154 and the wearable device 156 to be disconnected from the computing system 158 and/or turned off.

Figure 12:
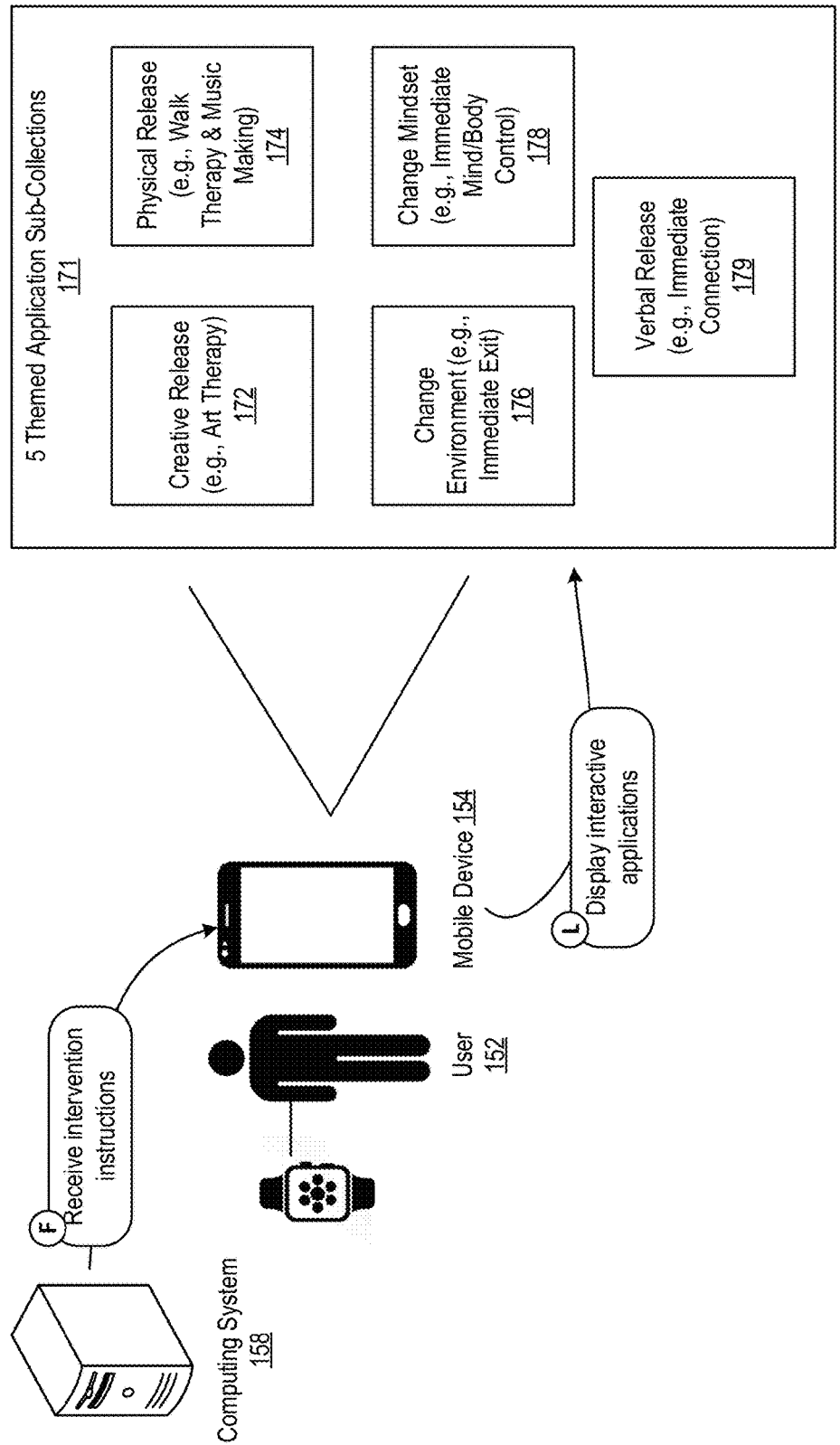
FIG. 12 is a conceptual diagram of the disclosed system and five themed application sub-collections.

FIG. 12 outlines the structure and process of the CONSCIOUS INTERVENTION application collection—specifically the five app sub-collections 171 each aligned with a proven crisis state mitigating area. This figure depicts the disclosed technology performing conscious intervention when it is determined by the computing system 158 that the user 152 is in the crisis state. Once the user mobile 154 receives intervention instructions from the computing system 158, the device 154 can be prompted to display interactive application(s) as described throughout this disclosure to the user 152 in step L. A mobile user interface display 170 can output one or more interactive mobile applications that are tailored to assist the user 152 in consciously lowering from the crisis state to the normal state. As described throughout this disclosure, various different software applications each aligned with one or more of five proven crisis mitigation areas can assist the user 152. By way of a non-limiting example, the exemplary display 170 includes a creative release application 172, a physical release application 174, a change environment application 176, a change mindset application178 and a verbal release application 179 as described above as one advantage of the disclosed technology and outlined in one or more figures described herein. In other implementations, fewer or more interactive applications can be displayed to the user 152. Moreover, as described herein, the interactive applications can be displayed to the user 152 simultaneously, before, or after unconscious intervention is performed by the computing system 158 and the mobile device 154. This duality of conscious and unconscious intervention is advantageous to assist the user 152 in more quickly lowering from the crisis state to the normal state, as described in more detail throughout this disclosure. The software apps are designed as crisis state mitigators. In some embodiments, the intervention app collection includes themed sub-collections each with a history and track-record of success diffusing physiological stress responses and include physical releases, creative releases, verbal releases, changing one's environment, changing one's mindset, and more For example, one of the applications in the Physical Release Sub-Collection can prompt a user to engage in a nature-based physical activity. The app offers immediate interventions to de-escalate the user from a crisis state with expediency supported with lengthier activities and best practices designed for skill, habit and resiliency-building. Another one of the applications aligned with the Creative Release Sub-Collection can include music engagement, art therapy, movement-based creative expression, and/or expressive writing prompts. As yet another example pertaining to the Verbal Release Sub-Collection, one or more of the applications can be configured to connect the user with other people to leverage social support. For example, the application can prompt the user to contact a friend or family member, a doctor, and/or a psychologist. As another example, the application can automatically call/contact a friend or family member, a doctor, and/or a psychologist without receiving permission from the user. In yet other implementations, one or more of the applications can also include unconscious sensory-based interventions utilizing light, sound, and/or aroma stimuli, for example, to add another layer of impact to the conscious app interventions. In the "Change Environment Sub-Collection," one or more applications can additionally and/or alternatively provide the user with GPS and user preference based suggestions on immediate outdoor excursions to allow nature to work its wonders on the human stress response. For example, an application can prompt the user to take a thirty minute walk in a nearby park. As a result of immersing the user in a positive, different, and natural environment, the user can lower from a crisis state to a normal state.

It is important to note that in the present system, while it is the user that must perform the activity, it is the computer system that prompts and suggests the optimal activity to a specific user based on historical usage, performance, and efficacy of mitigating the crisis state. And, although the alert and/or suggestion is systematically driven by the technology to the user, upon receipt of the alert, the user may choose or not choose to act upon the alert by deploying the intervention. In summary, with the conscious intervention method, while the technology makes a recommendation based on biometric values and computational processing and algorithms, it is the user that ultimately controls activation of the intervention.

The person(s) can choose from among many software interventions aligned with his/her preferences or need state. Or—because the system is powered by artificial intelligence, machine learning and/or other computational methods and is continually learning and optimizing interventions at the individual or group level—they may allow the system to recommend an optimal software application or interventional tool or experience.

The CONSCIOUS, person-driven software applications and interventions of the disclosed technology induce the person to take immediate action by engaging with one of several apps aligned with research-backed crisis mitigation areas that directly or indirectly diffuse the crisis state. Recall that human beings are controlled by three elements: emotions, thoughts, and actions. We can't change our emotions directly. Changing our thoughts is difficult. Actions are the easiest to control—particularly in a state of extreme physiological arousal. Actions offer a positive, alternate activity that gain control of runaway human stress responses by offering an immediate diversion. These engrossing activity-based interventions modulate physical and/or behavioral indicators thereby returning the person to their non-crisis or normal operating state. As mentioned, the crisis mitigation areas deliver crisis relief via one or more intervention app sub-collections which may include, among other factors, verbal release, physical release, creative release, change environmental or change mindset.

The present technology is user (and group adaptive) because the intervention system/server and the user device(s) are continually transmitting, evaluating, and sharing data via the network (wired or wireless). This ongoing iterative, evaluative communication and data sharing process between core system components allows for adjusting or modifying interventions and/or recommendations, if applicable, to each person's needs, and the severity, frequency, and duration of their crisis states. In addition, the transmission of data to the database(s) may enable a self (or group-portrait) by a person or administrator on their behalf, or the data may be stored for subsequent manipulation, analysis, or reporting.

The DUAL INTERVENTIONS may occur concurrently or independently, situationally determined by the user or the administrator on their behalf. The intervention system/server, because of its multifunctionality, may use one or more applications or other software to record the timing, duration, and the characteristics of the crisis state, and the person's response to the interventions individually (or collectively) deployed, and transmit this data to the database(s) for storage, manipulation and/or subsequent retrieval.

Figure 13:
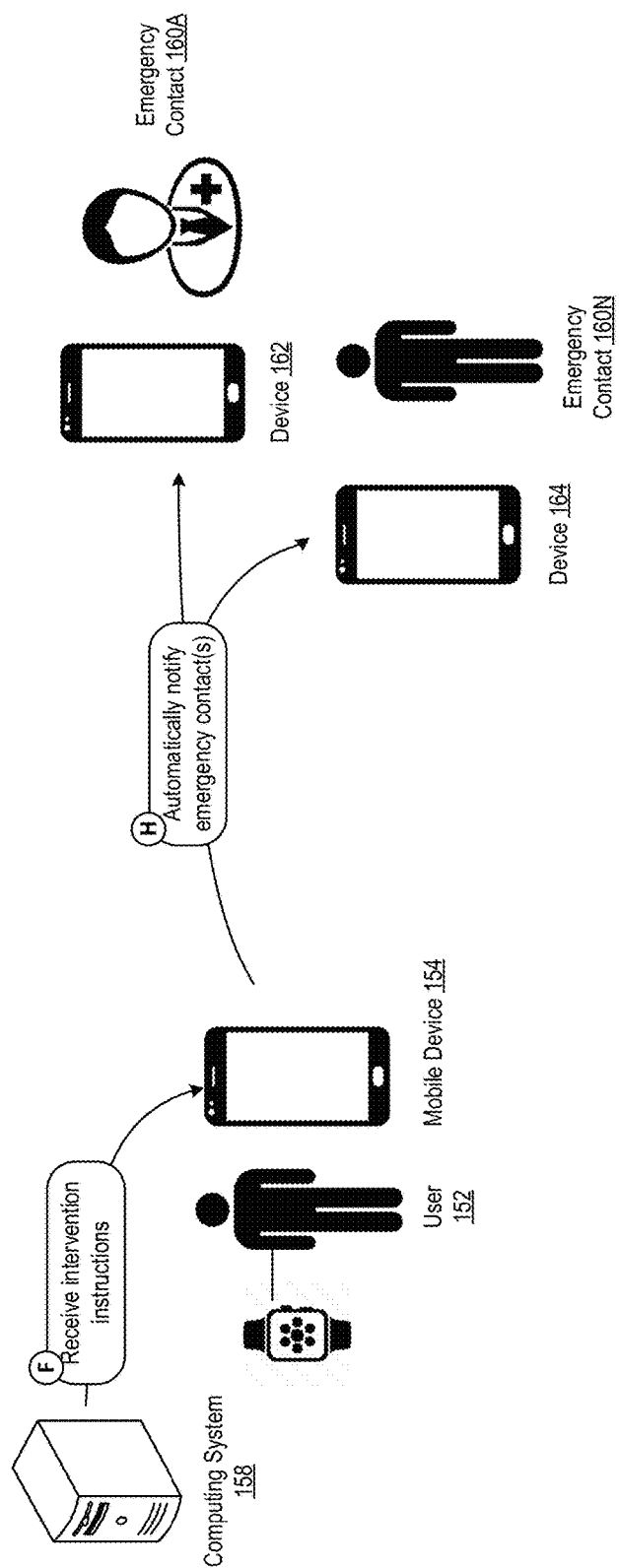
FIG. 13 is a conceptual diagram of intervention through a verbal release application.

FIG. 13 is an overview of a process of one of the features of an exemplary software application included in the Verbal Release app sub-collection, as detailed at the beginning of the disclosure above. FIG. 13 depicts the disclosed technology intervening on its own when it is determined by the computing system 158 that the user 152 is in the crisis state. The mobile device 154 can receive automatic intervention instructions from the computing system 158 in step F. The mobile device 154 can be configured to automatically dial, contact, and/or otherwise notify one or more emergency contacts of the user 152 (step H). As depicted, emergency contacts 160A-N are automatically contacted at their devices 162 and 164, respectively. As described herein, when the user 152 is in the crisis state, the user 152 may not want to notify a family member, friend, coach or other emergency contacts of their state. However, notifying close supporters and/or emergency contacts can be an effective way to assist the user 152 in lowering from the crisis state to the normal state. Thus, the mobile device 154 can be configured to automatically contact the close supporters and/or emergency contacts without user consent or input. If the user 152 tries to turn off their mobile device 154, the device 154 can still transmit a GPS location signal to one of more of the emergency contacts 160A-N before the device 154 is turned off. In other implementations, the mobile device 154 can automatically transmit the GPS location signal, a message, voice call, or some other form of notification to the devices 162 and/or 164 immediately upon the computing system 158 determining that the user 152 is in the crisis state. As a result, the emergency contacts 160A-N can still take action to assist the user 152, no matter if the user 152 attempts to disconnect the mobile device 154 from a network or communication with the devices 162 and 164.

Figure 14:
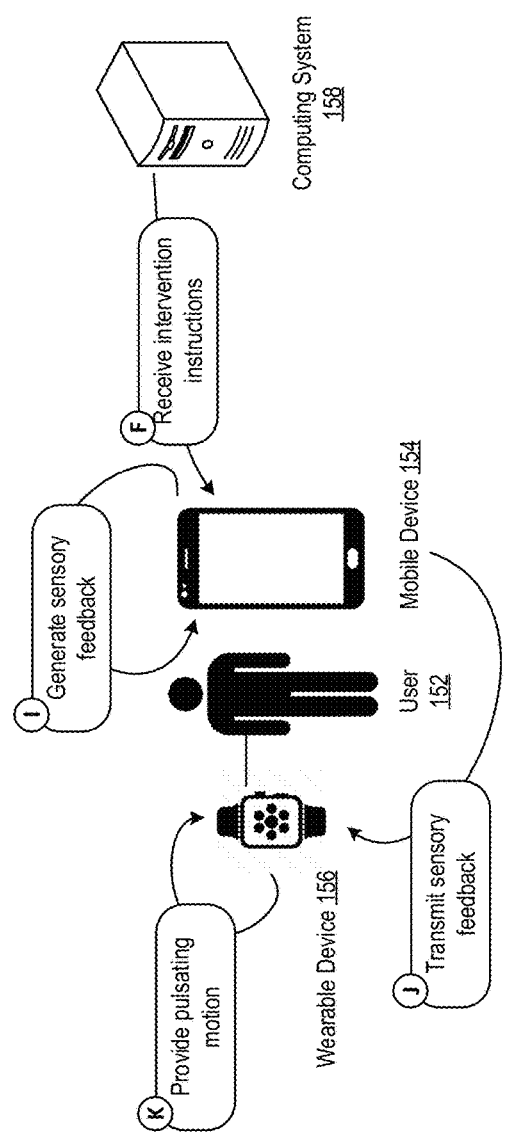
FIG. 14 is a conceptual diagram of intervention through sensory feedback.

FIG. 14 depicts the disclosed technology performing unconscious or sensory-based intervention when it is determined by the computing system 158 that the user 152 is in the crisis state. The mobile device 154 can receive conscious (e.g., automatic) intervention instructions from the computing system 158 in step F. The mobile device 154 can be configured to generate a sense-based type feedback in step I, such as haptic feedback to a wearable device calibrated to emit pulses slower than the user's heart rate. In some implementations, step I can be performed by the computing system 158 then transmitted to the mobile device 154 and/or the wearable device 156.

Next, in step J, the mobile device 154 can transmit the generated UNCONSCIOUS sensory feedback to the wearable device 156. The wearable device 156 can then provide sensory feedback (e.g., a pulsating motion) to the user 152 in step K. The purpose of direct sensory (UNCONSCIOUS) intervention is to grab hold of a runaway human stress response by diffusing a threat perceived by the sense organs of the human body. Recall that the sensing organs associated with each sense send information to the brain to help us understand and perceive the world around us. The unconscious sensory interventions send different—non-threatening—messages to the brain. For example, the sensory intervention can be a haptic pulse that is paced slower than the human heart rate or an aroma that has a proven calming effect on the human body. These sensory-based, UNCONSCIOUS INTERVENTIONS can be implemented without distracting the user (e.g., preventing the user from carrying on with a current task) or inducing a sense of overwhelm by forcing the user to cognitively focus on their body in the midst of an out-of-control human stress response.

In some implementations, the sensory-based feedback can be provided to the user 152 for a predetermined period of time. The sensory feedback can optionally be provided to the user 152 for as long as the computing system 158 determines that the user 152 is in the crisis state. In yet other implementations, the sensory-based feedback can be provided to the user 152 in conjunction with one or more other conscious and/or unconscious interventions described throughout this disclosure. Moreover, the sensory feedback that is provided to the user 152 can be based on a determination of which state the user 152 is in, what additional conscious and/or unconscious intervention is provided to the user 152, and what sensory (touch, sight, hearing, smell and taste, for example) feedback has been effective in the past in lowering the user 152 from the crisis state to the normal state, as described throughout this disclosure.

Figure 15:
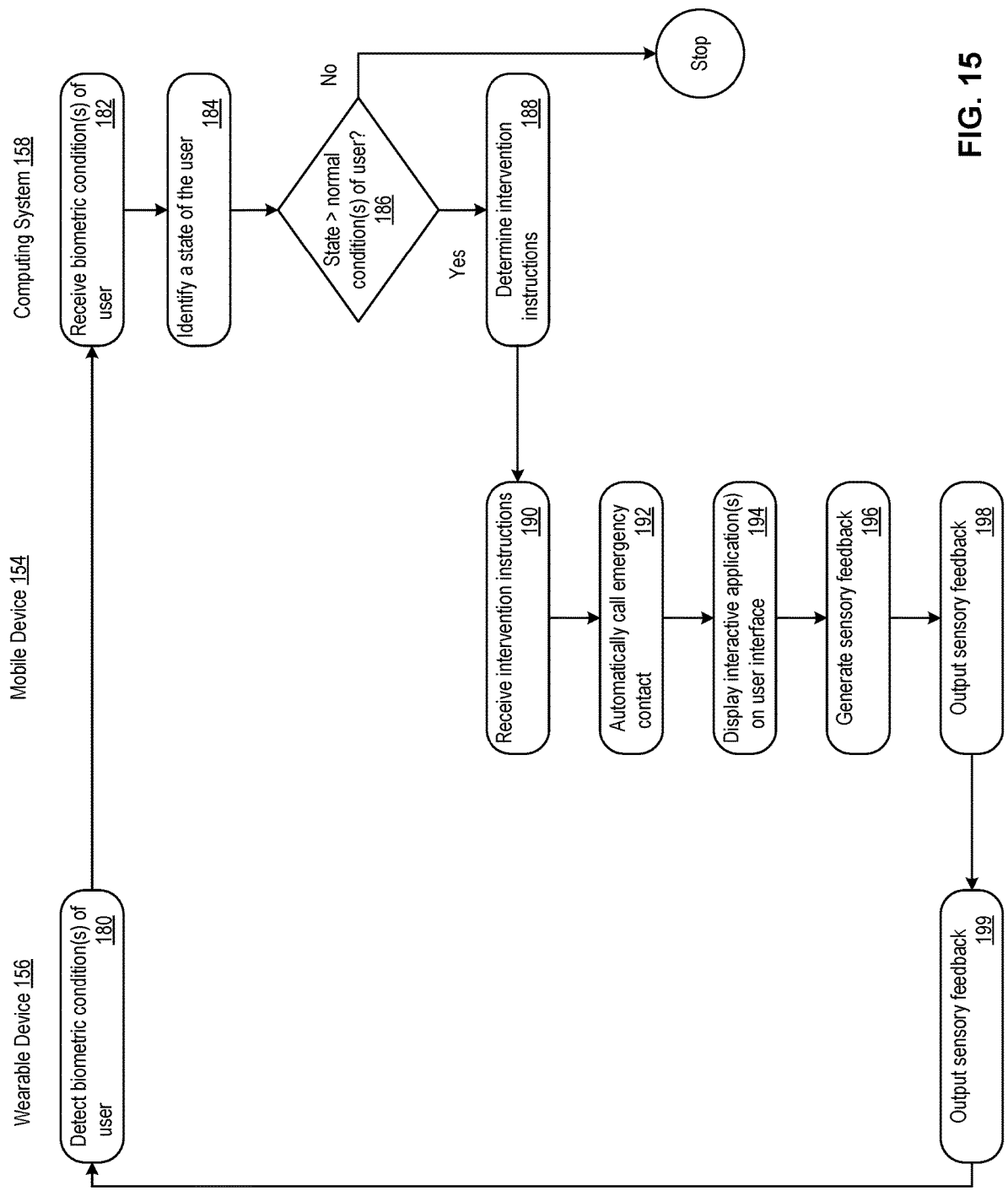
FIG. 15 is a flowchart of a process for detecting a human crisis state, according to some embodiments of the disclosed technology.

FIG. 15 is a flowchart of a process for detecting a human crisis state and implementing an automatic—non-avoidable—intervention where the individual may not be able to make appropriate decisions to reduce him/herself from the crisis state as outlined earlier in the disclosure, according to some embodiments of the disclosed technology. As depicted, the wearable device 156 can detect biometric conditions of a user in step 180. The computing system 158 can receive the biometric conditions in step 182. The system 158 can then identify a current state of the user in step 184. In step 186, the system 158 can determine whether the current state of the user exceeds a normal condition of the user. If the current state exceeds the normal condition of the user, then the user is in a crisis state and the system 158 determines intervention (conscious and/or unconscious) instructions in step 188. If it is determined that the current condition does not exceed the normal condition of the user, then the process stops. Or, optionally, a positive intervention can be offered to the user as a positive reinforcement.

Once the system 158 determines intervention instructions in step 188, the mobile device 154 receives the intervention instructions in step 190. In some embodiments, the device can automatically implement the Immediate Connection App from the Verbal Release app sub-collection and release the automatic dial feature to contact an emergency contact without the user's permission or awareness in step 192. After proactively making the emergency connection, the device 154 can display the interactive application(s) on a user interface as part of the app intervention in step 194. The device 154 can also generate automatic unconscious sensory-based feedback (touch, sight, hearing, smell, and taste) without prior user approval, permission, or awareness. In step 196, output the sensory feedback in step 198, and transmit the sensory feedback to be outputted by the wearable device 156 in step 199. In some implementations, one or more of the steps 192-199 can be performed. For example, as described herein, where a conscious software application intervention is used, only steps 192 and 194 may be performed. In other examples, where unconscious (imperceptible) intervention is used, one or more of steps 196, 198, and 199 may be performed. In yet other implementations where both conscious and unconscious intervention are simultaneously performed or performed before or after each other, one or more of the steps 192-199 may be performed.

Finally, as depicted and described herein, the process and steps 180-199 can be repeated.

FIGS. 16 to 21 are exemplary user interfaces of the conscious intervention system described herein. The exemplary user interfaces are not meant to be limiting. As described throughout this disclosure, one or more alternative user interfaces/interactive mobile applications can be provided to the user at the user device 710.

Figure 16:
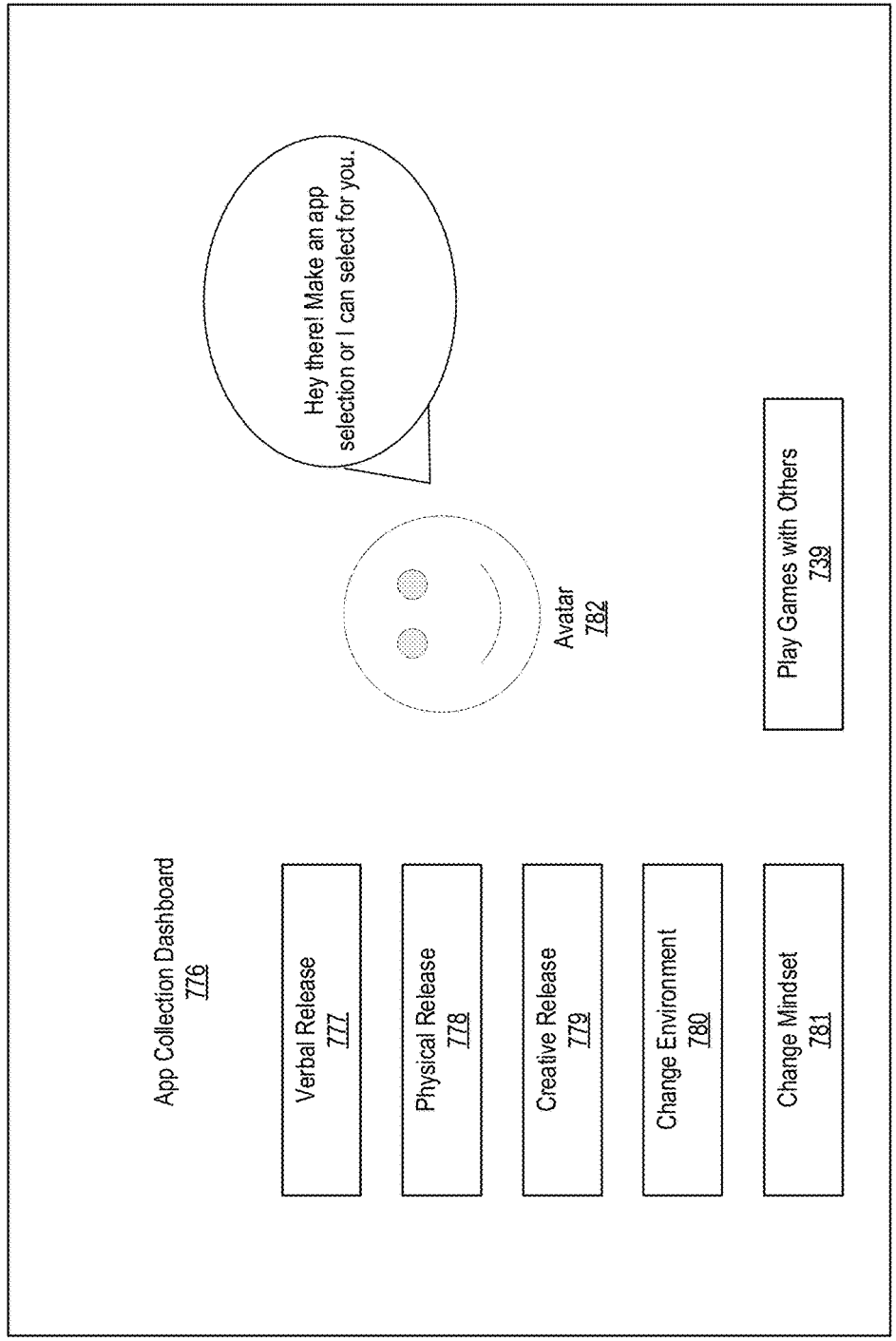

FIG. 16 depicts a user interface 775 having an app collection dashboard 776. The dashboard 776 can include selectable options for different applications within themed sub-collections. For example, the dashboard 776 can include buttons for the verbal release app sub-collection 777, the physical release app sub-collection 778, the creative release app sub-collection 779, the change environment app sub-collection 780, and the change mindset 781 app sub-collection. As depicted, the app collection dashboard 776 can offer five different types of interventions (e.g., themed sub-collections), each aligned with one or more of five immediate outlets for reducing crisis states—verbal, physical, creative, change environment, and change mindset. All of the software applications offer an IMMEDIATE intervention for swift, no-nonsense mitigation of crisis states, in addition to one or more steady-state interventions and/or activities centered on improving skills, gaining insight and awareness, getting support/help, and engaging with others. The software interventions depicted and described herein can activate a mesolimbic pathway of the user's brain (aka "the pleasure center.") Positive emotional states can arise from influencing a core neurophysiological system (related to valence—a pleasure-displeasure continuum) that shifts user's affective state from displeasure to pleasure. In addition, one or more of the applications described herein can provide for targeted resynchronization of rhythms in human behavior to improve mood disorders. One or more of the applications can assist the user in learning how to synchronize their mental states with daily exercise, creative outlets, and reducing stress drivers. Importantly, the applications can provide for continuous learning, skill-building, habit-building, and improved body-awareness in addition to user engagement in the monitoring, capturing, and analyzing of de-escalation response times based on intervention type. This analysis, and the knowledge and insight gained, can be useful not just for everyday stress reduction or crisis intervention for an individual, but also for clinical interventions in care settings.

The dashboard 776 can also include an option to engage in collaborative activities with others founded on the principles and best practices of game-play 739. Interactive activities with others can be played as local multiplayer or online multiplayer (e.g., local wireless). Example interactive applications can provide for social sharing of artwork or music that anyone can edit and save. Therefore, others in a community can build on or add to the user's artwork created or music made. Another example interactive activity/game can provide for allowing multiple people to work on art or music concurrently (e.g., at the same time and in real-time). This type of activity/game can provide for concurrent team creation. Another example activity/game can provide for the system to select a base art or melody for people to create together and then the system can randomly assign a limited set tools and/or sounds to each member of the game. In this scenario, each person can contribute to the group creative-process with limited resources. Limiting game-participant resources adds elements of strategy, cooperation, and collaboration.

In addition, as depicted, an avatar 782 can be displayed on each interface. The avatar 782 can provide personalized messages to the user, based on how the user is feeling, one or more biometrics that were determined for that user, and suggestions on what applications 777, 778, 779, 780, 781, and 739 may be most helpful to assist the user in lowering to a normal operating state. For example, the avatar 782 in the user interface 775 is saying, "Hey there! Make an app selection or I can select for you." Moreover, as described herein, tailored messages can be generated for the avatar 782 based on AI, machine learning, or other techniques that can be used to predict conditions of the user and optimal intervention for that user.

All applications include a button or other selectable option that provides for IMMEDIATE intervention. Therefore, where the user is in the crisis state and feeling that they are in an emergency, selecting this option can bypass one or more session preferences (e.g., whether the user would like to work with a human coach versus an AI/Smart coach). Access to immediate emotional outlets is key when dealing with crisis state de-escalation. Moreover, when the system automatically intervenes, as described in FIG. 15 above, depending on how much the user exceeds the normal state range, the system can bypass the one or more session preferences and immediately begin the system-selected intervention.

Figure 17:
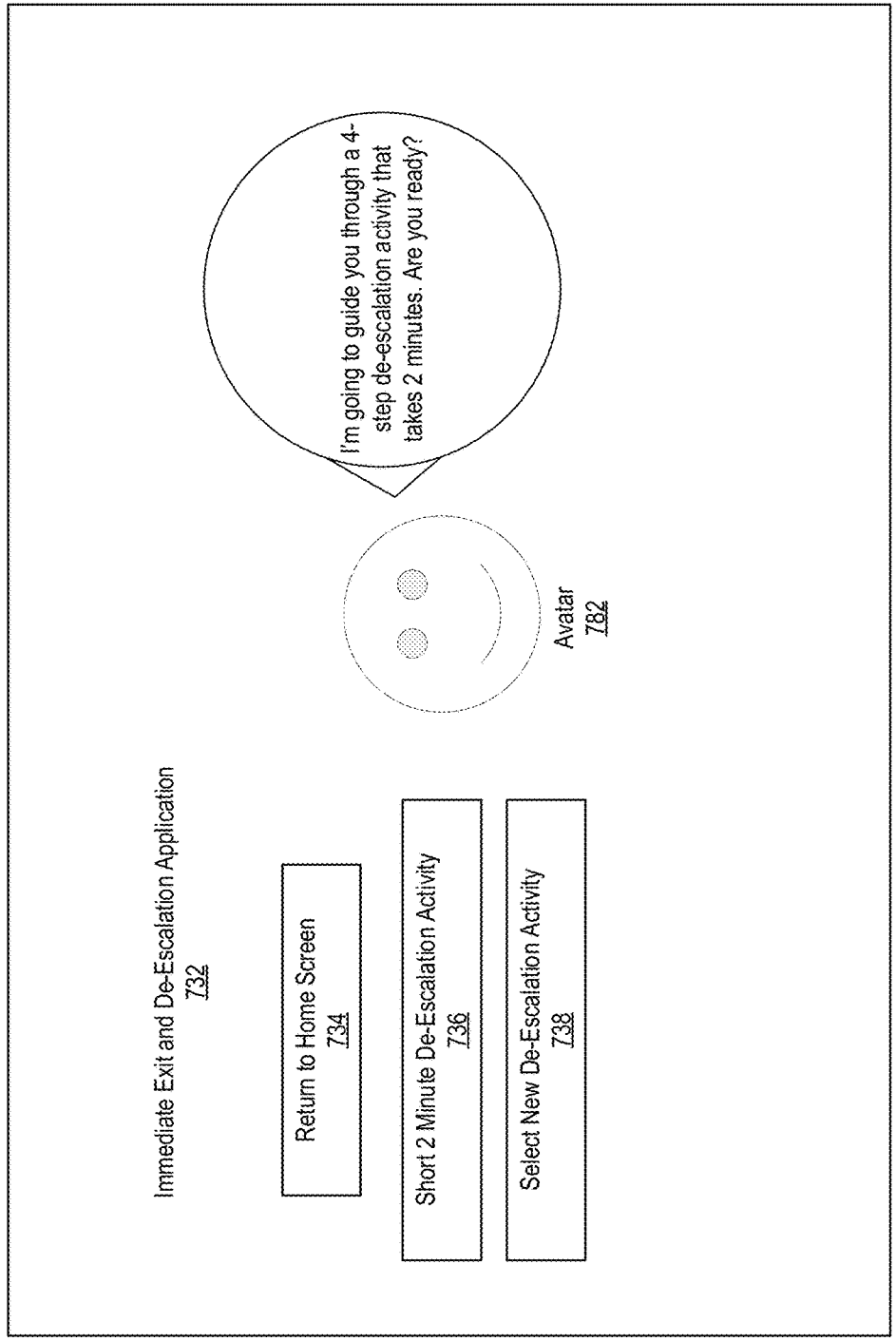

FIG. 17 depicts an exemplary app within the Change Environment sub-collection user interface 780. In other words, the user can select option 780 from the dashboard 776 or the interface 780 can be automatically displayed to the user for autonomous intervention, as described herein. The user exits their current environment and moves to a safer/different environment before the intervention activity can start. In some embodiments the user may be required to notify the system that he/she is ready to begin. In other embodiments, the GPS system within the user device can track the user's location change and notify the system to begin the intervention activity. The interface 780 depicts a very brief but effective de-escalation activity 732 (e.g., an exemplary app in this themed sub-collection). This application 732 can provide for an immediate exit from an emotionally unsafe environment supported with swift, proven de-escalation tools. The application 732 includes selectable options including a return to home screen 734, a Start/Stop De-Escalation Activity 736 (e.g., "short 2 minute de-escalation activity"), and a Select New De-Escalation Activity 740. Additional and/or other selectable options to enhance the user's ability to consciously control how they lower from a crisis state to a normal state. As depicted, the avatar 782 pops up on the interface 780. The depicted avatar 782 says, "I'm going to guide you through a 4-step (e.g., release, relaxation, appreciation, and aspiration) de-escalation activity that takes 2 minutes. Are you ready?" In some implementations, the avatar 782 can automatically lead the user through the de-escalation exercise intended to help the particular user reach a normal state. The de-escalation exercises are IMMEDIATE interventions and, as such, they are intentionally short and direct. As a result, the exercises are designed to be implemented during a quick exit from any situation where the user can walk out for a 2-3 minute break—which is nearly all situations in which humans find themselves. (It is a rare occasion that we are precluded from exiting a circumstance for personal reasons.) The avatar 82 can pop up into view based on voice activation or other user selection. In other implementations, the user can choose other immediate de-escalation exercises to help lower the user to their normal state.

In some implementations, based on prior learning, the system can determine if current biometric readings warrant a conscious application intervention from the Change (Your) Environment app sub-collection. If yes, then the system can suggest an intervention. In some implementations, the user may not be able to override the system's selection (e.g., established at initial setup). Moreover, when the user makes selection of a human coach or guide versus an AI or smart coach while engaged with the application, the system can learn the user's preferences over time via self-reported feedback and system analysis of de-escalation speed following application of the intervention. Therefore, in future subsequent interventions, the system can suggest a coach or an intervention that the user would have selected on their own and/or that is optimally aligned to deliver the swiftest de-escalation.

Figure 18:
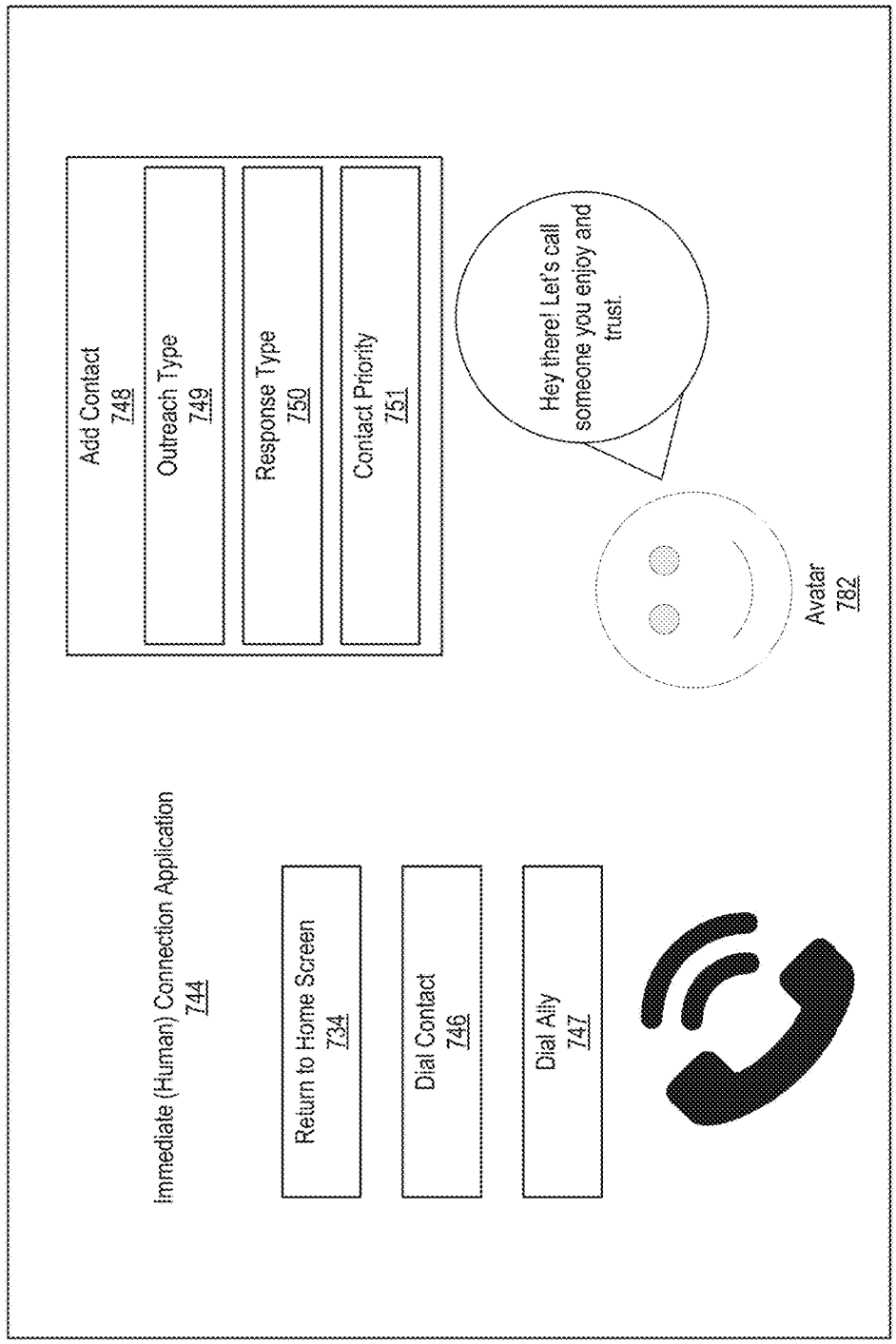

FIG. 18 depicts an exemplary verbal release sub-collection user interface 774. The interface 774 can include an Immediate (Human) Connection Application 744. This application 744 can provide immediate connection to one or more emotionally important people to the user. Family members, friends, pre-screened therapists, and/or trained advocates can be categorized as contacts for the user. One feature of this application—e.g., automatic connection to an emergency contact that cannot be overridden by the user, was mentioned above (FIG. 15) as an advantage of the system. One or more selectable options in the application 744 can include Return to Home Screen 734, a Dial Contact 746, a Dial Ally 747, and Add Contact 748. The application 744 can provide for additional and/or other selectable options to enhance the user's ability to consciously control how they immediately and decisively lower from a crisis state to a normal state. The Add Contact 748 can provide the user with options to decide an Outreach Type 749, a Response Type 750, and a Contact Priority 751. Moreover, the avatar 782 pops up in the application 744 and says, "Hey there! Let's call someone you enjoy and trust." This prompt can encourage the user to choose between calling a personal contact (such as a friend, parent, physician or other close supporter) or calling an anonymous ally that is not known to the user but accessible via the system for a different type of support and/or coaching interaction. In other implementations, a personal (emergency) contact can be automatically dialed when the application 744 is opened. For example, if the system described herein (FIG. 15) determines that the user's current state exceeds their normal state, then the system can automatically activate and make a connection or call to one or more contacts based on a priority set by the user. The user can also activate this calling feature at any time, even if the user is not currently in a crisis state. When a contact receives a call or other form of communication from the system, the contact can be notified whether the system activated the connection or whether the user activated the connection. In some implementations, the system can cycle through all of the contacts designated by the user to ensure—and until—there is some live connection (i.e., one of the contacts picks up the phone).

Figure 19:
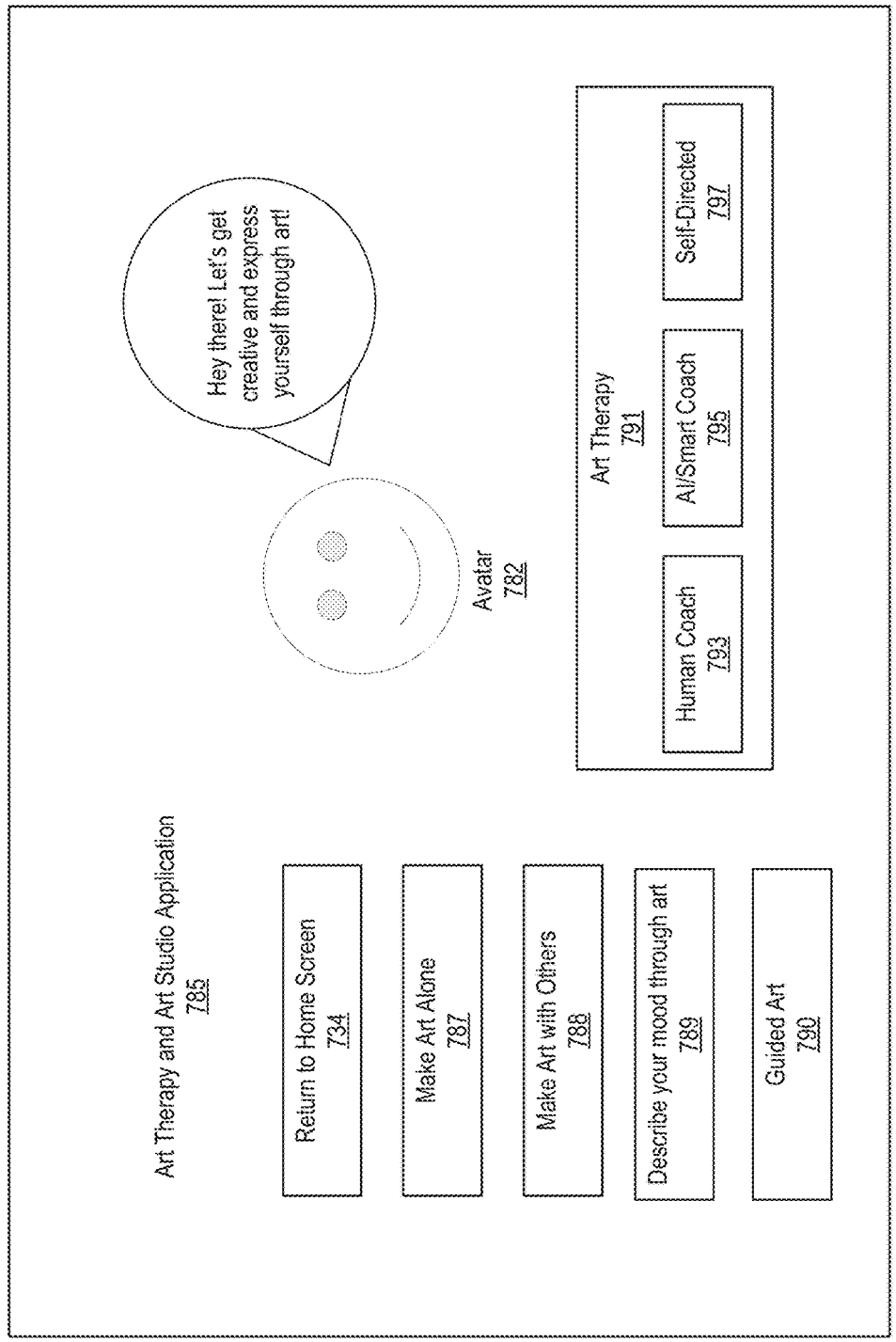

FIG. 19 depicts an exemplary creative release application sub-collection user interface 779. The interface 779 can include an art therapy and art studio application 785. This application 785 can provide immediate digital art therapy offering self-guided, human therapist-guided, and/or AI/Smart coach-based art therapy. One or more selectable options can include Return to Home Screen 734, Make Art Alone 787, Make Art with Others 788, Describe your Mood through Art 789, Guided art 790, and other art therapy 791 with a human coach 793, AI/smart coach 795, or self-guided practice 797. The user can also be presented with options to make in-app purchases of new art, art supplies, etc. The user can also be presented with options to link social media accounts to share their artwork with a community and/or to make artwork with others.

As depicted, the avatar 782 can pop up in the interface 779 and can say, "Hey There! Let's get creative and express yourself through art!" When the user selects one of the options in the art therapy/art studio application 785, the avatar 782 can be presented on additional screens or displays while the user is engaged with the application. For example, the avatar 782 can provide guidance on what to draw or what paints to use in the Guided Art 790. As another example, if the user is making art in the Make Art alone 787, the avatar 782 can provide positive feedback and/or words of encouragement to the user.

The system can also capture and learn the user's preferences. Therefore, the system can train an AI or smart coach, such as the avatar 782, to provide the user with interventions or advice helpful to the user based on their preferences and/or system-measured responses to intervention engagement, and activity. The system can also train to provide art recommendations aligned with the user's preferences. When an AI therapist/coach is activated or human therapist is called upon, either therapist can have access to immediate situational data. They can be trained to guide an art session based on the user's particular condition, preferences, and mental state. Both machine learning and other professional training can be used. For example, the AI therapist can be trained on mood, notes, issues, other inputs provided by the user in response to prompts, and prior operating state data. The AI therapist can therefore be trained to know what worked to lower the user to the normal state and what did not work. As a result, the AI therapist (e.g., the avatar 782) can provide better and more personalized recommendations to the user.

Make Art with Others 788 can provide multiple different interactive group activities/game-based group options to the user. As an example, one group activity/game can engage multiple people to edit the user's canvas or create on the user's canvas. This can give the user an opportunity to create art together with others, such as friends, family, or even strangers. Creating art with others can also be structured as a group art therapy session that can be self-guided or facilitated by a human coach and/or AI smart coach. During group art-making, people can be added to the canvas and art created by each person can populate on the user's screen real-time. Another group activity/game example can provide a small group of people with a specific end product to create (e.g., "create a mountain scene"). Each group member can be given a limited number of tools only to use to create the final piece of art together. The group members can swap tools or exchange them in a supply closet, but they cannot remove the tool restriction—they must make due with what they were provided. The group can also request additional rounds of tools prior to completing the final art product. Such a game can provide group members with a feeling of teamwork and connectivity, even if the group members are not physically proximate to each other. Another benefit of the group game is fostering collaboration with resource constraints, which creates trust, sharing, and builds skills in letting go. As another example, the user can upload their art to social media and use a particular tag that allows others to edit the art within the art studio 785. The user can also view art made by others that originated with their own work. This can provide numerous mental health benefits associated with connection and community such as providing purpose and a sense of belonging; lower stress response; reduced risk of suicide; social cohesion which can reduce social isolation, loneliness, and apathy; mitigate or avoid crises; help reach goals; and improve feelings of safety and security.

Figure 20:
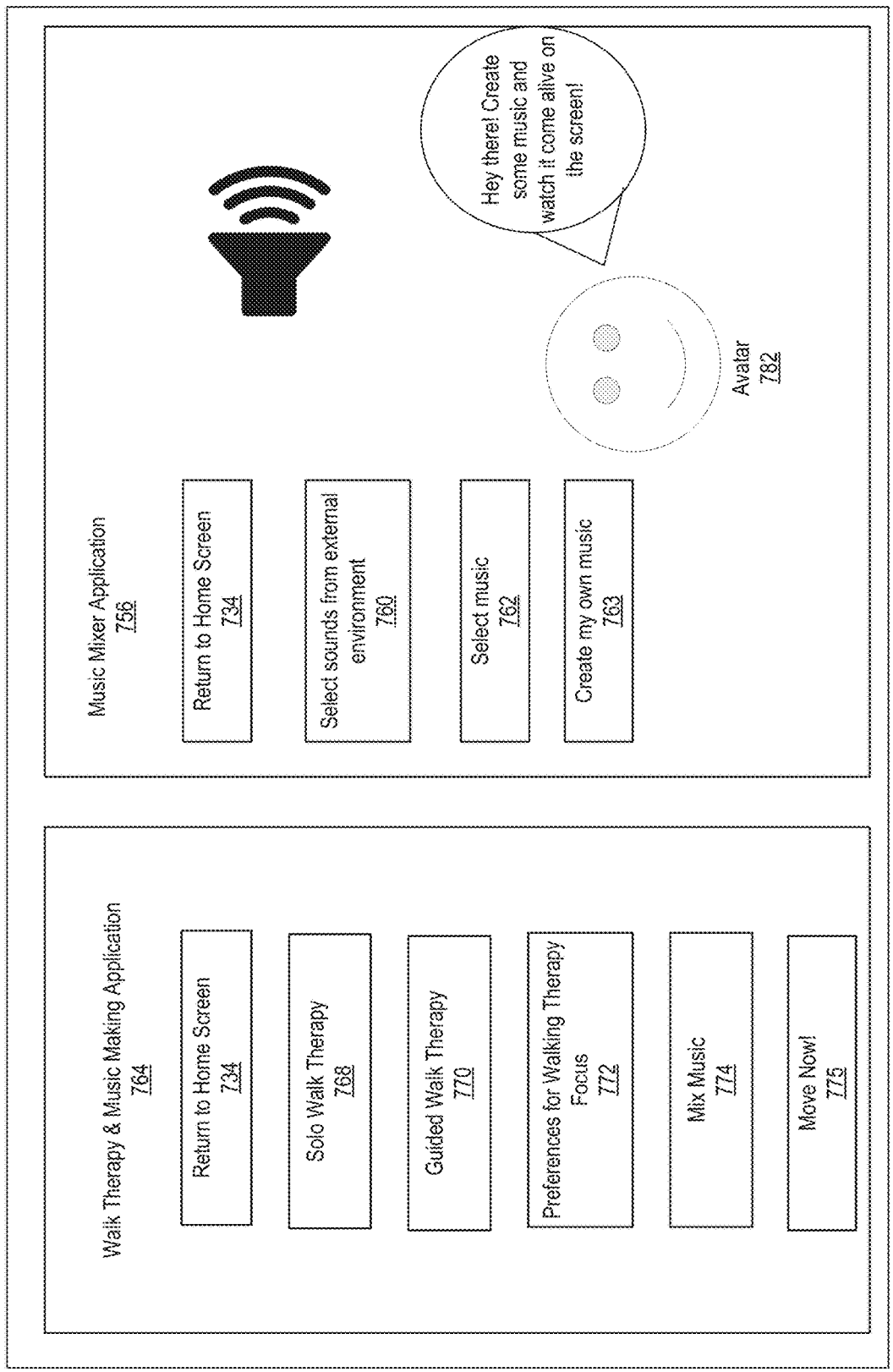

FIG. 20 depicts an exemplary physical release sub-collection application user interface 778. The interface 778 can include a walk therapy and music making application 764 and/or a music mixer application 756. The applications 764 and 756 can provide for eco-psychology and GPS-based music making and/or mixing for helping users put the benefits of nature, walk therapy, and creative expression into action. The interface 778 can provide for (1) creative intervention (e.g., create/mix music), (2) physical intervention (e.g., exercise), and (3) nature (e.g., physical outdoor excursions) to assist the user to quickly de-escalate from the crisis state. As with all the apps that are a part of the disclosed technology, there is a "Move NOW" button 775 to activate an immediate (physical) intervention. The applications 764 and/or 756 can be used with additional hardware or equipment, such as earbuds or headphones. The earbuds, for example, can tune out sounds in the world and incorporate hearing aid technology to tune in or pick up particular sounds in the world. Hybrid earbud/hearing aid hardware technology can separate external/nature sounds into different frequency (tonal) regions, or channels. A volume of each channel can be adjusted independently allowing for certain sounds to be amplified more than others, similar to an equalizer on a stereo. This functionally can allow the user an ability to capture specific sounds while engaged in nature walks. For example, a user may want to capture a song of a wood thrush bird heard while walking or a splash of fish in a pond or even a sound of car horns during rush hour. Using the disclosed technology and techniques, the user can capture and record these sounds in real-time and take them back the user's music studio in the application 756 for subsequent music making/mixing. In addition, the user can record audio of guided walk therapy sessions with a human or AI/smart therapist. This enables the session benefits to extend beyond the immediate session. The user can listen to the session multiple times or cut words from the session for subsequent use/benefit, which can overcome temporal limitations of alternative therapy sessions.

Thus, these applications 764 and 756 can offer three ways to circumvent or mitigate crisis states: (1) enabling self-guided walks in nature, 2) enabling therapist-guided (human or AI/smart coach) walk therapy sessions and (3) enabling customized music making/mixing using the library collections or by capturing sounds of nature/environmental sounds while the user is engaged in a nature walk/walk therapy.

The application 764 can include selectable options including but not limited to the Return to Home Screen 734 option, a Solo Walk Therapy 768, a Guided Walk Therapy 770, a Preferences for Walking Therapy Focus 772, and a Mix Music 774. The application 764 additionally or optionally can include an interactive map. The user can select a location on the map that the user would like to visit and/or explore. The application can map out the walk in accordance with user-selected timing/intervention duration and nature preferences. The application 764 can provide for additional and/or other selectable options to enhance the user's ability to consciously control how they lower from a crisis state to a normal state.

The music mixer application 756 can include one or more selectable options including the Return to Home Screen 734 option, a Select Sounds from External Environment 760, a Select Music 762, and a Create My Own Music 763. The application 756 can also include a display that depicts a visualization of the music chosen or created real-time by the user. The sound images/movement are created through a combination of coding and algorithms based on math and geometry to turn sound data into images real-time. The visualization is an example of a UNCONSICOUS intervention embedded in a CONSCIOUS intervention created to help the user lower to their normal operating state. Moreover, as depicted, the avatar 782 populates the interface 778 and can say, "Hey There! Create some music and watch it come alive on the screen!"

FIG. 21 depicts a user interface 783 having a post-intervention rating application 784. The application 784 can be automatically presented to the user after each intervention that the user selects or performs. For example, after the user makes music in the music mixer application 756, the user can be presented with the application 784 and asked to rate their experience with the music mixer application 756.

The application 784 can include one or more different metrics used for reviewing the performed intervention. For example, the application 784 can include a post-intervention review 791, an intervention type efficacy 792, and an intervention type reporting 793. One or more additional or fewer review metrics can be presented to the user based on the selected and performed intervention. The application 784 can provide for a level of collective and individualized feedback, which can be used, through AI and/or machine learning, to determine and generate more effective interventions for the user.

The example rating application 784 pertains to the Immediate (Human) Connection Application 744 (e.g., included in the verbal release sub-collection user interface 774), as depicted and described herein. In an example rating application 784 for the Art Therapy and Art Studio 785, the user can report on efficacy of studio objectives (e.g., get curious, seek guidance, prioritize joy), therapist/coach efficacy (e.g., AI/Smart coach versus human coach), individual human coach efficacy, single versus multiplayer efficacy, game efficacy, as well as system versus self-report evaluation. The user can also report on in-app purchases, sharing of art and/or tools/supplies, swapping art and/or tools/supplies, and limited time collections or other custom collections. Efficacy can be measured as a swift and effective reduction of the user's operating state to the normal range or normal state.

Referring to the example rating application 784 in FIG. 21, the post-intervention review 791 for the Immediate (Human) Connection Application 744 can include contacts, listed based on contact identifiers, a number of calls, a self-reported outcome, and a system-reported outcome. For example, when the user was in a crisis state, contact #2 was called once. The user reported that, in their opinion, this intervention (e.g., talking to contact #2) was not helpful (e.g.,—in lowering the user to the normal state. The system, however, reported that calling the contact #2 was beneficial (e.g., +) in lowering the user to their normal operating state. The review 791 can be advantageous for the user to see who they prefer to call when they are in a crisis and/or whether certain contacts are in fact beneficial in lowering the user to the normal state. The system-reported outcomes can be based on biometric values that are sensed in real-time before, during, and after a contact is called. Therefore, although the user may not register cognitive improvement immediately (e.g., "sense" they have lowered from their crisis state), a lowered heart rate, reduced sweating and/or other physiological change resulting from talking to a particular contact can be demarked as a positive outcome by the system. The review 791 can assist the user in understanding how they are in fact being lowered to the normal state and what measures can be taken in the future. Furthermore, the review 791 can be beneficial for training the system, as described herein. Based on the self-reported and system-reported outcomes, the system can be trained to better select or perform interventions when the user is in the crisis state. For example, the system can be trained to not call contact #2 when the user is in the crisis state because the self-reported outcome can suggest that the user does not like talking to contact #2. An additional benefit of the system is that while the user's perceptions of the contact's efficacy are subjective; the system's evaluation is objective based on the efficacy and speed of crisis state de-escalation. This objective feedback encourages another layer of learning and self-reflection by the user.

The intervention type efficacy 792 can list an intervention type, a number of times it occurred, and a percent of intervention efficacy. Still relating to the Immediate (Human) Connection Application 744, the intervention types can include listening, words of support, action ideas, plan to meet, and plan to talk more. In this example, percent values are used to demonstrate intervention efficacy. One or more other metrics can also be used to measure how effective each intervention type was in bringing the user down from the crisis state to the normal state. Moreover, the efficacy can be determined based on which intervention type, relative to each other, was fastest in lowering the user to the normal state. In this example, listening occurred 18 times and was 98% effective in lowering the user to the normal state. In other words, 98% of the 18 listening that occurred during this intervention brought the user down to the normal state faster than the other intervention types. As another example, plan to talk more occurred only 3 times and was 85% effective. This intervention type, therefore, was the slowest to bring the user down to the normal state. The system can use this efficacy information to train and determine the best intervention types in the future. For example, the system can be trained to determine that making plans to talk more with a contact or ally that is called is not going to help the user quickly get down to the normal state. The system can be trained to determine that when the user is in the crisis state, a contact that is a good listener will be automatically called because this intervention type is the most effective in quickly bringing the user back down to the normal state.

The intervention type reporting 793 can include an Ally ID, number of calls, self-reported outcome, system-reported outcome, and action taken. Reporting 793 can be a variation of the intervention type efficacy 792 and/or the post-intervention review 791. The reporting 793 can provide additional information on an efficacy of the selected intervention. This information can be beneficial to the user to determine what intervention the user prefers and/or what intervention works best for the user. This information can also be beneficial for training the system to better predict and select an intervention type when the user enters the crisis state. In this example, an Ally 991 was called once. The user reported, on a scale of 1-5, that this call was a 3. The system, on the other hand, reported that this call was a 1. The system can make this determination or rating based on, for example, the call to Ally 991 being slowest of all the other calls in lowering the user to the normal state (e.g., the user's heartrate remained high during and after the call to the Ally 991). The user, however, may not have realized that the outcome from this call was not as beneficial as the user reported because the system, rather than the user, can measure the user's biometric values and determine physiological advantages of each intervention type. Therefore, because the system reported that calling the Ally 991 is least beneficial, the system chose to block future calls to this ally. Likewise, the system chose to prefer calls to ally 672 over the other allies because both the user and system reported that calling the Ally 672 was most beneficial (e.g., 5/5 score; biometric values of the user were lowered in the least amount of time relative to other intervention types; the user reported feeling good after calling the Ally 672 and the user's feelings are aligned with the user's biometric values and the system's reporting). The actions can be selected or chosen by the system based on training the system, as described herein. In other implementations, the actions can be manually selected by the user.

In some embodiments, each of the processes 200, 300, 400, 500, 600 and 700 represent exemplified and non-limiting overviews of the systems and methods of the disclosed technology.

As described herein, the present technology is a learning system on two levels. The first level is computer-driven via simple feedback (such as which response stimulation(s) were provided to a particular user in response to detection of a given set of physiological symptoms, and how well did those response stimulation(s) work to return the user to a normal range of states), as well as artificial intelligence, machine learning, deep learning, neural networks and/or other computer methods and algorithms that are part of the intervention determiner. The intervention determiner uses one or more of these technologies to learn, over time and training, what interventions perform swiftly and effectively to diffuse the crisis state and return the person or persons to their Normal State Range.

The second level is human driven in that after the intervention determiner concludes that a CONSCIOUS intervention is needed and communicates this to the user device(s) to ultimately reach the user or group, the person or persons implements a chosen method or path. Their action then drives a corresponding physical and/or behavioral response, which the user is no doubt cognitively aware. This user-driven action-response sequence will cause the person/persons to self-assess and/or evaluate the efficacy of the chosen intervention on their crisis state which, in turn, will create greater self-understanding and drive subsequent intervention best practices. In summary, like the primary computer-driven system, a secondary human-driven system trains the person or persons to learn what interventions perform optimally in each situation, circumstance, environment, operational state and severity thereof.

The DUAL INTERVENTION system, underscoring the disclosed technology that includes a system and methods, directly and indirectly influences and modulates the human stress response.

Figure 22:
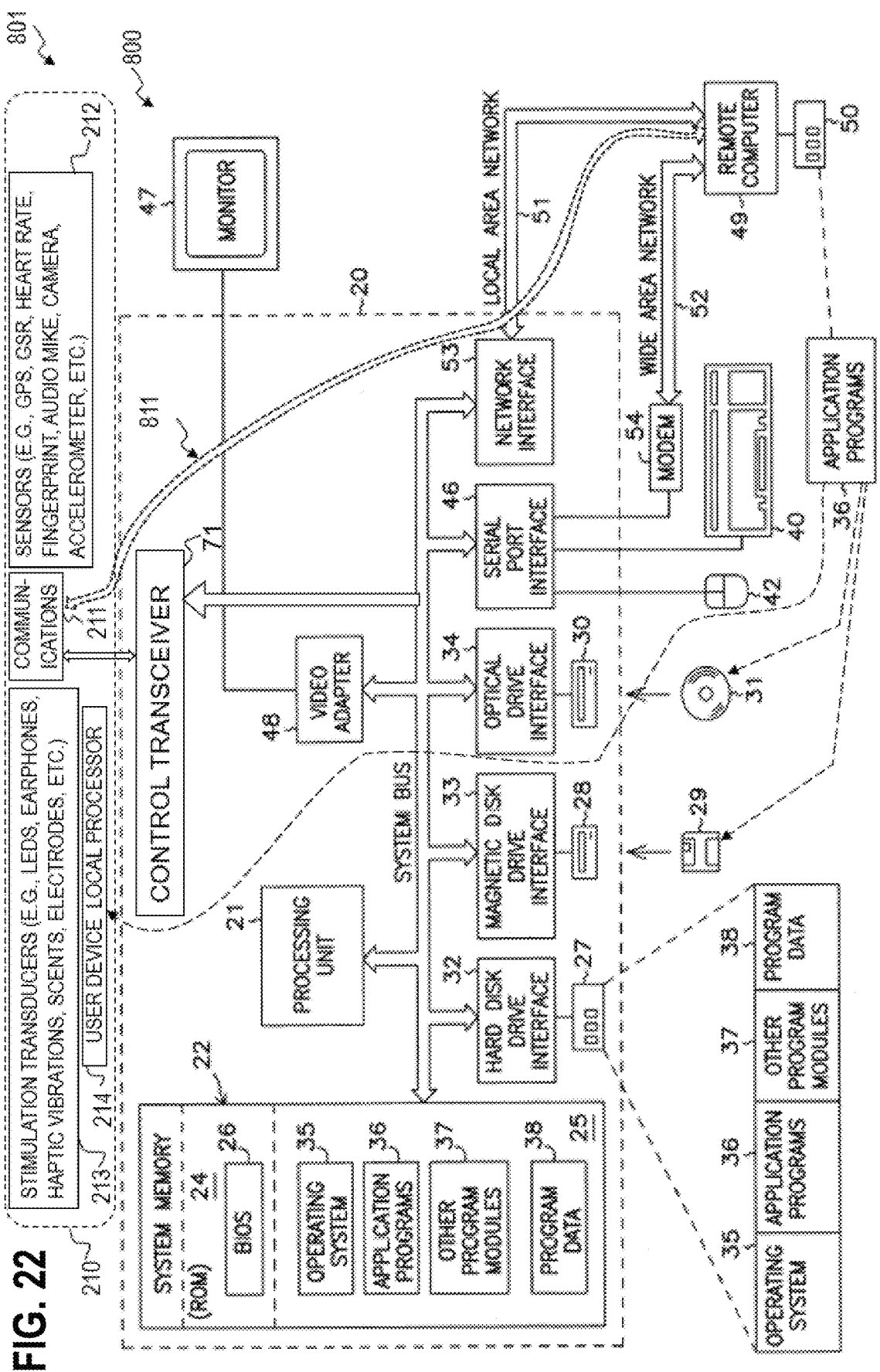
FIG. 22 is a block diagram of an exemplary system 801 for implementing the present invention that includes a conventional general-purpose computing system 800 and one or more user device(s) 210, according to some embodiments of the disclosed technology.

FIG. 22 is a block diagram of an exemplary system 801 for implementing the disclosed technology that includes a conventional general-purpose computing system 800 and one or more user device(s) 210. In some embodiments, conventional general-purpose computing system 800 includes a conventional personal computer 20, including a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random-access memory (RAM) 25. A basic input/output system (BIOS) 26, containing the basic routines that help to transfer information between elements within the personal computer 20, such as during start-up, is stored in ROM 24. The personal computer 20 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer readable instructions, data structures, program modules and other data for the personal computer 20. Although the exemplary environment described herein employs a hard disk, a removable magnetic disk 29, and a removable optical disk 31, it will be appreciated by those skilled in the art that other types of computer readable media which can store data that is accessible by a computer, such as magnetic cassettes, flash memory cards, digital video disks, Bernoulli cartridges, random access memories, read only memories, and the like may also be used in the exemplary operating environment.

A number of program modules may be stored on the hard disk, magnetic disk 29, optical disk 31, ROM 24 or RAM 25, including an operating system 35, one or more applications programs 36, other program modules 37, and program data 38. A user may enter commands and information into the personal computer 20 through input-devices such as a keyboard 40 and a pointing device 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB). A monitor 47 or other type of display device is also connected to the system bus 23 via an interface, such as a video adapter 48. In addition to the monitor, personal computers typically include other peripheral output devices, not shown, such as speakers and printers.

The personal computer 20 may operate in a networked environment using logical connections to one or more remote computers, such as a remote computer 49. The remote computer 49 may be another personal computer, a server, a router, a network PC, a peer device or other common network node, and typically includes many or all of the elements described above relative to the personal computer 20, although only a memory storage device 50 has been illustrated in FIG. 8A. The logical connections depicted in FIG. 8A include a local area network (LAN) 51 and a wide area network (WAN) 52. Such networking environments are commonplace in offices, enterprise-wide computer networks, intranets, and the Internet.

When used in a LAN networking environment, the personal computer 20 is connected to the local network 51 through a network interface or adapter 53. When used in a WAN networking environment, the person computer 20 typically includes a modem 54 or other means for establishing wireless and/or wired communications over the WAN 52. The modem 54, which may be internal or external, is connected to the system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

In some embodiments, each user device 210 includes a user device communications interface 211 (such as Bluetooth®, Wi-Fi and/or cellular telephony or the like), and a plurality of sensors 212 (such as global-positioning system (GPS) sensors for location, spatial orientation, speed, etc., galvanic skin response (GSR) sensors, heart-rate sensors, fingerprint sensors (for device activation, authorization or locking), audio microphone(s) for voice and ambient noise evaluations, camera(s) for analysis of hand gestures, posture, facial expressions, and the like, accelerometers, gyroscopes and/or magnetometers for determining orientation, speed, acceleration and the like, and other sensors as may be needed to help determine a person's state. In some embodiments, each user device 210 also includes a local processor and its database and programs that are used to determine the user's state and, based on that determination, send one or more commands to intervention actuators 213, which in various embodiments include one or more of the following: LEDs and visual displays for visual stimulation, earphones or other audio transducers for audio stimulation, haptic vibrators, pneumatic or hydraulic compression cuffs, or the like for touch stimulation, scent emitters for sense-of-smell stimulation, salt, sweetness, or citric-acid sources or the like for taste stimulation, and/or electrodes and micro-current drivers for electrical stimulation. In some embodiments, the data from the sensors 212 and the data to the interventional actuators 213 are streamed from and among apps or other software modules executing in individual parts of user device 210 and/or server 220.

In some embodiments, each of the intervention actuators 213 is programmable to provide a range of stimulation types and stimulation intensities in order to provide interventions that are either unconscious (imperceptible to the user) or conscious (perceptible to the user).

FIG. 23 is a block diagram of a simplified exemplary system 802 for implementing the disclosed technology that, in contrast to system 801, includes much or all of the functionality of conventional general-purpose computing system 800 instead implemented in a smart-phone system of wearable devices in one or more user device system(s) 210, according to some embodiments of the present invention. In some embodiments, user-device local processor 214 includes all of the parts and/or functionality of intervention server 220 and database 221.

FIG. 24A is a block diagram of a process 901 for dispensing programs into a personal computer 990 or similar information-processing device, for example, a new user device being purchased by its initial user, according to some embodiments of the disclosed technology. Conventional methods for dispensing soft assets into a personal computer 990 occasionally include downloading 992 of soft assets from a network 991. For example, network 991 could be a manufacturer's internal network used to preload programs and audio-visual interventions (soft assets) into a user device being assembled. Further, software. videos and music are commonly available for purchase (or even for free, in some cases) and immediate download from the internet 991 via a process of "downloading." Further, some assets are available as downloads from proprietary wireless networks 991 (such as a corporation's internal network), or external networks such as those operated by cell-phone carriers. In some embodiments of the disclosed technology, loading methods also include uploading, media-installing 994 of soft assets from physical media 993 (e.g., USB FLASH memory, and the like), sometimes also requiring substantial amounts of manual input 996 from a user via an interactive input device 995 (such as a manual keyboard). It takes a considerable amount of the user's time and mental energy (the drain on the user from the concentration needed to perform the various unfamiliar tasks, as well as the boredom from waiting for the process to complete), as well as power from the electrical grid needed to download and install a large selection of soft assets from the internet 991, or to install soft assets from media 993 and/or manual input device 995.

In contrast, as shown in FIG. 24B, one aspect of the set up process 902 of the disclosed technology provides loading 988 of soft assets and/or training data and personal data, wherein training and personal data are derived from the user's past activities and kept on a user's storage medium 987 that is operatively coupled to computer 980 (e.g., in some embodiments, the user device 210), in order that the user's personal data are loaded onto the user's device 980. In some embodiments, the crisis detection and intervention programs and more-universal human and group data and thresholds are downloaded 982 from server(s) on the internet 991.

Figure 25:
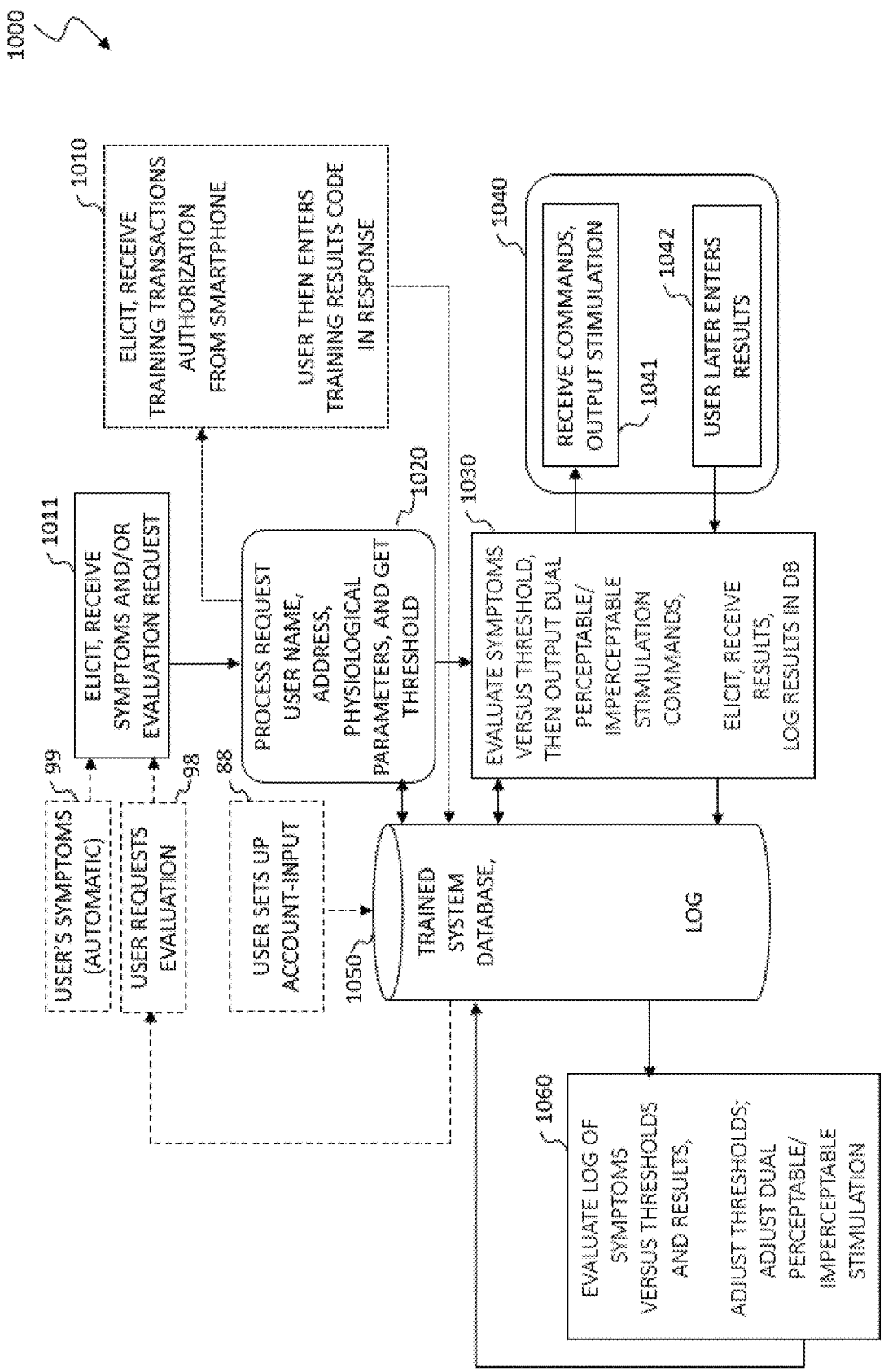
FIG. 25 is a block diagram of system 1000, according to some embodiments of the disclosed technology.

FIG. 25 is a block diagram of system 1000, according to some embodiments of the disclosed technology. In some embodiments, system 1000 includes a data-receiving block 1011 (e.g., in some embodiments, a software routine) that elicits and receives user data (such as physiological and behavioral parameters 99 that are collected by sensors 212 in the user device 210, and/or a verbally or manually entered request 98 for evaluation of the user's symptoms or state of mind). The data collected by block 1011 are passed to processing block 1020 that processes the request based on the user's name, address, or other identifier (such as an anonymous identifier that is associated with a particular user who wishes to keep private certain personal data, characteristics, and/or interventions), along with the personal threshold(s) previously set or determined for that user. The data processed block 1020 are passed to evaluation block 1030 which outputs commands to intervention/stimulation block 1040 to activate interventions 1041 (imperceptible and/or perceptible stimulation) based on evaluation of the data from block 1020 and on parameters that are stored on the trained database 1050. Later, in some embodiments, the user enters results 1042 (either explicitly based on the user's emotions or wellbeing perceptions, or via physiological data automatically captured by the user's device 210). Block 1030 elicits and receives the results data and logs that data into database 1050. In some embodiments, block 1010 is used to gather initial baseline and other training data used to set thresholds in database 1050. In some embodiments, block 1060 is used to gather ongoing and other adjustment and learning data used to modify thresholds in database 1050 based on the results of prior interventions to this particular user or group or on results from other like-situated users or groups.

In the description that follows, the disclosed technology can be described with reference to acts and symbolic representations of operations that are performed by one or more computers, unless indicated otherwise. As such, it will be understood that such acts and operations, which are at times referred to as being computer-executed, include the manipulation by the processing unit of the computer of electrical signals representing data in a structured form. This manipulation transforms the data or maintains it at locations in the memory system of the computer, which reconfigures or otherwise alters the operation of the computer in a manner well understood by those skilled in the art. The data structures where data is maintained are physical locations of the memory that have particular properties defined by the format of the data. However, while the disclosed technology is being described in the foregoing context, it is not meant to be limiting as those of skill in the art will appreciate that various of the acts and operation described hereinafter may also be implemented in hardware.

People want to be free from crisis operational states. Crisis states are precipitated by the human stress response, disrupt normal physical and behavioral functioning, and drive unintended/undesired actions that can result in irreparable damage to oneself or others' health and wellbeing and/or overarching life or livelihood.

As shown in the figures described herein (e.g., refer to FIG. 3), people embody a range of operational states at any given time from a Restorative State, to a Normal State, a Warning State, an Alert State, and finally a state of Major Emergency. When a person is in an elevated state, e.g., that which is beyond their baseline individualized state range 116, and instead in the crisis-states range 117 (including warning state 130, alert state 140, and emergency state 150), they may find themselves out of control and/or unable to cope or make decisions in a manner that leads to their own or others' best interests. Crisis states 117, for many members of the population, are often prolonged and/or recurring, and can lead to harm to self and others.

In some embodiments, the disclosed technology provides a computer implemented method for crisis state detection and intervention of a person. This method includes: providing a computer system designed to detect and intervene non-normal, elevated crisis operating states; use of an intervention system/server, one or more user devices, and database(s) that together via network communications (wired or wireless) ascertain a crisis state though physical and/or behavioral indicators; deducing, via the intervention determiner process in the intervention system/server, the operational state of a user or users (in the case of the related technology) from one or more user devices that include input sensors and transmit data via the communication interface over the network to the intervention system/server and then to the user device(s)/output alert system; and administering an immediate, dual intervention of a conscious and unconscious form to de-escalate the crisis operating state of a person.

In some embodiments of the method, the one or more user devices with input sensors that monitor, measure any physical (e.g., heart rate, blood flow) and/or behavioral (e.g., bodily movement, speed, pace or volume of voice,) indicator of a person.

In some embodiments of the method, the system, encompassing the intervention system/server, user device(s) and database(s), comprises any of a microcontroller, microprocessor, a digital signal processor and a system on a chip or in the cloud.

In some embodiments of the method, the intervention system/server detects a person's operational state—in collaboration and coordination with one or more user devices/input devices—utilizing any of computational algorithms, statistical analysis, database, knowledge base, neural network, and machine learning algorithm.

In some embodiments of the method, the person's operating state includes a Normal State (Normal and Restorative) or Crisis State (Warning, Alert, and Major Emergency) state. In some such embodiments, in the crisis state, the person is experiencing the human stress response characterized by a time of intense difficulty or danger, elevated or extreme physical and/or behavioral arousal, threatening the very stability of the person or persons.

In some embodiments of the method, the system-induced, unconscious intervention comprises any sensation that engages the person's sight, smell, hearing, taste, or touch/feeling unconsciously, without attentional diversion or distraction from current activity.

In some embodiments of the method, the conscious intervention is comprised of an alert (sight, sound etc.) that is recognized by the person and induces them to take a specific action or choose that the system take an action (e.g., artificial intelligence-based recommendation) to modulate and mitigate their crisis/stress response.

In some embodiments of the method, the computer-induced user action (self-selected or system-driven) consists of an experience, sensation, guidance, game, training, or other immediate immersion delivered via computer application and aligned with at least one of several crisis mitigation areas which may include, among others, verbal release, physical release, creative release, change environment or other mitigators).

In some embodiments of the method, the method encompasses the intervention system/server, user device(s) and database(s) and additionally includes time tracking and/or recording user entry into and departure from a crisis state; data capture, data housing, reporting, analysis, and synthesis.

In some embodiments of the method, the immediate, real-time computer-driven, dual intervention (conscious and unconscious) directly and/or indirectly diffuses the crisis state by influencing the human stress response to return the user to a normal operating state.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the disclosed technology should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A system for crisis state detection and intervention of a user, the system comprising:
a computing device having:
one or more biometric sensors configured to detect biometric conditions of the user;
a transceiver configured to automatically transmit the biometric conditions in real-time; and
a computing system having one or more processors, the computing system configured to:
train one or more machine learning models that are configured to be used to determine different physiological states of the user, wherein the one or more machine learning models are trained based at least in part on (i) user-inputted evaluation information that includes initial threshold indicators for the different physiological states of the user and (ii) historical biometric conditions of the user, wherein the training comprises determining threshold indicators for each of the different physiological states of the user, the threshold indicators being unique to the user, wherein the different states comprise a crisis state and a normal state;
store the trained models in a data store in association with the user;
continuously receive, from the transceiver, the biometric conditions of the user;
retrieve, from the data store, at least one of the trained models;
identify, based on providing the biometric conditions of the user as input to the retrieved at least one model, a current physiological state of the user, the current physiological state being at least one of the crisis state and the normal state that is unique to the user;
generate, based on a determination that the current physiological state of the user is the crisis state, intervention instructions that are configured to be automatically executed by the computing device to produce an action on the computing device that is configured to lower the user from the crisis state to the normal state that is unique to the user;
transmit, to the computing device, the intervention instructions, wherein in response to receiving the intervention instructions and without user permission or input at the time of receiving the intervention instructions, the computing device is configured to automatically perform the intervention instructions on the computing device and the computing system is configured to continuously receive the biometric conditions of the user as the intervention instructions are executed, wherein the biometric conditions received during execution of the intervention instructions comprise intervention biometrics indicating responses of the user to the execution of the intervention instructions; and
iteratively train the models associated with the user based on the intervention biometrics, wherein the iterative training comprises: (i) periodically measuring and determining operating state parameters of the user, (ii) updating correlations between the different physiological states of the user and the measured and determined operating state parameters of the user, and (iii) calibrating the models based on the updated correlations.

2. The system of claim 1, wherein the intervention instructions include automatically calling an emergency contact of the user without permission or user input from the user, the computing device being further configured to:
prompt, during an initial setup of the system, the user for (i) a phone number for each user-designated emergency contact and (ii) a call priority for each of the user-designated emergency contacts;
in response to receiving the intervention instructions from the computing system, select an emergency contact from the user-designated emergency contacts based on the call priority for the selected emergency contact being greater than call priorities for each of the user-designated emergency contacts; and
automatically call the selected emergency contact using the phone number for the selected emergency contact.

3. The system of claim 1, wherein the computing system is further configured to determine the normal state of the user based on one or more historic and present biometric conditions of the user being below a threshold value, wherein the historic and present biometric conditions include at least one of a heartrate, a blood flow, sweat, bodily movement, volume of voice, and speaking pace of the user.

4. The system of claim 3, wherein the computing system is configured to identify the crisis state of the user based on determining that the biometric conditions of the user exceed a threshold value for biometric conditions of the user in the normal state.

5. The system of claim 1, wherein the intervention instructions include providing audio, sensory, or physical feedback by the computing device to the user, wherein in response to receiving the intervention instructions from the computing system, the computing device is further configured to:
detect a presence of the user;
select the audio, sensory, or physical feedback to provide to the user based on user preference and how much the biometric conditions of the user exceed a threshold value, wherein the audio, sensory, or physical feedback includes (i) a pulse that mimics a target heartrate of the user that is below the threshold value, (ii) a pulse that mimics a target breathing rate of the user that is below the threshold value, (iii) a sound that calms the user, or (iv) audio from an external environment that calms the user; and
provide the selected audio or physical feedback to the user while the presence of the user is detected and until the biometric conditions of the user are detected as being less than the threshold value.

6. The system of claim 5, wherein the audio from the external environment is generated in a process comprising:
recording, using the computing device and at a first time, sounds from the external environment that cause the biometric conditions of the user to lower to less than the threshold value;
providing, by the computing device and at a second time, the recorded sounds as the audio from the external environment when the biometric conditions of the user are detected as being greater than the threshold value, wherein the first time is earlier than the second time.

7. The system of claim 1, wherein the intervention instructions include displaying, at a user interface display of the computing device, one or more interactive applications targeted at lowering the user from the crisis state to the normal state, wherein the one or more interactive applications include instructions prompting the user to perform actions that, when executed, cause the user to lower from the crisis state to the normal state, the actions including at least one of (i) playing a game with one or more other users, (ii) creating artwork with one or more other users, wherein the users contribute to a shared canvas that is displayed and updated in real-time at each computing device of the users, (iii) creating music using sounds from an external environment, (iv) performing an automated breathing exercise, and (v) taking a guided walk in a physical environment, wherein the guided walk is determined by the computing device and based on a current location of the user.

8. The system of claim 7, wherein the computing system is further configured to automatically select an interactive application from the one or more interactive applications based on determining, using the one or more machine learning models, that the current physiological state of the user is the crisis state and the crisis state is above a threshold indicator of a crisis state, and
the computing device is configured to, in response to receiving the intervention instructions from the computing system, display, at the user interface display of the computing device, the selected interactive application.

9. The system of claim 1, wherein the computing device is further configured to (i) automatically execute the intervention instructions while the detected biometric conditions exceed a threshold value indicative that the user is operating in the crisis state and (ii) terminate the intervention instructions when the biometric conditions are detected as being lower than the threshold value.

10. The system of claim 1, wherein the computing system is further configured to determine an efficacy score for executed intervention instructions in lowering the user from the crisis state to the normal state, wherein the efficacy score is based on an amount of time taken to lower the user from the crisis state to the normal state being less than a threshold value.

11. The system of claim 10, wherein:
the computing device is further configured to:
prompt, after execution of the intervention instructions, the user to provide input about an effectiveness of the executed intervention instructions, and
transmit, to the computing system, the user feedback; and
the computing system is further configured to:
receive, from the computing device, the user feedback,
increase the efficacy score of the intervention instructions when the user feedback corresponds to the amount of time taken to lower the user from the crisis state to the normal state being less than the threshold value, and
modify the generated intervention instructions based on the increased efficacy score, wherein the computing device can be configured to receive, from the computing system, intervention instructions having a higher efficacy score than intervention instructions having a lower efficacy score.

12. The system of claim 1, wherein the computing system is further configured to provide intervention instructions comprising an interactive artificial intelligence (AI) coach, wherein the AI coach is displayed, at the computing device, and programmed to provide feedback to the user, the feedback being updated in real-time based on at least one of (i) the detected biometric conditions of the user and (ii) actions taken by the user as user input on the user interface display and in response to prompts from one or more interactive applications presented on the user interface display at the computing device.

13. The system of claim 12, wherein the feedback provided by the AI coach includes words of encouragement or guidance through one or more of the interactive applications.

14. The system of claim 1, wherein the computing system is further configured to transmit, to the computing device and based on determining that the crisis state of the user is below the threshold level, instructions causing the computing device to present, on the user interface display, one or more user-selectable interactive applications.

15. The system of claim 1, wherein the intervention instructions include one or more of (i) automatically calling an emergency contact of the user without consent from the user, (ii) displaying, at a user interface display of the computing device, one or more interactive applications targeted at lowering the user from the crisis state to the normal state, and (iii) providing audio, sensory, or physical feedback by the computing device to the user.

16. The system of claim 1, wherein the intervention instructions include two or more of (i) automatically calling an emergency contact of the user without consent from the user, (ii) displaying, at a user interface display of the computing device, one or more interactive applications targeted at lowering the user from the crisis state to the normal state, and (iii) providing audio, sensory, or physical feedback by the computing device to the user.

17. The system of claim 1, wherein the intervention instructions include (i) automatically calling an emergency contact of the user without consent from the user, (ii) displaying, at a user interface display of the computing device, one or more interactive applications targeted at lowering the user from the crisis state to the normal state, and (iii) providing audio, sensory, or physical feedback by the computing device to the user.

18. The system of claim 1, wherein the intervention instructions cause the computing device to perform at least one of unconscious intervention or conscious intervention on the user, the unconscious intervention causing a sensory change for the user and the conscious intervention causing a mental change for the user.

19. The system of claim 7, wherein, in response to receiving the intervention instructions from the computing system, the computing device is further configured to:
lock, for a predetermined amount of time and without user permission or input, the user interface display when the one or more interactive applications are displayed, wherein locking the user interface display prevents the user from exiting the one or more interactive applications that are displayed;
prompt the user to perform one or more actions in the one or more interactive applications that are displayed on the user interface display; and
unlock the user interface display based on (i) the user completing the one or more actions, (ii) the predetermined amount of time exceeding a threshold amount of time, or (iii) the detected biometric conditions of the user being lower than a threshold level.

20. The system of claim 1, wherein the iterative training further comprises training the one or more machine learning models based on an amount of time taken to lower the user from the crisis state to the normal state and an efficacy score of the executed intervention instructions.

* * * * *